(12) United States Patent
Gorin et al.

(10) Patent No.: US 8,546,322 B2
(45) Date of Patent: Oct. 1, 2013

(54) INHIBITORS OF INTRACELLULAR UROKINASE PLASMINOGEN ACTIVATOR AND METHODS OF USE THEREOF

(75) Inventors: Fredric A. Gorin, Davis, CA (US); Michael H. Nantz, Louisville, KY (US)

(73) Assignee: The Regents of the University of California, Oakland, CA (US)

( * ) Notice: Subject to any disclaimer, the term of this patent is extended or adjusted under 35 U.S.C. 154(b) by 206 days.

(21) Appl. No.: 12/671,824

(22) PCT Filed: Aug. 1, 2008

(86) PCT No.: PCT/US2008/071996
§ 371 (c)(1),
(2), (4) Date: Jan. 13, 2012

(87) PCT Pub. No.: WO2009/020877
PCT Pub. Date: Feb. 12, 2009

(65) Prior Publication Data
US 2012/0108494 A1    May 3, 2012

Related U.S. Application Data

(60) Provisional application No. 60/953,796, filed on Aug. 3, 2007.

(51) Int. Cl.
*A61K 31/4965* (2006.01)

(52) U.S. Cl.
USPC ........... 514/1.3; 514/1.8; 514/14.6; 514/15.6; 514/15.7; 514/19.3

(58) Field of Classification Search
None
See application file for complete search history.

(56) References Cited

U.S. PATENT DOCUMENTS

| 7,863,415 | B2 * | 1/2011 | Gorin et al. | 530/329 |
| 2006/0160746 | A1 * | 7/2006 | Gorin et al. | 514/17 |
| 2006/0264459 | A1 | 11/2006 | Salvati et al. | |

FOREIGN PATENT DOCUMENTS

WO   WO 03/039545 A2   5/2003

OTHER PUBLICATIONS

International Search Report mailed on Mar. 24, 2009, for International Application No. PCT/US2008/071996, filed on Aug. 1, 2008, 1 page.
Palandoken et al., "Amiloride Peptide Conjugates: Prodrugs for Sodium-Proton Exchange Inhibition," Journal of Pharmacology and Experimental Therapeutics, 2005, vol. 312, No. 3, pp. 961-967.
Pato, "Synthesis of Macromolecular Conjugates of a Urokinase Inhibitor: Amioride," Journal of Bioactive and Compatible Polymers, 1999, vol. 14, No. 2, pp. 99-121.
Supplementary European Search Report, Jan. 31, 2012, EP Application No. 08797050.5, 7 pages.

* cited by examiner

*Primary Examiner* — Christina Bradley
*Assistant Examiner* — Kristina M Hellman
(74) *Attorney, Agent, or Firm* — Kilpatrick Townsend & Stockton LLP

(57) ABSTRACT

The present invention provides compositions comprising amiloride amino acid and peptide conjugates. Efficient methods are also provided for administering the compositions for treating cancer and for delivering an amiloride conjugate into cancer cells in a subject in need thereof.

3 Claims, 17 Drawing Sheets

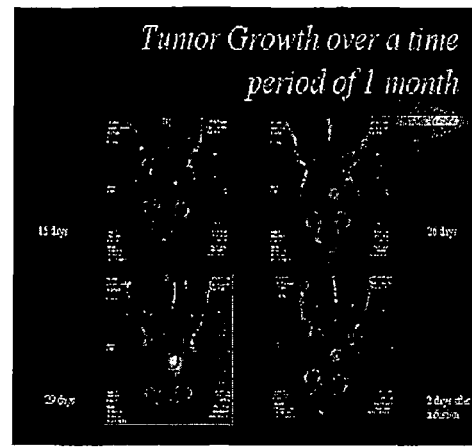
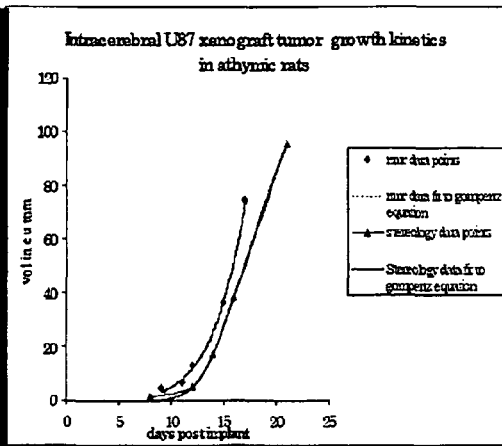
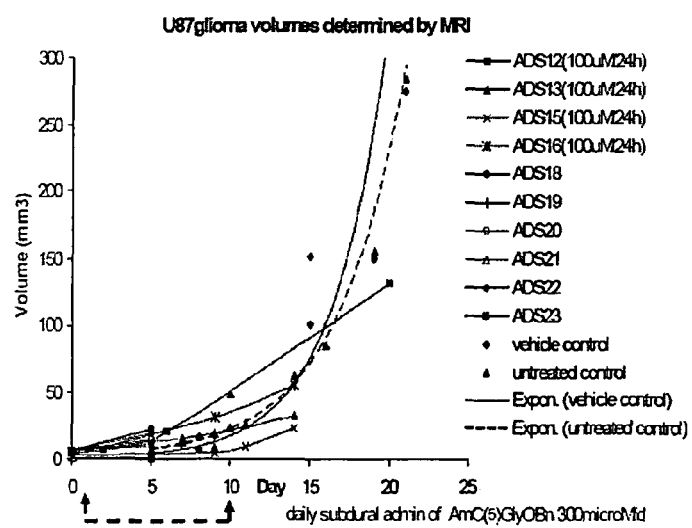
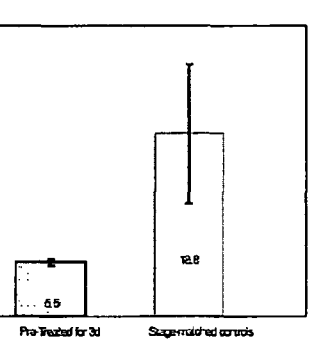
Figure 6

Correlation of uPA inhibition with cytotoxicity for select C(2)/C(5)/C(6) amiloride analogs

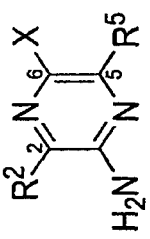

| Compound | $R^2$ | $R^5$ | X | uPA $IC_{50}$ | NHE1 $IC_{50}$ | NCX1.1 $IC_{50}$ | glioma cytotoxicity[b] | Pan-caspase and caspase-3 sensitivity (2uM) with 250uM drug at 24 and 48h[a] |
|---|---|---|---|---|---|---|---|---|
| amiloride | acyl guanidine $(H_2N)_2C=NC(O)-$ | $NH_2$ | Cl | 7 μM | 60 μM* | 690 μM[#] | (+) | (-)/(-) |
| DCB | acyl guanidine[d] $(RHN)(H_2N)C=NC(O)-$ | $NH_2$ | Cl | 3 μM | 10-15 μM | 9 nM[$] | (+++) 100% at 48h ≥ 100uM | (-)/(-) |
| 38B Am-C(5)-Gly-OBn | acyl guanidine $(H_2N)_2C=NC(O)-$ | $NHCH_2CO_2Bn$ | Cl | 3 μM | 13 μM | >250 μM (nd) | (++) 100% at 48h ≥ 250uM | (-)/(-) |
| 74A Am-C(5)-Gly-OH | acyl guanidine $(H_2N)_2C=NC(O)-$ | $NHCH_2CO_2H$ | Cl | 17 μM | 13 μM | >250 μM (nd) | (-) | (-)/(-) |

Figure 12A

| | | | | | |
|---|---|---|---|---|---|
| 74B dechloro- Am-C(5)-Gly-OH | acyl guanidine (H₂N)₂C=NC(O)- | NHCH₂CO₂H | H | 47 μM | | (-) |
| 42B amide- Am-C(5)-Gly-OBn | carboxamide H₂NC(O)- | NHCH₂CO₂Bn | Cl | 69 μM | | (-) |
| 25 amidox- Am-C(5)-Gly-OBn | amidoxime H₂NC(NOH)- | NHCH₂CO₂Bn | Cl | 74 μM | | (-) |
| 63A amidox- Am-C(5)-Gly-OH | amidoxime H₂NC(NOH)- | NHCH₂CO₂H | Cl | 231 μM | | (-) |
| 68D dechloro-amidox- Am-C(5)-Gly-OH | amidoxime H₂NC(NOH)- | NHCH₂CO₂H | H | 279 μM | | (-) |
| 49C amidine- Am-C(5)-Gly-OBn | amidine H₂NC(NH)- | NHCH₂CO₂Bn | Cl | 4 μM | ++ (100% inhib at 100uM) | (+) 50% at 72h at ≥250uM |
| 77A amidine- Am-C(5)-Gly-OH | amidine H₂NC(NH)- | NHCH₂CO₂H | Cl | 237 μM | | (-) |
| 76B dechloro-amidine- Am-C(5)-Gly-OH | amidine H₂NC(NH)- | NHCH₂CO₂H | H | 212 μM | | (-) |

Figure 12B

[a] calculated using ChemDraw Ultra 7.0.1; [b] U87 glioma cells at 200 µM; [c] ref. 1; [d] R = 3,4-dichloro-benzyl; [e] log P experimentally determined;

*J. Biol. Chem., Vol. 282, Issue 27, 19716-19727, July 6, 2007

European Journal of Medicinal Chemistry Volume 36, Issues 7-8, August 2001, Pages 597-614

&Cytotoxicity using compounds at 250 uM determined at: exp 1 24 and 48 hours in presence and absence of Z-VAD-fmk exp 2- at 250 uM drug concentration determined at 24 and 48 hours in presence and absence of Z-DEVD-fmk) vs stage-matched controls; WST assay and trypan blue cell death of detached cells.

ref 1: *Bioorganic & Medicinal Chemistry* 12 (2004) 3391–3400.

uPA enzyme: Calbiochem cat# 672112
Urokinase, Human urine
specific activity: 100000.0 U/mg
Lot# D000 17540 uPA substrate: Z-Gly-Gly-Arg 7-amido-4-methylcoumarin hydrochloride nicrotiter plate assay conditions:

Figure 12C

INHIBITORS OF INTRACELLULAR UROKINASE PLASMINOGEN ACTIVATOR AND METHODS OF USE THEREOF

CROSS-REFERENCES TO RELATED APPLICATIONS

This application claims the benefit of priority to U.S. Provisional Application Ser. No. 60/953,796, filed Aug. 3, 2007, the contents of which are incorporated herein by reference, in their entirety.

STATEMENT AS TO RIGHTS TO INVENTIONS MADE UNDER FEDERALLY SPONSORED RESEARCH AND DEVELOPMENT

This invention was made with support from the U.S. Government. The Government has certain rights in this invention pursuant to contract R01 NS 40489 awarded by the National Institutes of Health and CRCC GRANT NO. 2006-7 awarded by University of California Cancer Research Coordinating Committee

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

High-grade malignant gliomas (i.e., astrocytomas) are the most commonly occurring type of lethal adult brain tumor and are increasing in incidence (Legler et al., *J. National Cancer Inst.*, 91:1382-1390 (1999)). The median survival is approximately 9-12 months following diagnosis, as the tumors are usually refractory to aggressive multimodal therapy (Brandes et al., *Amer. J. Clin. Onc.*, 22:387-390 (1999)).

Tumor cell proliferation, migration and invasion into the surrounding extracellular matrix is facilitated by a variety of mechanisms. Thus, highly proliferative tumors are known to have increased glycolytic fluxes with elevated levels of intracellular lactate and pyruvate (Oudard et al., *Anticancer Res.*, 17:1903-1911 (1997); Erecinska et al., *J. Neurochem.*, 65:2765-2772 (1995)), which are optimal at an alkalotic pH (Dobson et al., *Amer. J. Physiol.*, 250:R71-76 (1986); Hasuda et al., *Onc. Res.*, V6:259-268 (1994)). Further, tumor cell migration and invasion into the surrounding extracellular matrix is facilitated by a variety of cell surface-associated proteolytic pathways and enzymes including: Matrix metalloproteinases (MMPs), cysteine proteases including cathepsins B and L, aspartic protease cathepsin D, and serine proteases that include plasmin and urokinase (uPA) (Lakka et al., 2005) as well as PI 3'-kinase/Akt/IKK-mediated signaling pathways Das, R., G. H. Mahabeleshwar, and G. C. Kundu, *J Biol Chem*, 2004. 279(12): p. 11051-64; Das, R., et al., *IUBMB Life*, 2005. 57(6): p. 441-7).

Accordingly, a reduction in $pH_i$ has been associated with reduced rates of proliferation and growth arrest in transformed cell types (Musgrove et al., *Exp. Cell Res.*, 172:65-75 (1987); Rotin et al., *Cancer Res.*, 49:205-211 (1989); Horvat et al., *Eur. J. Cancer*, 29A:132-217 (1992)). The inhibitory effect of a reduction in on tumor cell proliferation is thought to be primarily due to the glycolytic enzyme phosphofructokinase (PFK), which has a pH optimum of 7.2 and is the rate limiting step for glycolysis. In addition, hexokinase activity and intracellular distribution are adversely affected by even modest reductions from an optimal alkaline $pH_i$ (Miccoli et al., id), as its activity is required for glucose entry into the glycolytic pathway and is increased in gliomas and in many other proliferative tumors (Katabi et al., *Hum. Gene Ther.*, 10:155-164 (1999); Sebastian et al., *Tumour Biol.*, 19:253-260 (1998)). As such, given the elevated glucose consumption, lactate production, and hypoxic or anoxic environments of malignant gliomas, these tumors may be particularly sensitive to reductions (Erecinska et al., 1995). The alkalosis in glioma cells was reported to result from the persistent activation of NHE1, a ubiquitously-expressed type 1 $Na^+$—$H^+$ exchanger involved in intracellular pH and volume regulation (McLean, L. A., et al. *Am J Physiol Cell Physiol*, 2000. 278(4): p. C676-88, id). Increased NHE1 activity has also been observed in other cancer cell lines, including colon and bladder (Bischof et al., *Biochimica et Biophysica Acta*, 1282:131-139 (1996); Boyer et al., *Cancer Res.*, 52:4441-4447 (1992))

Likewise, inhibition of uPA or uPA-uPAR is associated with marked reductions in tumor proliferation (Lakka, S. S., et al., J Biol Chem, 2005. 280(23): p. 21882-92; Romer et al., 1996; Gondi, C. S., et al. *Cancer Res*, 2004. 64(12): p. 4069-77; Lakka, S. S., et al. *Cancer Res*, 2003. 63(10): p. 2454-61; Gondi, C. S., et al., *Oncogene*, 2003. 22(38): p. 5967-75; Chandrasekar, N., et al., *Oncogene*, 2003. 22(3): p. 392-400) and there is an abundance of evidence that inhibition of uPA/uPAR is effective in the treatment of invasive and metastic cancers, for example, metastatic breast cancer (Amir, S., et al., *Cancer Biol Ther*, 2005. 4(4)), melanoma (Rangaswami, H., A. Bulbule, and G. C. Kundu, *Int J Oncol*, 2006. 28(6): p. 1463-70) and glioma (Mori, T., et al., *J Neurooncol*, 2000. 46(2): p. 115-23; Mohanam, S., et al., *Oncogene*, 2002. 21(51): p. 7824-30; Chandrasekar et al., 2003; Gondi et al., 2003; Mohan, P. M., et al., *Clin Exp Metastasis*, 1999. 17(7): p. 617-21; Lakka et al., 2005) and other tumors (Chorostowska-Wynimko, J., et al., *Mol Cancer Ther*, 2003. 2(1): p. 19-28; Gondi et al., 2003), however it can also alter activation of the AKT, MAPK, or ERK pathways (Lakka et al., 2005; Gandhari et al., 2006). The particular response appears to be cell type-specific, thus while inhibition of uPA/uPAR can cause cellular demise in some cancer cell types, it may not kill normal cells (Koshelnick et al., *J. Biol. Chem.* 1997, 272(45): 28563-7; Tarui et al., *Thromb Haemost*, 2006, 95(3): 524-34; Gandhari et al., 2006). The ability of uPA to signal through uPAR, but maintain an elevated basal level of activated ERK and inhibit apoptosis represents a novel mechanism whereby the uPA-uPAR system can affect cancer progression in vivo. (Ma et al., *J. Cell Sci.* 2001, 114(Pt 18): 3387-96; Lakka et al., *Int. J. Oncol.* 2001, 18(1): 71-9).

Activation of uPA/uPAR can promote inflammation and target tissue destruction in systemic autoimmune and CNS disorders including multiple sclerosis (MS) (East, E., et al., *Am J Pathol.*, 2005. 167(2): p. 545-54). Clinical studies indicate that the MS drug, glatimer, alters monocyte expression of uPAR in individuals with relapsing and remitting MS (Balabanov, R., et al., *Clin Diagn Lab Immunol.*, 2001. 8(6): p. 1196-203). The urokinase-type plasminogen activator (uPA), in concert with other proteolytic enzymes, also plays a critical role in cartilage degradation during osteoarthritis (Schwab, W. et al., *Histochem Cell Biol.* 2001, 115(4): 317-23) and contributes to the inflammation associated with gouty arthritis (Chu, et al. *J. Rheumatol.* 2006, 33(2): 311-7).

Likewise inhibition of IKKα and IKKβ is associated with reductions in tumor proliferation Affara and Coussens *Cell* 2007, 3: 25-26 Castro et al. recently demonstrated that 6-chloro-8-amino analogs of β-carboline inhibit IkB kinase (IKK) with IC$_{50}$ values as low as 0.10 mM. (Castro, A. C., et al., *Bioorg Med Chem Lett*, 2003. 13(14): p. 2419-22) 8-Amido analogs specifically inhibit IKK while being essentially inactive (IC$_{50}$s>25 mM) against PKA, PKC, and CKII.

Amiloride (3,5-diamino-6-chloro-N-(diaminomethylene) pyrazinecarboxamide), originally developed as an antidiuretic drug, displays antiproliferative effects on several cancer cell lines (Horvat et al., id; Hasuda et al., id; García-Cañero et al., *Tox. Letters*, 106:215-228 (1999); Wong et al., *Brit. J. Cancer*, 87:238-245 (2002)), including glioma cells (Szolgay-Daniel et al., *Cancer Res.*, 51:1039-1044 (1991)) through inhibition of specific ion transport systems; in particular, amiloride displays inhibitory activity toward several classes of Na$^+$-dependent membrane transporters, including NHE1, NCX (a Na$^+$—Ca$^{2+}$ exchanger), the Na$^+$/K$^+$-ATPase, Na$^+$-coupled solute transport, voltage-gated Na$^+$ channels, etc. However, the hydrophobic nature of amiloride, its weak inhibitory activity toward transporters such as NHE1, and its inability to cross the blood brain barrier (BBB) make it unsuitable as an effective drug for treating cancers such as gliomas. In addition to amiloride, various amiloride derivatives have been synthesized, however, such amiloride derivatives are also unsuitable as effective drugs for cancer therapy due to their non-specificity, toxicity, and/or inability to access the central nervous system (i.e., cross the BBB). Although conjugation of alkyl, alkenyl, or benzyl moieties to either the C(2) guanidine group or the C(5) amino group of amiloride has been reported to increase the inhibitory efficacy of NHE1 and/or other ion transporters (e.g., NCX) (L'Allemain et al., *J. Biol. Chem.*, 259:4313-4319 (1984); Frelin et al., *Biochimie*, 70:1285-1290 (1988)), these derivatives suffer from the same disadvantages as amiloride (e.g., non-specificity, toxicity, and/or inability to access the central nervous system). For example, a benzyl derivative of amiloride, 2,4-dichlorobenzamil (DCB), is highly toxic and causes lethality when administered.

The present invention avoids these problems by providing inactive prodrugs of amiloride analogs which permeate eukaryotic cells and become activated following cleavage by intracellular uPA in cancer cells. The activated, hydrophilic drugs are trapped within the cell resulting in their accumulation. The compounds of the present invention have been designed to selectively inhibit intracellular uPA, IKKβ of the NFκB pathway, and/or other intracellular kinases that activate the signaling pathways regulating the transcription of uPA, osteopontin, SPARC or the gelatinases (FIG. 1A). The compounds and methods of the present invention (1) target particular cells and/or tissues with high specificity and potency, for example, by generating a high concentration of active compounds within the tumor cells; (2) are low in toxicity and side-effects to non-targeted cells and/or tissues; (3) are able to be transported across the BBB to access the central nervous system; and (4) kill tumor cell populations residing in hypoxic-ischemic tumor microenvironments that are normally resistant to conventional chemotherapy or radiotherapy.

In addition, administration of the compounds of the present invention allowing for activation by inflammatory cells expressing intracellular uPA are useful in reducing the inflammatory component of CNS autoimmune disorders, such as osteoarthritis, rheumatoid arthritis and progressive multiple sclerosis.

BRIEF SUMMARY OF THE INVENTION

The present invention provides novel amiloride conjugates and methods of use thereof. The amiloride conjugates exhibit high specificity and potency, low toxicity, and are transported across the BBB and into cells in the central nervous system. For example, the amiloride conjugates are activated by uPA in the malignant cells to release uPA inhibitors that inhibit components of the signaling pathways that contribute to cell survival and proliferation. Examples include upstream signaling components regulating uPA through osteopontin/integrin, complexation of uPA receptor or receptor tyrosine kinase pathway. In particular, the amiloride conjugates of the present invention have the following advantages:

(1) amiloride-peptide conjugates with peptidase cleavage sites are not only capable of traversing the BBB, but upon cleavage by brain- or tumor-specific peptidases, such as urokinase plasminogen activator (uPA) in the central nervous system, release hydrophilic proteolytic products (e.g., C(2)-amidine-AmC(5)-Gly, AmC(5)-Gly) that are uPA inhibitors and are trapped within the tumor cells due to their increased hydrophilicity, and act at the tumor cell surface, thus increasing the potency;

(2) a pulse administration of the hydrophobic prodrug allows the realization of micromolar potencies of enzymatically-activated and selective uPA inhibitors, thus minimizing toxicity and side-effects;

(3) the conjugates kill hypoxic-ischemic tumor cells (i.e., tumor cells with little or no blood supply) that are not normally killed by conventional therapy; and (4) following pulse administration of the amiloride conjugates, the compounds still in prodrug form (i.e., unactivated) egress from normal cells, but the activated, hydrophilic uPA inhibitors remain trapped within uPA-expressing malignant cells or inflammatory cells to impair secretion of uPA, which, in turn, prevents uPA-mediated destruction of the extracellular matrix.

In view of the above, the present invention provides, in one aspect, methods of treating cancers, particularly gliomas, breast, prostate and lung cancers, by administering to a subject in need of such treatment, a compound having the formula Ia:

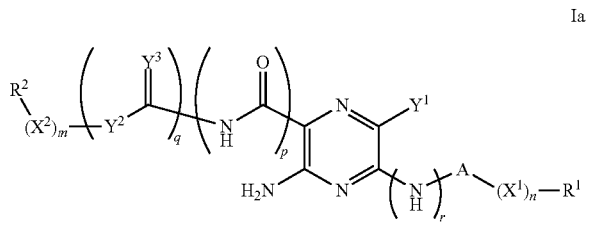

wherein the subscripts n, m, p, q and r, and the variables R$^1$, R$^2$, X$^1$, X$^2$, Y$^1$, Y$^2$, Y$^3$, and A are as provided below in the Detailed Description. Selected embodiments use compounds are provided below under Formula II, IIa, IIb, IId, IIe, IIf, IIj and IIk.

In another aspect, the present invention provides compounds of formula I:

$$D-X-R \qquad \qquad I$$

wherein

D is an inhibitor of urokinase plasminogen activator (uPA), such as an inhibitor of intracellular uPA;

X— is peptidyl substrate of urokinase plasminogen activator (uPA) covalently attached to D and R, such as via an amide linkage;

R is a hydrophobic moiety or an additional therapeutic or diagnostic agent; and pharmaceutically acceptable derivatives thereof.

In yet another aspect, the present invention provides compounds having formula I, Ia, and II (as provided above and in the Detailed Description) which are other than Arm-C(5)-Gly, Am-C(5)-Gly-OBn, Am-C(5)-Gly-D-Ala-Gly-Phe-D-Leu, Am-C(5)-Gly-D-Ala-Gly-Phe-D-Leu-OBn, Am-C(5)-Gly-Gly-Gly-Phe-Leu, Am-C(5)-Gly-Gly-Gly-Phe-Leu-OBn, Am-C(5)-Gly-Gly-Gly-Gly-Phe-Leu, and Am-C(5)-Gly-Gly-Gly-Gly-Phe-Leu-OBn.

In another aspect, the present invention provides a compound (also referred to as a conjugate) having the formula:

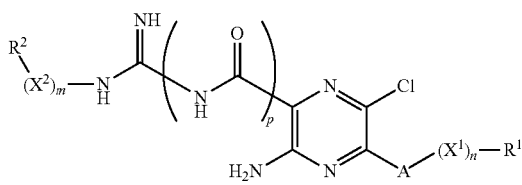

II wherein $R^1$ is selected from the group consisting of hydroxyl; $C_{1-8}$ alkoxy, aryl-$C_{0-8}$alkoxy, heterocyclyl and amino, each of which is optionally substituted with from 1 to 3 substituents each independently selected from the group consisting of $C_{1-8}$ alkyl, aryl-$C_{0-8}$alkyl and heterocyclyl; or a therapeutic agent; $R^2$ is independently selected from the group consisting of H, $C_{1-8}$ alkyl, $C_{0-8}$alkylaryl, carboxy-$C_{1-8}$ alkyl and carboxy $C_{0-8}$alkylaryl; A is an amino acid moiety; p is 0 or 1;
  i) when p is 0;
    —$(X^1)_n$— is a sequence of n independently selected amino acid units, —NH—$R^4$—CO—, attached to A via an amide linkage to the amino terminus of the sequence and to $R^1$ via the carboxy terminus of the sequence, wherein each $R^4$ is independently an optionally substituted alkylene;
    —$(X^2)_m$— is a sequence of m independently selected amino acid units or —NH—$R^4$—CO—, attached to $R^2$ via the amino terminus of the sequence and the rest of the molecule via an amide linkage to the carboxy terminus of the sequence, wherein each $R^4$ is independently an optionally substituted alkylene;
    n is an integer greater than or equal to 0 and less than or equal to 100;
    m is an integer greater than or equal to 0 and less than or equal to 100;
  ii) when p is 1;
    —$(X^1)_n$— is a sequence of n independently selected amino acid units attached to A via an amide linkage to the amino terminus and to $R^1$ via the carboxy terminus of the sequence, and $X^1$ with A can be cleaved with urokinase plasminogen activator (uPA);
    —$(X^2)_m$— is a sequence of m independently selected amino acid units attached to $R^2$ via the amino terminus of the sequence and the rest of the molecule via an amide linkage to the carboxy terminus of the sequence; and $X^2$ can be cleaved with urokinase plasminogen activator (uPA);
    n is an integer greater than or equal to 1;
    m is an integer greater than or equal to 0;
and tautomers and pharmaceutically acceptable derivatives thereof.

In another aspect, the present invention provides methods for inhibiting tumor growth comprising contacting the tumor cells with a prodrug comprising an inhibitor of intracellular urokinase plasminogen activator (uPA) covalently attached to a substrate of intracellular urokinase plasminogen activator (uPA), In yet another aspect, the present invention provides a method for treating or preventing inflammation or cancer, particularly the recurrence of cancer, in a subject in need thereof. The method includes administering to said subject a conjugate of an intracellular urokinase plasminogen activator (uPA) inhibitor and a substrate of intracellular urokinase plasminogen activator (uPA). In one embodiment, the conjugate is administered through pulse administration.

In yet another aspect, the present invention provides a method of generating an intracellular urokinase plasminogen activator (uPA) inhibitor. The method includes contacting a conjugate of an intracellular urokinase plasminogen activator (uPA) inhibitor and a substrate of intracellular urokinase plasminogen activator (uPA) with a urokinase plasminogen activator.

In still another aspect, the present invention provides a method of generating an inhibitor of IKK (NEMO) complex. The method includes contacting a conjugate of an inhibitor of IKK (NEMO) complex and a substrate of intracellular urokinase plasminogen activator (uPA) with urokinase plasminogen activator. In one embodiment, the inhibitor of IKK (NEMO) complex having the formula:

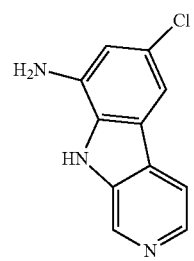

IIi

In a further aspect, the present invention provides methods for administering hydrophobic peptide-drug conjugates that can then be converted in vivo to hydrophilic agents upon the action of a peptidase. In one embodiment, the conjugate is cleaved by intracellular urokinase plasminogen activator (uPA), thereby delivering said inhibitor having the formula:

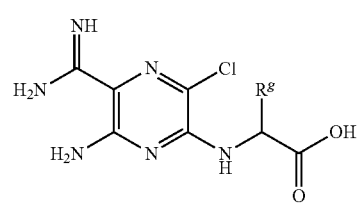

IIg wherein $R^g$ is —H or an amino acid side chain.

In one instance, the conjugate is cleaved by uPA, thereby delivering said inhibitor having the formula:

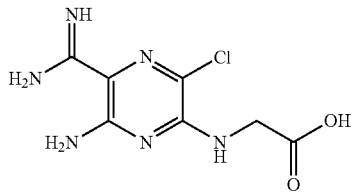

IIg₁

In another embodiment, the conjugate is cleaved by intracellular urokinase (uPA), thereby delivering an inhibitor having the formula:

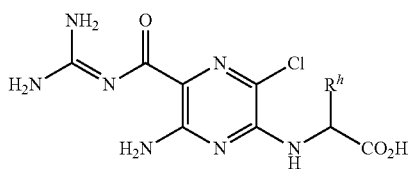

IIh wherein $R^h$ is —H or an amino acid side chain.
In one instance, the conjugate is cleaved by uPA, thereby delivering said inhibitor having the formula:

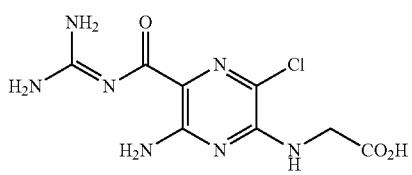

IIh₁

Other objects, features, and advantages of the present invention will be apparent to one of skill in the art from the following detailed description and figures.

BRIEF DESCRIPTION OF THE DRAWINGS

FIG. 4 illustrates the inhibition of glioma attachment to ECM by AmC(5)GlyOBn.

FIG. 6 illustrates that establishment and local invasion of Intracerebral Glioma xenografts are prevented or retarded by intracranial administration of AmC(5)-GlyOBn. FIG. 6A: Tumor growth over a period of 3-4 weeks. FIG. 6B: Intracerebral U87 xenograft tumor growth kinetics in athymic rats. FIG. 6C: U87Glioma volumes determined by MRI. FIG. 6D: Gloma xenograft mean volume.

FIG. 10 illustrates the partition coefficient measurement.

FIG. 11 illustrates the mean tumor volumes of AmC(5)-GlyOBn treated and untreated animals.

FIG. 12 provides a table of representative data for compounds described herein that illustrates the selectivity and activity associated with certain embodiments.

DETAILED DESCRIPTION OF THE INVENTION

I. Definitions

Figure 1A:
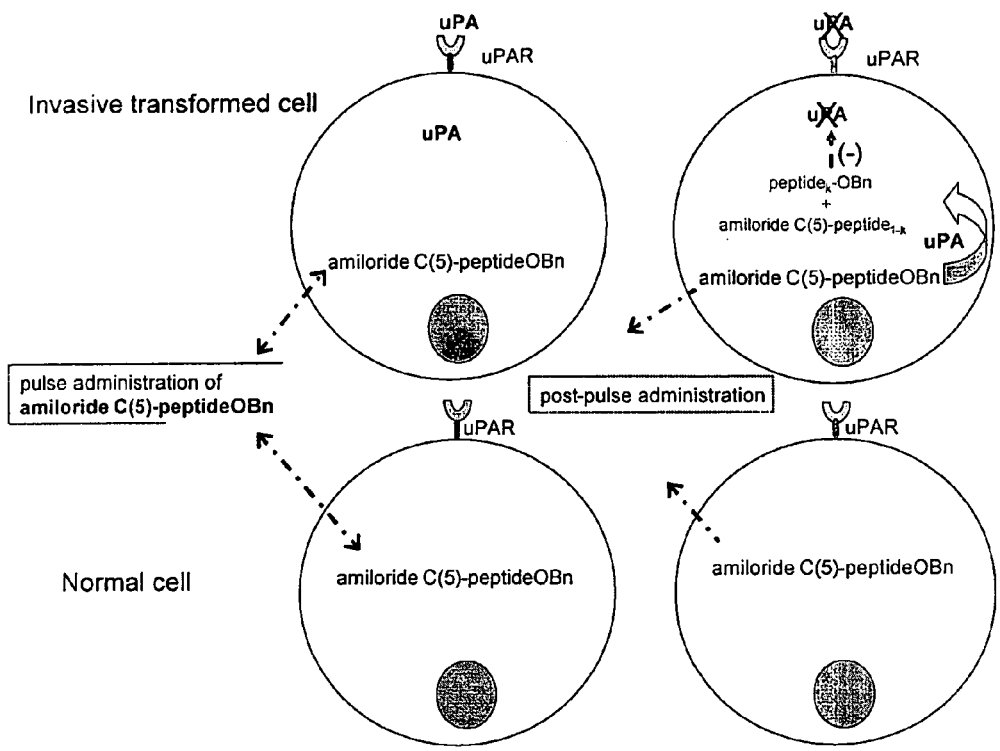
FIG. 1A illustrates a model for tumor cell death induced by the amiloride conjugates of the present invention. Administration of a hydrophobic, substituted peptide conjugate of amiloride, e.g. AmC(5)-(peptide)$_n$R, permeates cells. The inactive peptide conjugate is activated following endopeptidase cleavage by uPA. The hydrophilic peptide conjugate of accumulates within the cell where it inhibits uPA. Extracellular uPA bound to uPAR can also cleave inactive amiloride peptide prodrug generating a compound that inhibits extracellular uPA or IKK.

As used herein, the following terms have the meanings ascribed to them unless specified otherwise.

The term "conjugate" refers to a chemical compound that has been formed by the joining or attachment of two or more compounds. In particular, a conjugate of the present invention comprises an amino acid or peptide covalently attached to amiloride or other suitable therapeutic agent, such as heteroaromatic carboxamidines.

The term "alkyl" refers to a linear, branched, or cyclic saturated monovalent hydrocarbon unit or a combination of cyclic and linear or branched saturated monovalent hydrocarbon units having the number of carbon atoms indicated in the prefix. For example, $(C_1-C_8)$alkyl is meant to include methyl, ethyl, n-propyl, 2-propyl, tert-butyl, pentyl, cyclopentyl, cyclopropylmethyl and the like.

The term "alkoxy," is used in its conventional sense, and refers to those alkyl groups attached to the remainder of the molecule via an oxygen atom.

The term "aryl" means a monovalent monocyclic, bicyclic or polycyclic aromatic hydrocarbon unit of 5 to 10 ring atoms which is unsubstituted or substituted independently with one to four substituents, preferably one, two, or three substituents selected from alkyl, cycloalkyl, cycloalkyl-alkyl, halo, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkyl-alkyl, phenyl or phenylalkyl, aryl or arylalkyl), —(CR'R")$_n$—COOR (where n is an integer from 0 to 5, R' and R" are independently hydrogen or alkyl, and R is hydrogen, alkyl, cycloalkyl, cycloalkylalkyl cut, phenyl or phenylalkyl aryl or arylalkyl) or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl, aryl or arylalkyl). More specifically the term aryl includes, but is not limited to, phenyl, biphenyl, 1-naphthyl, and 2-naphthyl, and the substituted forms thereof.

The term "alkylene" means a linear saturated divalent hydrocarbon spacer or linker or a branched saturated divalent hydrocarbon unit. For example, (C$_1$-C$_6$)alkylene is meant to include methylene, ethylene, propylene, 2-methylpropylene, pentylene, and the like. For embodiments in which the number of carbon atoms is not designated, the term is meant to include those having from one to eight carbon atoms, more preferably from one to four carbon atoms.

Substituents for the alkyl, alkylene and aryl can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to four, preferably, zero, one, two or three substituents. R', R" and R'" each independently refer to hydrogen, unsubstituted (C$_1$-C$_8$)alkyl and heteroalkyl, unsubstituted aryl, aryl substituted with 1-3 halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "substituted alkyl" in its broadest sense is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). In some embodiments, the alkyl groups will have from 0-3 substituents, more preferably 0, 1, or 2 substituents, unless otherwise specified.

The term "therapeutic agent" is used in its conventional sense and refers to an gent having or exhibiting healing powers. For example, the therapeutic agents as used herein include, but are not limited to, agents for treating and/or preventing brain tumors, prostate, lung and breast cancers and etc; inflammatory disorders, such as osteoarthritis, rheumatoid arthritis, progressive multiple sclerosis and etc.

The term "amino acid" refers to naturally occurring α-amino acids and their stereoisomers, as well as unnatural amino acids such as amino acid analogs, amino acid mimetics, synthetic amino acids, β-amino acids, γ-amino acids, N-methyl amino acids, and N-substituted glycines in either the L- or D-configuration that function in a manner similar to the naturally occurring amino acids. Naturally occurring amino acids are those encoded by the genetic code, as well as those amino acids that are later modified, e.g., hydroxyproline, carboxyglutamate, and O-phosphoserine. "Stereoisomers" of naturally occurring amino acids refers to mirror image isomers of the naturally occurring amino acids, such as D-amino acids. "Amino acid analogs" refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. In β-amino acids, the amino group is bonded to the β-carbon atom of the carboxyl group such that there are two carbon atoms between the amino and carboxyl groups. In γ-amino acids, the amino group is bonded to the γ-carbon atom of the carboxyl group such that there are three carbon atoms between the amino and carboxyl groups. Suitable side chains (e.g., R groups) for β- or γ-amino acids include, but are not limited to, side chains present in naturally occurring amino acids and unnatural amino acids such as amino acid analogs, amino acid mimetics, synthetic amino acids, N-methyl amino acids, and N-substituted glycines.

The term "N-substituted glycine" refers to a glycine amino acid where an amino acid side chain is attached to the glycine nitrogen atom. Suitable amino acid side chains (e.g., R groups) include, but are not limited to, side chains present in naturally occurring amino acids and side chains present in unnatural amino acids such as amino acid analogs, amino acid mimetics, synthetic amino acids, β-amino acids, and γ-amino acids. Examples of N-substituted glycines suitable for use in the present invention include, without limitation, N-(2-aminoethyl)glycine, N-(3-aminopropyl)glycine, N-(2-methoxyethyl)glycine, N-benzylglycine, (S)-N-(1-phenylethyl)glycine, N-cyclohexylmethylglycine, N-(2-phenylethyl)glycine, N-(3-phenylpropyl)glycine, N-(6-aminogalactosyl)glycine, N-(2-(3'-indolylethyl)glycine, N-(2-(p-methoxyphenylethyl))glycine, N-(2-(3'-chlorophenylethyl)glycine, and N-[2-(p-hydroxyphenylethyl)]glycine. Such N-substituted glycines can have an L- or D-configuration. N-substituted glycine oligomers, referred to herein as "peptoids," have been shown to be protease resistant (Miller et al., *Drug Dev. Res.*, 35:20-32 (1995)). As such, an amiloride-peptoid conjugate is within the scope of the present invention.

Amino acids may be referred to herein by either their commonly known three letter symbols or by the one-letter symbols recommended by the IUPAC-IUB Biochemical Nomenclature Commission. D-amino acids are represented herein by a lower-case one-letter amino acid symbol (e.g., r for D-arginine), whereas L-amino acids are represented by an upper case one-letter amino acid symbol (e.g., R for L-arginine).

With respect to amino acid sequences, one of skill will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acids include, but are not limited to, naturally occurring amino acids such as α-amino acids having an L-configuration, stereoisomers of naturally occurring amino acids such as α-amino acids having a D-configuration, and unnatural amino acids such as amino acid analogs, amino acid mimetics, synthetic amino acids, β-amino acids, and γ-amino acids, in either the L- or D-configuration. For example, the unnatural amino acids of Liu and Lam (*Anal. Biochem.*, 295:9-16 (2001)) are suitable for use in the present invention.

Conservative substitution tables providing functionally similar amino acids are well known in the art. For example, substitutions may be made wherein an aliphatic amino acid (G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, E or D, may be substituted with its uncharged counterpart, Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins*, 1984).

The term "peptide" refers to a compound made up of a single chain of D- or L-amino acids or a mixture of D- and L-amino acids joined by peptide bonds. Generally, peptides are about 2 to about 50 amino acids in length. Amino acids or peptides conjugated to the amino group at C5 position of amiloride is designated AmC(5)-aa or AmC(5)-peptide. Amiloride, when conjugated to an amino acid in the C5 position, functions as a pseudo-amino acid positioned at the N-terminus of the peptide chain. Preferably, the peptides of the present invention are conjugated via a peptide bond to the C(2) and/or C(5) glycine of C2am-Gly or C5am-Gly. However, the peptides can also be directly conjugated to the C(2) and/or C(5) position of amiloride (e.g., no glycine spacer.) The peptides of the present invention are preferably between 2 and 25 amino acids, more preferably between 2 and 10 amino acids, and most preferably between 2 and 8 amino acids in length. In a particularly preferred embodiment, the free amino-terminus and/or carboxyl-terminus on peptides are protected by an amide, a methyl ester, a succinyl, a benzyl ester or an acetyl group.

The terms "linker" and "spacer" are used interchangeably herein to refer to an amino acid or a doubly functionalized hydrocarbon chain that connects a peptide or an active pharmaceutical compound to the C(2) and/or C(5) position of amiloride. Preferably, the amino acid linker on amiloride is glycine, e.g., C2am-Gly, C5am-Gly, or C2,5am-(Gly)$_2$. Preferably, the doubly functionalized hydrocarbon chain on amiloride is a diamine, e.g., NH$_2$—(CH$_2$)$_n$—NH$_2$, wherein n is from 1 to 6. Preferably, the peptide connected to amiloride via a linker is selectively cleaved by a peptidase. Preferably, the active pharmaceutical compound connected to amiloride via a linker is tamoxifen, e.g., for breast cancer therapy.

The term "tautomer" means compounds produced by the phenomenon wherein a proton of one atom of a molecule shifts to another atom. See, Jerry March, Advanced Organic Chemistry: Reactions, Mechanisms and Structures, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol and the like, ring-chain tautomers, such as glucose/2,3,4,5,6-pentahydroxy-hexanal and the like. The compounds described herein may have one or more tautomers and therefore include various isomers. All such isomeric forms of these compounds are expressly included in the present invention.

The term "pharmaceutically acceptable derivative" includes, but are not limited to, salts, prodrug conjugates such as esters and amides, metabolites, hydrates, solvates and the like.

The terms "heterocyclyl" refers to a saturated or unsaturated non-aromatic cyclic group containing at least one sulfur, nitrogen or oxygen heteroatom. Each heterocycle can be attached at any available ring carbon or heteroatom. Each heterocycle may have one ("heteromonocyclyl") or more rings (e.g. "heterobicyclyl"). When multiple rings are present, they can be fused together or linked covalently. Each heterocycle must contain at least one heteroatom (typically 1 to 5 heteroatoms) selected from nitrogen, oxygen or sulfur.

The term "cancer" refers to any of various malignant neoplasms characterized by the proliferation of anaplastic cells that tend to invade surrounding tissue and metastasize to new body sites. Examples of different types of cancer suitable for treatment using the present invention include, but are not limited to, lung cancer, breast cancer, prostate cancer, bladder cancer, thyroid cancer, liver cancer, pleural cancer, pancreatic cancer, ovarian cancer, cervical cancer, testicular cancer, colon cancer, B-cell lymphoma, non-Hodgkin's lymphoma, Burkitt's lymphoma, fibrosarcoma, neuroblastoma, glioma, melanoma, monocytic leukemia, and myelogenous leukemia.

The term "peptidase" refers to any of various enzymes that catalyze the degradation of peptides, polypeptides, and proteins by hydrolyzing at least one of their peptide bonds. Suitable peptidases for use in the present invention include, but are not limited to, endopeptidases (e.g., serine proteases and metalloproteinases) and exopeptidases (e.g., carboxypeptidases and aminopeptidases). Preferably, the peptidase is an endopeptidase. In particular, endopeptidases such as enkephalinases, matrix metalloproteinases, calpains, and caspases are suitable for use in the present invention.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "selectively cleaved" refers to the hydrolysis of a peptide bond by a protease upon recognition of a specific amino acid residue or amino acid sequence in a peptide, polypeptide, or protein. For example, trypsin selectively cleaves peptide bonds on the carboxyl-terminal side of lysine (K) and arginine (R) amino acid residues. Chymotrypsin selectively cleaves peptide bonds on the carboxyl-terminal side of phenylalanine (F), tryptophan (W), and tyrosine (Y) residues. Enkephalinase selectively cleaves peptide bonds on the amino-terminal side of hydrophobic residues.

As used herein, "administering" means oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

II. General Overview

The present invention provides novel amiloride conjugates and methods of administering thereof that advantageously display high specificity and potency, low toxicity, reduced potential side-effects, and transport across the blood brain barrier (BBB) into cells of the central nervous system. Specifically, the amiloride conjugates of the present invention block extracellular uPA-uPAR interactions in inflammatory and cancer cells. The intracellular trapping of the activated uPA inhibitor in micromolar to millimolar concentrations results in a reduction of undesirable side-effects.

Amiloride is an FDA-approved diuretic that inhibits tumor cell proliferation and exhibits cytotoxic effects on tumor cells at high concentrations. However, due to the hydrophobic nature of amiloride (i.e., high toxicity associated with significant intracellular accumulation), its low potency for producing cytotoxic effects (i.e., high (≥500 μM) concentrations required), and its inability to cross the blood brain barrier (BBB), amiloride is unsuitable as an effective drug for treating cancers such as gliomas. By contrast, the present invention provides novel amino acid and peptide conjugates of amiloride that are potent and effective NHE1, NCX, uPa and/or IKK NEMO inhibitors, display cytotoxic and/or anti-proliferative effects on tumor cells such as glioma cells, are able to cross the BBB and are selectively cleaved by brain- or tumor-specific peptidases, such as uPA.

In particular, the amiloride conjugates of the present invention have the following advantages. Thus in one advantage, (1) amiloride-peptide conjugates with peptidase cleavage sites are not only capable of traversing the BBB, but upon cleavage by brain- or tumor-specific peptidases, such as uPA in the central nervous system, release hydrophilic proteolytic products (e.g., C(2)amidine-AmC(5)-Gly, C(5)Am-Gly) that are uPA inhibitors and are trapped within the tumor cells due to their increased hydrophilicity and accumulate intracellularly, and act at the tumor cell surface, thus minimizing toxic side effects. In another advantage (2), the present invention permits the realization of micromolar potencies of unactivated and selective uPA inhibitors through pulse administration, thus minimizing toxicity and side-effects. In another advantage (3), the conjugates kill tumor cell populations residing in hypoxic-ischemic tumor microenvironments (i.e., tumor cells with little or no blood supply) that are normally resistant to conventional chemotherapy or radiotherapy. In another advantage (4), following pulse administration of the amiloride conjugates, the compounds still in prodrug form (i.e., unactivated) egress from normal cells, but the activated, hydrophilic uPA inhibitors remain trapped within uPA-expressing malignant cells or inflammatory cells to impair secretion of uPA, which, in turn, prevents uPA-mediated destruction of the extracellular matrix. In another advantage (5), the uPA activation mechanism can be used to liberate compounds that inhibit components of the signaling pathways that contribute to cell survival and proliferation e.g. upstream signaling components regulating uPA through osteopontin/integrin, complexation of uPA receptor, or receptor tyrosine kinase pathways.

These unique features make the amiloride conjugates of the present invention particularly useful therapeutic agents for the treatment of cancer (e.g., glioma, lung, breast and prostate cancer) as well as other diseases and disorders such as central nervous system disorders (e.g., traumatic brain injury, seizure), stroke, cardiac arrthymia, etc. For example, the amiloride conjugates of the present invention are useful as antiinflammatory agents to prevent invasion, proliferation of sensitized inflammatory cells that synthesize and urokinase plasminogen activator factor, or overexpress osteopontin or gelatinases. Human disorders include, but are not limited to: osteoarthritis, Sjogrens syndrome, rheumatoid arthritis, systemic lupus erythrematosis, multiple sclerosis, post-traumatic brain injury, inflammatory brain disorders (encephalitis, cerebritis, arachnoiditis). Moreover, amiloride conjugates of the present invention are also useful for preventing invasion, metastasis, and proliferation of cancer cells that synthesize urokinase plasminogen activator factor, or overexpress osteopontin or gelatinases. Human disorders include, but are not limited to: prostate, lung, breast, primordial neuroectodermal tumors, brain tumors.

III. Description of the Embodiments

Methods of Treating Cancers

The present invention is directed to methods of treating cancers, particularly gliomas, breast, prostate and lung cancers. In some of the most preferred embodiments, the invention is directed to methods for the treatment of a glioma, by administering to a subject in need of such treatment, a compound having the formula Ia:

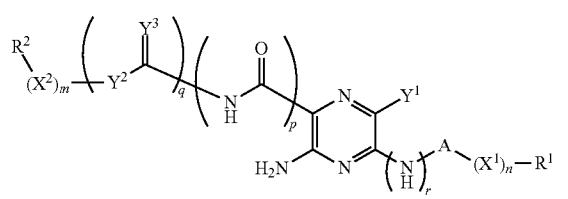

Ia wherein $Y^1$ is H or Cl; $Y^2$ is NH or O; $Y^3$ is NH or N—OH; $R^2$ is independently selected from the group consisting of H, $C_{1-8}$ alkyl, $C_{0-8}$alkylaryl, carboxy-$C_{1-8}$ alkyl and carboxy$C_{0-8}$alkylaryl—for example, benzyloxycarbonyl; A is an amino acid moiety, <—NH—CHR$^3$—CO—>, wherein $R^3$ indicates an amino acid side chain, —> and <— indicate the attachment sites to $X^1$ or $R^1$ and the rest of the molecule; p is 0 or 1; q is 0 or 1, and at least one of p and q is 1; r is 0 or 1; n is an integer of from 0 to 100, preferably 2 to 8; m is an integer of from 0 to 100, preferably 2 to 8; and i) when p is 0; and r is 0;
—(X$^1$)$_n$— is a sequence of n independently selected amino acid units, —NH—R$^4$—CO—, attached to A via an amide linkage to the amino terminus of the sequence and to R$^1$ via the carboxy terminus of the sequence, wherein each R$^4$ is independently an optionally substituted alkylene;

$R^1$ is selected from the group consisting of $C_{1-8}$ alkoxy, aryl-$C_{0-8}$alkoxy, heterocyclyl and amino, each of which is optionally substituted with from 1 to 3 substituents each independently selected from the group consisting of $C_{1-8}$ alkyl, aryl-$C_{0-8}$alkyl and heterocyclyl; or a therapeutic agent; and —$(X^2)_m$— is a sequence of m independently selected amino acid units, —NH—$R^4$—CO—, attached to $R^2$ via the amino terminus of the sequence and the rest of the molecule via an amide linkage to the carboxy terminus of the sequence, wherein each $R^4$ is independently an optionally substituted alkylene or $C_{3-7}$ cycloalkylene;

ii) when p is 1; r is 0;

—$(X^1)_n$— is a sequence of n independently selected amino acid units attached to A via an amide linkage to the amino terminus and to $R^1$ via the carboxy terminus of the sequence; and $X^1$ with A can be cleaved with urokinase plasminogen activator (uPA);

$R^1$ is selected from the group consisting of H, $C_{1-8}$ alkoxy, aryl-$C_{0-8}$alkoxy, heterocyclyl and amino, each of which is optionally substituted with from 1 to 3 substituents each independently selected from the group consisting of $C_{1-8}$ alkyl, aryl-$C_{0-8}$alkyl and heterocyclyl; or a therapeutic agent; and —$(X^2)_m$— is a sequence of m independently selected amino acid units attached to $R^2$ via the amino terminus of the sequence and the rest of the molecule via an amide linkage to the carboxy terminus of the sequence; and $X^2$ can be cleaved with urokinase plasminogen activator (uPA);

iii) when r is 1;

A is an amino acid moiety, <—CO—CHR$^3$—NH—>, wherein $R^3$ indicates an amino acid side chain, —> indicates the attachment sites to $X^1$ or $R^1$ and <— indicates the attachment site to —(NH)$_r$—;

—$(X^1)_n$— is a sequence of n independently selected amino acid units attached to A via an amide linkage to the carboxy terminus and to $R^1$ via the amino terminus of the sequence; and $X^1$ with A can be cleaved with urokinase plasminogen activator (uPA);

$R^1$ is H, $C_{1-8}$ alkyl or an amino protecting group;

—$(X^2)_m$— is a sequence of m independently selected amino acid units attached to $R^2$ via the amino terminus of the sequence and the rest of the molecule via an amide linkage to the carboxy terminus of the sequence; and $X^2$ can be cleaved with urokinase plasminogen activator (uPA);

and tautomers and pharmaceutically acceptable derivatives thereof.

In one group of embodiments, the methods are conducted using compounds of formula Ia in which the subscript r is 1. Within this group of embodiments are those in which p is 1; q is 1; $Y^2$ is NH; m is 0; $R^2$ is H; $Y^3$ is H; and the portion represented by -A-$(X^1)_n$—$R^1$ is peptide attached to —(NH)$_r$— by an amide linkage to the carboxy terminus and is selected from the group consisting of -Gly-Arg-Gly-Gly-$R^1$, -Gly-Gly-Gly-Arg-Gly-$R^1$, -Val-Gly-Arg-Gly-$R^1$, -Val-Gly-Arg-Gly-Gly-$R^1$, -Gly-Val-Gly-Arg-Gly-$R^1$, -Val-Leu-Lys-Gly-$R^1$, -Val-Leu-Lys-Gly-Gly-$R^1$, and -Gly-Val-Leu-Lys-Gly-$R^1$.

In still other embodiments, the methods use compounds of formula Ia, wherein the subscripts r and p are each 0, and $Y^1$ is H. In yet other embodiments, methods using compounds of formula Ia, are those in which the subscripts r and p are each 0; $Y^2$ is O; and $R^2$ is selected from the group consisting of $C_{1-8}$ alkyl, $C_{0-8}$alkylaryl, carboxy-$C_{1-8}$ alkyl and carboxy$C_{0-8}$alkylaryl.

Selected embodiments include those in which the compound (or conjugate) being administered has formula II:

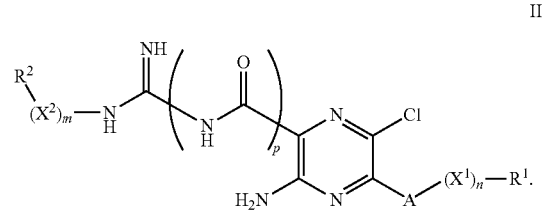

II

In one group of embodiments, the subscript p is 0. In other embodiments, p is 0 and n is 0. In still other embodiments, p is 0 and m is 0.

In yet another group of embodiments, the compound being administered is a compound of formula II, wherein p is 1; the portion represented by -A-$(X^1)_n$—$R^1$ is —NHCH$_2$CO$_2$H or —NHCH$_2$CO$_2$CH$_2$Ph; and the portion represented by $R^2$—$(X^2)_m$— is selected from the group consisting of benzyloxycarbonyl-Gly-Gly-Arg-, benzyloxycarbonyl-Val-Gly-Arg-, and benzyloxycarbonyl-Val-Leu-Lys-.

In a related group of embodiments, the compound being administered has the formula:

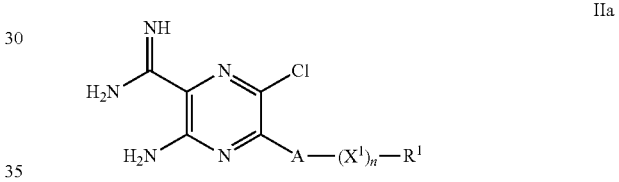

IIa

Within this group of embodiments, certain preferred embodiments are those in which the portion represented by -A-$(X^1)_n$—$R^1$ is selected from the group consisting of -Gly-Gly-Arg-Gly-OCH$_2$Ph, -Gly-Gly-Gly-Arg-Gly-OCH$_2$Ph, -Val-Gly-Arg-Gly-OCH$_2$Ph, -Val-Gly-Arg-Gly-Gly-OCH$_2$Ph, -Gly-Val-Gly-Arg-Gly-OCH$_2$Ph, -Val-Leu-Lys-Gly-OCH$_2$Ph, -Val-Leu-Lys-Gly-Gly-OCH$_2$Ph, and -Gly-Val-Leu-Lys-Gly-OCH$_2$Ph. In another embodiment, the portion represented by -A-$(X^1)_n$—$R^1$ is -Gly-OCH$_2$Ph.

In another group of embodiments, the compounds of formula Ia and formula II used in the various treatment methods herein are those in which —$(X^2)_m$— or —$(X^1)_n$—, alone or combined with A, is selectively is cleaved by intracellular urokinase plasminogen activator (uPA).

Returning to formula II, in another group of embodiments, p is 1. In other embodiments, p is 1 and n is 0. In still other embodiments, p is 1 and m is 0. In other embodiments, the compounds have formula IIb:

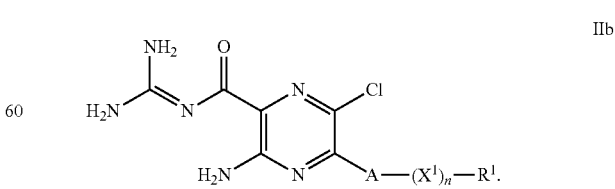

IIb

Certain preferred compounds of formula IIb are those in which the portion represented by -A-$(X^1)_n$—$R^1$ is selected from the group consisting of -Gly-Gly-Arg-Gly-OCH$_2$Ph, -Gly-Gly-Gly-Arg-Gly-OCH$_2$Ph, -Val-Gly-Arg-Gly-OCH$_2$Ph, -Val-Gly-Arg-Gly-Gly-OCH$_2$Ph, -Gly-Val-Gly-Arg-Gly-OCH$_2$Ph, -Val-Leu-Lys-Gly-OCH$_2$Ph, -Val-Leu-Lys-Gly-Gly-OCH$_2$Ph, and -Gly-Val-Leu-Lys-Gly-OCH$_2$Ph. In another embodiment, the compound of formula IIb is the compound wherein the portion represented by -A-(X$^1$)$_n$—R$^1$ is -Gly-OCH$_2$Ph.

Conjugates

In addition to the methods described above, the present invention is also directed to certain novel compounds that are useful in those methods. In general, the compounds are represented by formula I:

$$D\text{-}X\text{—}R \qquad I$$

wherein
D is an inhibitor of intracellular urokinase plasminogen activator (uPA);
X— is peptidyl substrate of urokinase plasminogen activator (uPA) attached to D and R via an amide linkage;
R is a hydrophobic moiety or an additional therapeutic or diagnostic agent;
and pharmaceutically acceptable derivatives thereof.

More particularly, the compounds are those of formula Ia:

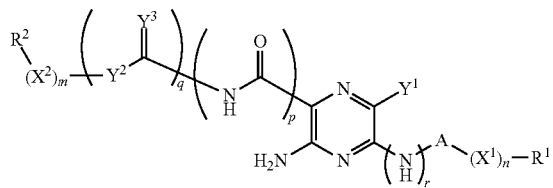

Ia wherein Y$^1$ is H or Cl; Y$^2$ is NH or O; Y$^3$ is NH or N—OH; R$^2$ is independently selected from the group consisting of H, C$_{1-8}$ alkyl, C$_{0-8}$ alkylaryl, carboxy-C$_{1-8}$ alkyl and carboxyC$_{0-8}$alkylaryl—for example, benzyloxycarbonyl; A is an amino acid moiety, <—NH—CHR$^3$—CO—>, wherein R$^3$ indicates an amino acid side chain, —> and <— indicate the attachment sites to X$^1$ or R$^1$ and the rest of the molecule; p is 0 or 1; q is 0 or 1, and at least one of p and q is 1; r is 0 or 1; n is an integer of from 0 to 100, preferably 2 to 8; m is an integer of from 0 to 100, preferably 2 to 8; and i) when p is 0; and r is 0;
—(X$^1$)$_n$— is a sequence of n independently selected amino acid units, —NH—R$^4$—CO—, attached to A via an amide linkage to the amino terminus of the sequence and to R$^1$ via the carboxy terminus of the sequence, wherein each R$^4$ is independently an optionally substituted alkylene;
R$^1$ is selected from the group consisting of C$_{1-8}$ alkoxy, aryl-C$_{0-8}$alkoxy, heterocyclyl and amino, each of which is optionally substituted with from 1 to 3 substituents each independently selected from the group consisting of C$_{1-8}$ alkyl, aryl-C$_{0-8}$alkyl and heterocyclyl; or a therapeutic agent; and
—(X$^2$)$_m$— is a sequence of m independently selected amino acid units, —NH—R$^4$—CO—, attached to R$^2$ via the amino terminus of the sequence and the rest of the molecule via an amide linkage to the carboxy terminus of the sequence, wherein each R$^4$ is independently an optionally substituted alkylene or C$_{3-7}$ cycloalkylene;

ii) when p is 1; r is 0;
—(X$^1$)$_n$— is a sequence of n independently selected amino acid units attached to A via an amide linkage to the amino terminus and to R$^1$ via the carboxy terminus of the sequence; and X$^1$ with A can be cleaved with urokinase plasminogen activator (uPA);
R$^1$ is selected from the group consisting of H, C$_{1-8}$ alkoxy, aryl-C$_{0-8}$alkoxy, heterocyclyl and amino, each of which is optionally substituted with from 1 to 3 substituents each independently selected from the group consisting of C$_{1-8}$ alkyl, aryl-C$_{0-8}$alkyl and heterocyclyl; or a therapeutic agent; and
—(X$^2$)$_m$— is a sequence of m independently selected amino acid units attached to R$^2$ via the amino terminus of the sequence and the rest of the molecule via an amide linkage to the carboxy terminus of the sequence; and X$^2$ can be cleaved with urokinase plasminogen activator (uPA);

iii) when r is 1;
A is an amino acid moiety, <—CO—CHR$^3$—NH—>, wherein R$^3$ indicates an amino acid side chain, —> indicates the attachment sites to X$^1$ or R$^1$ and <— indicates the attachment site to —(NH)$_r$—;
—(X$^1$)$_n$— is a sequence of n independently selected amino acid units attached to A via an amide linkage to the carboxy terminus and to R$^1$ via the amino terminus of the sequence; and X$^1$ with A can be cleaved with urokinase plasminogen activator (uPA);
R$^1$ is H, C$_{1-8}$ alkyl or an amino protecting group;
—(X$^2$)$_m$— is a sequence of m independently selected amino acid units attached to R$^2$ via the amino terminus of the sequence and the rest of the molecule via an amide linkage to the carboxy terminus of the sequence; and X$^2$ can be cleaved with urokinase plasminogen activator (uPA);

and tautomers and pharmaceutically acceptable derivatives thereof; wherein the compound is other than: Am-C(5)-Gly, Am-C(5)-Gly-OBn, Am-C(5)-Gly-D-Ala-Gly-Phe-D-Leu, Am-C(5)-Gly-D-Ala-Gly-Phe-D-Leu-OBn, Am-C(5)-Gly-Gly-Gly-Phe-Leu, Am-C(5)-Gly-Gly-Gly-Phe-Leu-OBn, Am-C(5)-Gly-Gly-Gly-Gly-Phe-Leu, and Am-C(5)-Gly-Gly-Gly-Gly-Phe-Leu-OBn. In these notations, Am refers to an amiloride core, C(5) refers to the carbon position (5) in amiloride to which the amino acid or peptide is conjugated. For example, Am-C(5)-Gly-Gly-Gly-Phe-Leu-OBn refers to a compound of the formula:

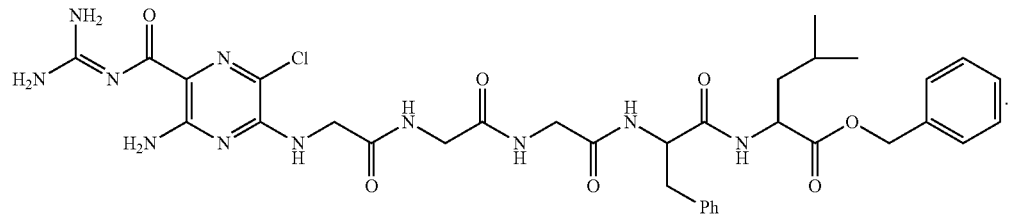 [SMILES: CC(C)CC(NC(=O)C(Cc1ccccc1)NC(=O)CNC(=O)CNC(=O)CNc1nc(N)c(C(=O)N=C(N)N)nc1Cl)C(=O)OCc1ccccc1]

In one group of embodiments, the present invention provides a conjugate having the formula:

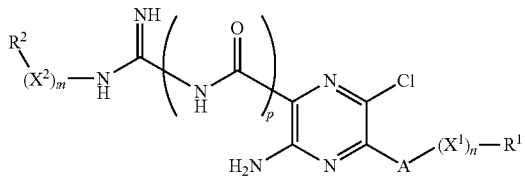

II wherein $R^1$ is selected from the group consisting of hydroxy, $C_{1-8}$ alkoxy, aryl-$C_{0-8}$alkoxy heterocyclyl and amino, each of which is optionally substituted with from 1 to 3 substituents each independently selected from the group consisting of $C_{1-8}$ alkyl, aryl-$C_{0-8}$alkyl and heterocyclyl; or a therapeutic agent; $R^2$ is independently selected from the group consisting of H, $C_{1-8}$ alkyl, $C_{0-8}$alkylaryl, carboxy-$C_{1-8}$ alkyl and carboxy$C_{0-8}$alkylaryl; A is an amino acid moiety; p is 0 or 1; and
  i) when p is 0;
—$(X^1)_n$— is a sequence of n independently selected amino acid units, —NH—$R^4$—CO—, attached to A via an amide linkage to the amino terminus of the sequence and to $R^1$ via the carboxy terminus of the sequence, wherein each $R^4$ is independently an optionally substituted alkylene or cycloalkylene; —$(X^2)_m$— is a sequence of m independently selected amino acid units, —NH—$R^4$—CO—, attached to $R^2$ via the amino terminus of the sequence and the rest of the molecule via an amide linkage to the carboxy terminus of the sequence, wherein each $R^4$ is independently an optionally substituted alkylene or cycloalkylene; n is an integer greater than or equal to 0 and less than or equal to 100, preferably from 2 to 8; and m is an integer greater than or equal to 0 and less than or equal to 100, preferably from 2 to 8;
  ii) when p is 1;
—$(X^1)_n$— is a sequence of n independently selected amino acid units attached to A via an amide linkage to the amino terminus and to $R^1$ via the carboxy terminus of the sequence; and $X^1$ with A can be cleaved with urokinase plasminogen activator (uPA); —$(X^2)_m$— is a sequence of m independently selected amino acid units attached to $R^2$ via the amino terminus of the sequence and the rest of the molecule via an amide linkage to the carboxy terminus of the sequence; and $X^2$ can be cleaved with urokinase plasminogen activator (uPA); n is an integer of from 1 to 100, preferably 2 to 8; m is an integer of from 0 to 100, preferably 2 to 8; and tautomers and pharmaceutically acceptable derivatives thereof.

Amino acids or peptides conjugated to the amino group at C5 position of amiloride are sometimes designated AmC(5)-aa or AmC(5)-peptide. Amiloride, when conjugated to an amino acid in the C5 position, functions as a pseudo-amino acid positioned at the N-terminus of the peptide chain.

In one embodiment, p is zero. In one instance, n is zero. In another instance, m is zero. In another embodiment, p is 1.

The C-terminal amino acid or peptide can have its carboxylic acid conjugated to another group to increase hydrophobicity, such as a benzyl group, AmC(5)aa-OBn, or more generally AmC(5)peptide-R, where R is any functional group. In formula II, $R^1$ is selected from the group consisting of hydroxy, $C_{1-8}$ alkoxy, aryl-$C_{0-8}$alkoxy, heterocyclyl and amino, each of which is optionally substituted with from 1 to 3 substituents each independently selected from the group consisting of $C_{1-8}$ alkyl, aryl-$C_{0-8}$alkyl and heterocyclyl; or a therapeutic agent.

In some embodiments of compounds having formula II, $R^1$ is selected from the group consisting of hydroxy and benzyloxy. In certain other embodiments, $R^1$ is selected from the group consisting of quinuclidinyl, piperidinyl, pyrrolidinyl and morpholinyl. In yet certain other embodiments, $R^1$ is a therapeutic agent, for example, an inhibitor of IKK (NEMO) complex. In one embodiment, $R^1$ is 6-chloro-8-amido-β-carboline having the formula:

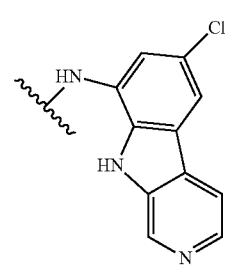

Ic

In formula II, $R^2$ is independently selected from the group consisting of H, $C_{1-8}$ alkyl, $C_{0-8}$alkylaryl, carboxy-$C_{1-8}$ alkyl and carboxy$C_{0-8}$alkylaryl. In certain embodiments, $R^2$ is selected from the group consisting of H and benzyloxycarbonyl.

Symbol A in formula II is a glycinyl or valinyl moiety, e.g. <—NH—$CHR^3$—CO—>, wherein $R^3$ is H or iPr. In one embodiment, A is attached to the pyrazine moiety through the amino group, and to the —$(X^1)_n$— sequence via the carboxyl group. Alternatively, A is connected to the pyrazine moiety through the carboxyl group, and to the —$(X^1)_n$— sequence via the amino.

In formula II, when p is zero, —$(X^1)_n$— is a sequence of n independently selected amino acid units, —NH—$R^4$—CO—, attached to A via an amide linkage to the amino terminus of the sequence and to $R^1$ via the carboxy terminus of the sequence, wherein each $R^4$ is independently an optionally substituted alkylene. When p is 1, —$(X^1)_n$— is a sequence of n independently selected amino acid units attached to A via an amide linkage to the amino terminus and to $R^1$ via the carboxy terminus of the sequence; and $X^1$ with A can be cleaved with urokinase plasminogen activator (uPA). In some embodiments, —$(X^1)_n$— is selected from the group consisting of -Gly-Arg-Gly-, -Gly-Gly-Gly-Arg-Gly, -Val-Gly-Arg-Gly-, -Val-Gly-Arg-Gly-Gly-, -Gly-Val-Gly-Gly-Arg-Gly-, -Val-Leu-Lys-Gly-, -Val-Leu-Lys-Gly-Gly-, -Gly-Val-Leu-Lys-Gly, -Gly-Arg-Gly-Gly-, -Leu-Lys-Gly-, -Leu-Lys-Gly-Gly-, -Pro-, -Gly-Arg-, -Gly-Arg-Gly-Gly-, -Gly-Gly-Arg-Gly- and -Gly-Gly-Arg-Gly-Gly-.

In one embodiment, the amiloride conjugates are activated with specific cleavage between residues in —$(X^1)_n$— or between A and —$(X^1)_n$—. In one embodiment, a bond between Arg and Gly in -A-$(X^1)_n$— is cleaved by uPA. In another embodiment, a bond between Lys and Gly in -A-$(X^1)_n$— is cleaved by uPA.

In some embodiments, the portion of the conjugate or compound represented by -A-$(X^1)_n$—$R^1$, is an amino acid (i.e., when n equals 0) or a peptide (i.e., when n is equal or greater than 1), which is conjugated to the C(5) position of amiloride via an amine bond and through A. Preferably, A is a glycine or valine residue. When n is greater than 1, $(X^1)_n$ is a peptide comprising a combination of independently selected amino acids or a polymer of one amino acid.

In formula II, when p is 0, —$(X^2)_m$— is sequence of m independently selected amino acid units represented by —NH—R⁴—CO—, wherein each R⁴ is independently an optionally substituted alkylene, including in some embodiments, a cycloalkylene (e.g., X² can include proline). The peptide is attached to R² via the amino terminus of the sequence and the rest of the molecule via an amide linkage to the carboxy terminus of the sequence. When p is 1, —(X²)$_m$— is a sequence of m independently selected amino acid units attached to R² via the amino terminus of the sequence and the rest of the molecule via an amide linkage to the carboxy terminus of the sequence; and X² can be cleaved with urokinase plasminogen activator (uPA). In some embodiments, —(X²)$_m$— is a sequence selected from the group consisting of -Gly-Gly-Arg-, -Val-Gly-Arg- and -Val-Leu-Lys-. In certain other embodiments, —(X²)$_m$— is selected from the group consisting of -Gly-Gly-Arg-Gly-, Val-Gly-Arg-Gly- and -Val-Leu-Lys-Gly-.

In one embodiment, the bond between Arg and Gly in —(X²)$_m$— is cleaved by uPA. In another embodiment, the bond between Lys and Gly in —(X²)$_m$— is cleaved by uPA.

In certain embodiments of compounds having formula (I), the amino acid sequence —(X²)$_m$— comprises at least one lysine-glycine or arginine-glycine. In other embodiments, the amino acid sequence —(X¹)$_n$ combined with A- comprises at least one lysine-glycine or arginine-glycine.

In one embodiment, the amino acids are selected from the group consisting of α-amino acids, β-amino acids, γ-amino acids, N-methyl amino acids, N-substituted glycines, and combinations thereof. In another embodiment, the amino acids are selected from the group consisting of L-amino acids, D-amino acids, and combinations thereof. In yet another embodiment, the α-amino acids are selected from the group consisting of alanine, cysteine, aspartic acid, glutamic acid, phenylalanine, glycine, histidine, isoleucine, arginine, lysine, leucine, methionine, asparagine, proline, glutamine, serine, threonine, valine, tryptophan, hydroxyproline, tyrosine, and combinations thereof. In a preferred embodiment, the amino acid or peptide is connected to the C(2) position of amiloride via a linker. Suitable linkers include glycine and a diamine. Preferably, the linker is glycine. In another preferred embodiment, n equals 1 and the amino acid is glycine, phenylalanine, (2,4-dichloro)-phenylalanine, serine, or O-benzyl serine. In still yet another embodiment, (X²)$_m$ is a peptide and m is between 2 and 50, preferably between 2 and 25, more preferably between 2 and 10, and most preferably between 2 and 8. In yet another preferred embodiment, the peptide contains one or more amino acids selected from the group consisting of (2,4-dichloro)-phenylalanine, O-benzyl serine, and combinations thereof.

Subformulae of Formula II:

In one embodiment, conjugates of formula (I) have subformula (IIa):

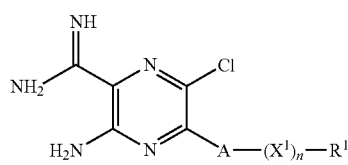

In a second embodiment, conjugates of formula (I) have subformula (IIb):

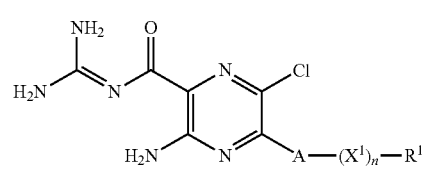

In a third embodiment, conjugates of formula (I) have subformula (IId):

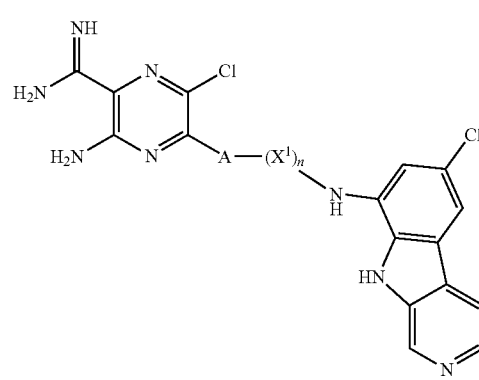

In a fourth embodiment, conjugates of formula (I) have subformula (IIe):

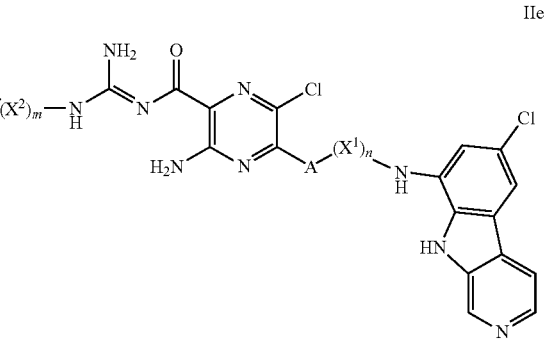

In a fifth embodiment, conjugates of formula (I) have subformula (IIf):

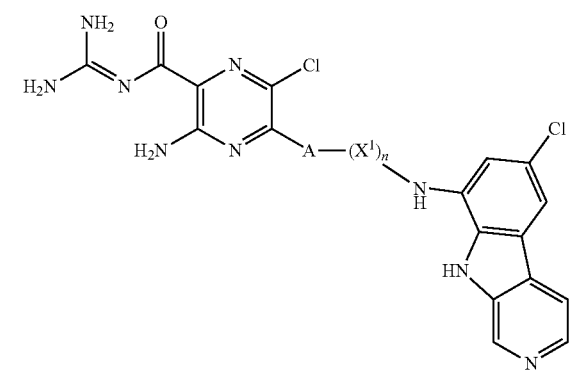

In a sixth embodiment, conjugates of formula (I) have subformula (IIj):

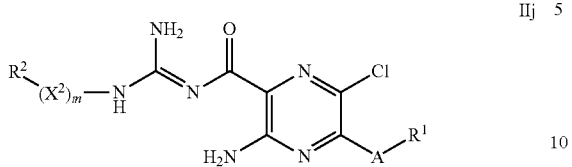

In seventh embodiment, conjugates of formula (I) have subformula (IIk):

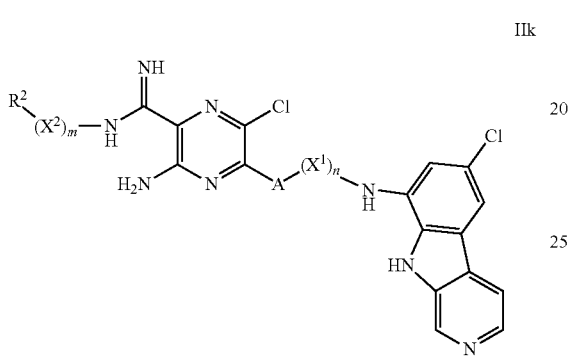

The C5am and C2am amino acid and peptide conjugates of the present invention are unique and have the following chemical properties that make them particularly useful therapeutic agents for the treatment of cancer (e.g., invasive and/or metastatic forms of glioma, breast, prostate and lung cancer), central nervous system disorders (e.g., traumatic brain injury, subarachnoid hemorrhage, seizure), stroke, cardiac arrthymia, etc.:

a. The C2am and C5am amino acid conjugates are more polar than other amiloride derivatives. Their hydrophilicity has facilitated aqueous solubilization and restricts their activity to ionic exchangers on the cell surface, thereby reducing general toxicity.

b. The C5am-Gly conjugate inhibits NHE1 in glioma cells at greater than 100-1000 times the potency of amiloride ($IC_{50}$ of about 10-100 nM), and the inhibition is rapidly reversed when the conjugate is removed from the bath. The C2am-Gly conjugate kills glioma cells at greater than 50 times the potency of amiloride.

c. The C2am and C5am amino acid conjugates are efficiently coupled to peptides that can be designed to contain cleavage sites recognized by brain- or tumor-specific peptidases. Cleavage of the peptide conjugates produces proteolytic products that can be considerably more polar than the parent conjugate. Combinatorial peptide chemistry can generate a large number of derivatives that can be screened to optimize glioma cytotoxicity and selectivity.

d. The C2,5am-(Gly)$_2$ conjugate (i.e., 2,5-bis-glycine amiloride) is a "pseudo-peptide" residue that can be introduced within peptides. This pseudo-peptide residue can be resistant to peptidases and can be introduced into peptides that are transported across the blood brain barrier (BBB) and orally across the intestinal mucosal by utilizing the mucosal peptide carrier while enhancing its resistant to mucosal peptidases (Bai, J. P. et al., *Pharm. Res.* 1992, 9(8): 969-78).

e. The C2,5am-(Gly)$_2$-peptide conjugate (i.e., Peptide 1-Gly-am-Gly-Peptide 2) can be made more hydrophobic by protecting any free carboxylic acid groups, e.g., with a protecting group. Enzymatic cleavage of Peptide 1 and/or Peptide 2 liberates the more hydrophilic, bifunctional molecule Gly-am-Gly, capable of modulating the inhibition of both NHE1 and NCX.

f. The C2-C5 dimeric amiloride conjugates can be coupled to each other through a peptide linkage that generates a hydrophobic, di-amide molecule. Blocking C-terminal carboxylates by amidation or methylation has been shown to facilitate access across the BBB. For example, the more hydrophilic C2am-Gly and C5am-Gly can be released following cleavage of the internal peptide linkage from a hydrophobic C2-C5 dimeric amiloride glycine conjugate by brain- or tumor-specific peptidases.

In one embodiment, the central nervous system disease or disorder is selected from the group consisting of a glioma, tissue injury, tissue hypoxia-ischemia, and combinations thereof. In another embodiment, the peptidase inhibitor inhibits the degradation of the peptide prior to the conjugate crossing the blood brain barrier.

Preparation of Conjugates
Synthesis of Amiloride C(5)-Peptides

In one embodiment, compounds of the present invention can be prepared by the synthetic route shown in Scheme 1 wherein A, $(X^1)_n$ and $(X^2)_m$ and p are as defined above. During and after the synthesis, certain amino or carboxyl groups of the amino acid residues may be attached to protecting groups. Suitable amino and carboxyl protecting groups include protecting groups known to a person of skill in the art and those listed in Greene et al. PROTECTIVE GROUPS IN ORGANIC SYNTHESIS, 3rd ed, Wiley, 1999. Examples of suitable amino protecting groups include Boc and Fmoc. Suitable C-terminal protecting group include benzyl ester (OBn) The synthetic routes described herein are readily amenable to the incorporation of stable hydrophobic groups at the C-terminus, including but not limited to benzyl ester (OBn), t-butylesters or alkylsulfones.

Scheme 1

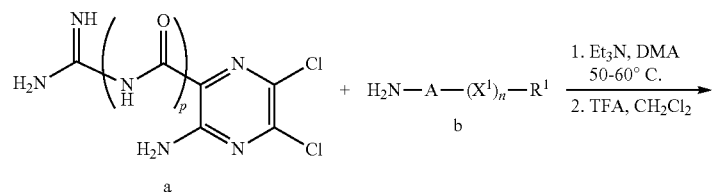

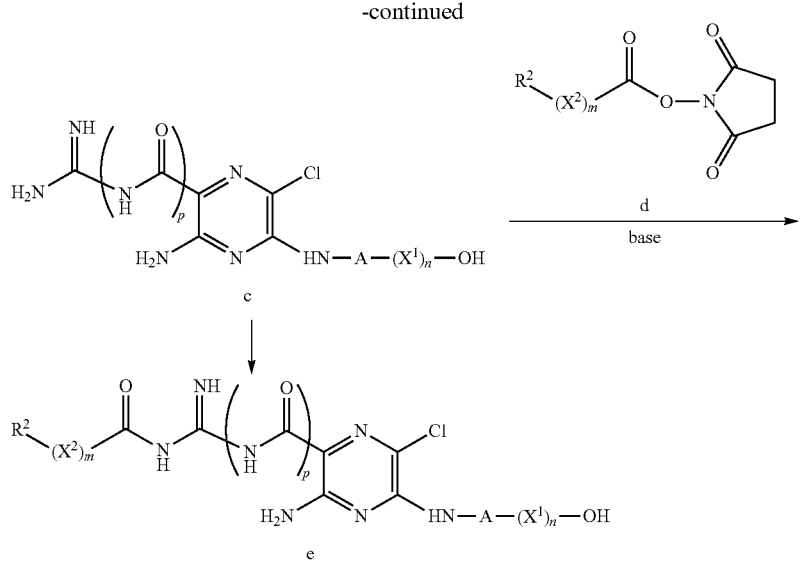

Suitable peptides which can act as uPA substrates include, but are not limited to: Z-GGR-AMC (see Zimmerman, M., et al., *Proc Natl Acad Sci USA*, 1978. 75(2): p. 750-3); Am-C(5)-Gly-Gly-Arg⊥Gly-OBn; Am-C(5)-Gly-Gly-Gly-Arg⊥Gly-OBn and Am-C(5)-Gly-Gly-Arg⊥Gly-Gly-OBn, wherein ⊥ indicates the scissile bond; i.e. the site of enzymatic cleavage. In one embodiment, the uPA recognition sequence is flanked with additional Gly residues to facilitate uPA recognition of the RG sequence. Glycine chain extension has been used to modify AmC(5)-G-G-F-L, (which is not cleaved by enkephalinase) to AmC(5)-G-G-G-F-L (which is cleaved by enkephalinase) (see Palandoken, H. et al., *J. Pharm. Exptl. Ther.* 2005, 312, 961-967). The coupling of 3-amino-5,6-dichloro-N-(diaminomethylidene)pyrazine-2-carboxamide to benzylated, Boc-protected tetra- and pentapeptides can be performed according to published methods (see Palandoken, 2005, above). Short peptide syntheses can be performed starting from glycine benzyl ester p-toluenesulfonic acid salt using standard dehydrative procedures.

Using the approach given in Scheme 1, the following conjugates modeled after uPA substrate Boc-VGR-bNA (Dooijewaard, 1983; Renatus, M. et al., *J. Biol. Chem.* 1997, 272, 21713-21719) can be prepared: Am-C(5)-Val-Gly-Arg⊥Gly-OBn (5a) and Am-C(5)-Val-Gly-Arg⊥Gly-Gly-OBn (5b), wherein ⊥ indicates the scissile bond; i.e. the site of enzymatic cleavage. The enzymatic degradation of these Am-peptide conjugates affords Am-C(5)-Val. Similarly, Am-C(5)-Val and Am-C(5)-Val-OBn can be synthesized with and without a Gly spacer (for example, to generate Am-C(5)-GVGR⊥G-OBn) (see, Palandoken et al., ibid. 2005). In another embodiment, Lys-containing analogs modeled after the uPA substrate VLK-pNA (Verheijen, 1984) can be prepared, including but not limited to: Am-C(5)-Val-Leu-Lys⊥Gly-OBn, Am-C(5)-Val-Leu-Lys⊥Gly-Gly-OBn and Am-C(5)-Gly-Val-Leu-Lys⊥Gly-OBn.

Synthesis of Amiloride C(2)-Peptides

The C(2)-acylguanidine moiety of amiloride reacts efficiently with electrophilic reagents, and this approach can been used to prepare both C(2)-benzyl analogs (e.g., 2',4'-DCB, a potent NCX inhibitor) (Simchowitz, L. et al., In *Amiloride and its analogs, unique cation transport inhibitors*; Cragoe, Jr., E. J.; Kleyman, T. R.; Simchowitz, L., Eds; VCH: New York, 1992, pp 9-24) and the amiloride C(2)-peptide analog Leu-Gly-C(2)-Am (Pató, 1999). Similarly, Am-C(5)-Gly (1) can be reacted with the N-hydroxy-succinimide (NHS) esters of Cbz-protected tripeptides (e.g., ZHN-Xaa-C(O)—NHS) (Scheme 1). To prepare the analog Gly-C(2)-Am-C(5)-Gly, Pató's isobutylchloroformate procedure can be used (Pató, J. et al., *J. Bioactive Compt. Polymers* 1999, 14, 99-121). In one embodiment, prior formation of the corresponding NHS derivative (DCC, $CH_2Cl_2$) can be used in the coupling to the acylguanidine moiety to furnish the C(2)-conjugate (Palandoken, H. Ph.D. Dissertation, "I. Amiloride-peptide conjugates: Stealth inhibitors of cell surface ion exchangers. II. A facile synthesis of (tert-alkoxy)amines."; University of California, Davis, 2006, pp 41-49). In one embodiment, the following conjugates modeled after the uPA recognition substrates can be prepared using this procedure: Z-Gly-Gly-Arg⊥C(2)-Am-C(5)-Gly, Z-Val-Gly-Arg⊥C(2)-Am-C(5)-Gly, and Z-Val-Leu-Lys⊥C(2)-Am-C(5)-Gly; wherein ⊥ indicates the scissile bond; i.e. the site of enzymatic cleavage.

Synthesis of C(2)-Amidine Analogs.

Several heteroaromatic carboxamidines [Ar—C(=NH)NH₂] are potent inhibitors of uPA (Nienaber, V. et al., *J. Biol. Chem.* 2000, 275, 7239-7248; Rudolph, M. J. et al., *Bioorg. Med. Chem. Lett.* 2002, 12, 491-495; Schweinitz, A. et al., *J. Biol. Chem.* 2004, 279, 33613-33622). C(2)-amidine peptide conjugates wherein the amiloride C(2)-acylguanidine moiety is replaced by a C(2)-amidine can also be prepared according to the synthetic routes outlined in Scheme 2 using a common synthetic intermediate, C(2)-carbonitrile. The C(2) imidate precursor, 5,6-dichloropyrazine, has been prepared previously in 3 steps from commercially available 5,6-dichloropyrazine methyl ester f (Jones, J. H. et al., *J. Med. Chem.* 1968, 11, 322-325).

Scheme 2

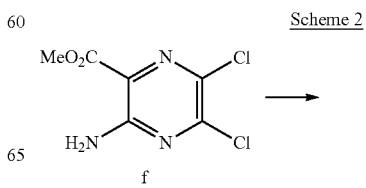

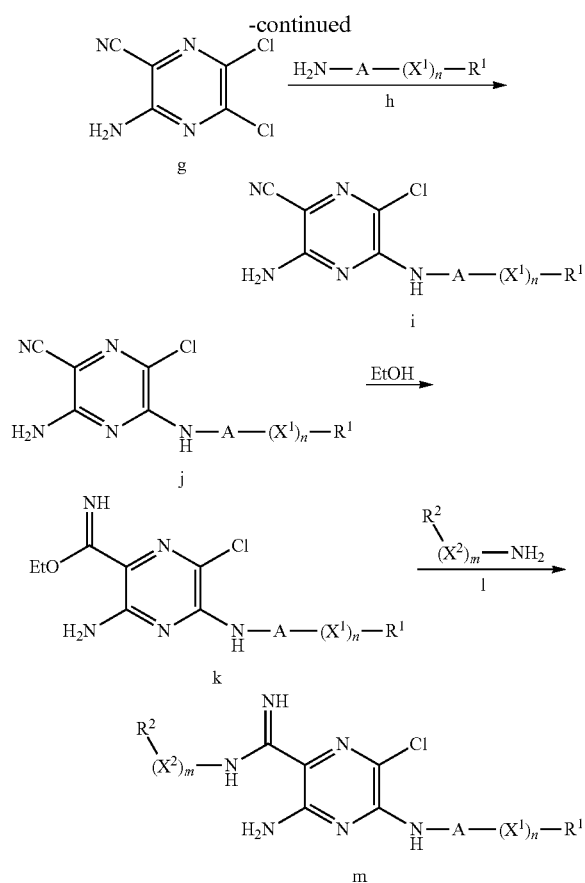

Scheme 2. Synthesis of C(2)- and C(5)-peptide conjugates.

The C(2) conjugates can be prepared by reacting a C(2) imidate with the amino end-group of a peptide. C(5) conjugates can be prepared by a method which is analogous to the synthesis of acylguanidine analogs (i.e., nucleophilic addition-elimination of amines to a C(5)-chloropyrazine—here the amine terminus of $-A-(X^1)_n-R^1$ is shown for clarity in compounds h, i, j, k and m). Furthermore, the reactions with primary and secondary amines proceed regioselectively to deliver the C(5)-coupled products (Jones, 1968; Johnston, U.S. Pat. No. 4,518,599). Thus, analogous to the synthesis of Am-C(5)-Gly-OBn, reaction with $H_2NCH_2CO_2Bn$ proceeds with good selectivity. The nitrile moiety can be transformed to the corresponding C(2)-amidine by reaction with ammonia (Gautier, J. et al., *The Chemistry of Amidines and Imidates*; Wiley: NY 1975, p. 283). The C(6)-chloro group is stable to these conditions (U.S. Pat. No. 4,518,599). In this way, C(2) amid-Am-C(5)-peptides can be prepared. Subsequent Boc protection followed by conjugation to uPA-specific peptide sequences (e.g. EDC, HOBt couplings) and Boc deprotection (TFA) can be performed to prepare the C(5)-conjugates. Suitable peptide sequences include, but are not limited to: C(2) amid-Am-C(5)-Gly-Gly-Arg⊥OBn, C(2)amid-Am-C(5)-Gly-Gly-Arg⊥Gly-OBn, C(2)amid-Am-C(5)-Val-Gly-Arg⊥OBn, or C(2)amid-Am-C(5)-Val-Gly-Arg⊥Gly-OBn, wherein ⊥ indicates the scissile bond; i.e. the site of enzymatic cleavage.

C(2)-conjugates can also be prepared by converting nitrile to the C(2)-imidate (Scheme 2) using literature protocols for synthesis of imidates (Watthey, J. W. H. et al., *J. Med. Chem.* 1980, 23, 690-692). The crude imidate products may be reacted directly with amines to obtain substituted amidines (Özden, S. et al., *Bioorg. Med. Chem. Lett.* 2005, 13, 1587-1597). Reaction with select Cbz-protected peptide reagents is a convenient method for synthesis of the C(2)-conjugates. Suitable conjugates that can be made by this method include, but are not limited to: Z-Gly-Gly-Arg⊥C(2)amid-Am-C(5)-Gly and Z-Val-Gly-Arg⊥C(2)amid-Am-C(5)-Gly.

Synthesis of Peptide β-Carboline Conjugates 6-chloro-8-amino-b-carboline (o, Scheme 3) derivatives can be prepared using the synthesis reported by Castro et al. (Castro, A. C. et al., *Bioorg. Med. Chem. Lett.* 2003, 13, 2419-2422) Subsequent conjugation of the 8-amino moiety to peptide analogs will provide a

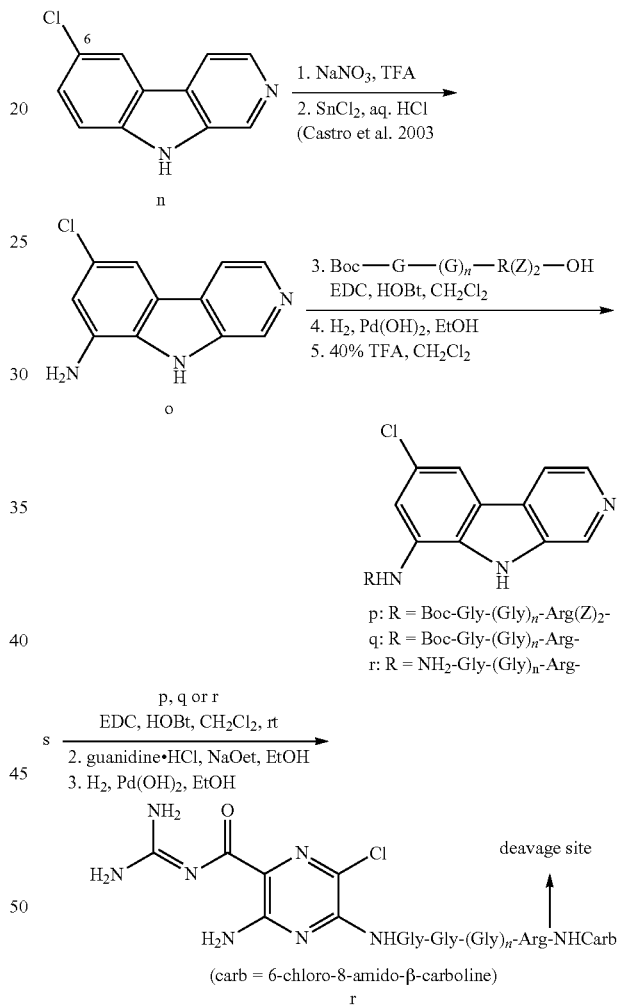

cleavable prodrug for inhibition of IKK. Nitration of 6-chloro-b-carboline (n), readily prepared from norharman (Acros Organics) by electrophilic chlorination (NCS, THF, 48 h) (Trudell, M. L. et al., *J. Org. Chem.* 1988, 53, 4185-4190; Castro, A. C. et al., *Bioorg. Med. Chem. Lett.* 2003, 13, 2419-2422), followed by reduction provides key amino-intermediate of type o. Conjugation of o to short bis(Cbz-protected) Gly-Arg peptides featuring the uPA cleavage sequence yields conjugates such as p, q or r (n=0, 1, etc.). Subsequent Cbz hydrogenolysis (Edwards, 2000) followed by Boc deprotection furnishes substrates such as t. The above methodology allows one to alter the length (i.e., adjust 'n')

and/or the amino acid sequence of the peptide reagent in coupling step 3 to incorporate an additional amino acid units (e.g., Boc-G-G-R(Z)2-G-OH) including sequences with Gly spacer between the amino acids e.g. Arg and Carb.

The substrates may then be conjugated with the corresponding peptide reagent p3 (Scheme 3), prepared by selective Boc-deprotection (TFA) of Carb-conjugates such as p, q or r to amiloride ester s. Subsequent installation of the guanidine moiety using Cragoe's method ((Cragoe E. J. et al., *J. Med. Chem.* 1967, 10, 66-75) followed by Cbz hydrogenolysis delivers the Am-C(5)-peptide-Carb conjugate t. Alternatively, peptide p1 can be directly and regioselectively coupled to C(5) of amiloride by reaction with 3-amino-5,6-dichloro-N-(diaminomethylidene)pyrazine-2-carboxamide b using the method for synthesis of Am-C(5)-peptide conjugates (Palandoken, et al., *J. Pharm. Exptl. Ther.* 2005, 312, 961-967).

Likewise, uPA-specific peptide-carb reagents, such as p3, can be coupled to nitrile or imidates (from Scheme 2). Suitable amidine analog which can be made by this method include conjugate C(2)amid-Am-C(5)-Gly-Gly-Arg⊥Carb.

Methods

The urokinase-urokinase plasminogen activator receptor system (uPA-uPAR) has been implicated in the promotion of tumor cell invasion utilizing inflammatory pathways (Chandrasekar, N., et al., Oncogene, 2003. 22(3): p. 392-400; Das, R., G. H. et al. J Biol Chem, 2004. 279(12): p. 11051-64; Das, R., et al., *Osteopontin: it's role in regulation of cell motility and nuclear factor kappa B-mediated urokinase type plasminogen activator expression.* IUBMB Life, 2005. 57(6): p. 441-7). For example, osteopontin (OPN) is present or increased in 60-80% malignant gliomas, including the human U87 glioma cell line (Said et al., 2005) and increased OPN expression corresponds with increased invasiveness in malignant gliomas, breast cancer, renal cell cancer, prostate, renal cell, lung cancers (Riffling, S. R. et al., Br J Cancer, 2004. 90(10): p. 1877-81; Rangaswami, H., A. et al., Trends Cell Biol, 2006. 16(2): p. 79-87), and pediatric atypical teratoid/rhabdoid tumors of CNS (Kao, C. L., et al., Mod Pathol, 2005. 18(6): p. 769-78). OPN expression is associated with the cell-type dependent activation of the NFkB (Rangaswami, H., A. et al., J Surg Res, 2005. 127(1): p. 46-52), AKT (Galaria et al., 2005), integrin/SHP2 (Carlin, S. M., et al., Faseb J, 2005. 19(2): p. 195-202), and STAT/JNK pathways (Oktay, M., et al., J Cell Biol., 1999. 145(7): p. 1461-9; Yang, Y. M., et al., Clin Cancer Res., 2003. 9(1): p. 391-401) generating increased expression of OPN, pro-urokinase plasminogen activator (pro-uPA) with resultant activation of the plasmalemmal uPA-uPAR system (Carlin et al., id) (Margheri, F., et al., Gene Ther, 2005. 12(8): p. 702-14). Urokinase has also been shown to activate intracellular and extracellular signaling pathways leading to cancer cell proliferation, angiogenesis, and invasion. ((Lakka, S. S., et al., id, 2005). Binding of uPA to uPAR in cells activates the signal-regulated kinase 1/2 (ERK1/2) pathway, which controls cancer cell invasion, proliferation, and survival in some cancer cell types (Mazzieri, R., et al., Mol Biol Cell, 2006. 17(1): p. 367-78; Yoon, S. Y., et al., Cell Res, 2006. 16(1): p. 75-81). Thus in one aspect, the present invention provides a method for inhibiting urokinase plasminogen activator (uPA), the OPN pathway or autocrine or paracrine cell activation comprising contacting cells with a prodrug comprising an inhibitor of intracellular urokinase plasminogen activator (uPA) covalently attached to a substrate of intracellular urokinase plasminogen activator (uPA). In another aspect, the present invention provides a method for inhibiting tumor growth comprising contacting the tumor cells with a prodrug comprising an inhibitor of intracellular urokinase plasminogen activator (uPA) covalently attached to a substrate of intracellular urokinase plasminogen activator (uPA).

Thus, in another aspect, the present invention provides a method for treating or preventing inflammation or cancer, and in particular the recurrence of cancer, in a subject in need thereof. The method includes administering to said subject a conjugate of an intracellular urokinase plasminogen activator (uPA) inhibitor and a substrate of intracellular urokinase plasminogen activator (uPA). In one embodiment, the conjugate further comprises an additional therapeutic agent. The additional therapeutic agent includes an inhibitor of IKK (NEMO) complex.

In one embodiment, the method includes administering to said subject a formula I:

$$D\text{-}X\text{---}R \quad\quad\quad I$$

wherein

D is an inhibitor of intracellular urokinase plasminogen activator (uPA);

X— is peptidyl substrate of urokinase plasminogen activator (uPA) attached to D and R via an amide linkage;

R is a hydrophobic moiety or an additional therapeutic or diagnostic agent;

and pharmaceutically acceptable derivatives thereof.

In another embodiment, the method includes administering to said subject a compound of the formula:

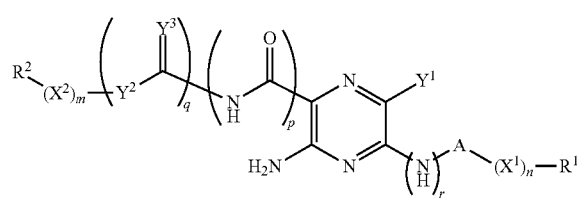

Ia wherein the subscripts n, m, p, q and r, and the variables $R^1$, $R^2$, $X^1$, $X^2$, $Y^1$, $Y^2$, $Y^3$, and A are as provided above.

In one selected group of embodiments, the method includes administering to said subject a compound of the formula:

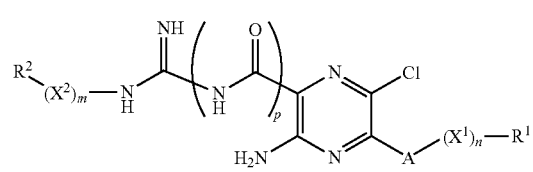

II wherein A, p, m, n, $R^1$, $R^2$, $(X^1)_n$ and $(X^2)_m$ are as defined above.

In another group of embodiments, the method includes administering to said subject a compound of the formula:

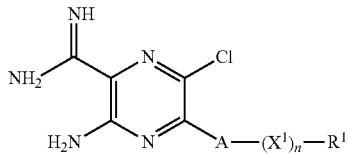

IIa

The substituents are as defined above.

In yet another group of embodiments, the method includes administering to said subject a compound of the formula:

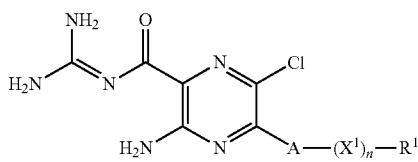

IIb

The substituents are as defined above.

In still another group of embodiments, the method includes administering to said subject a compound of the formula:

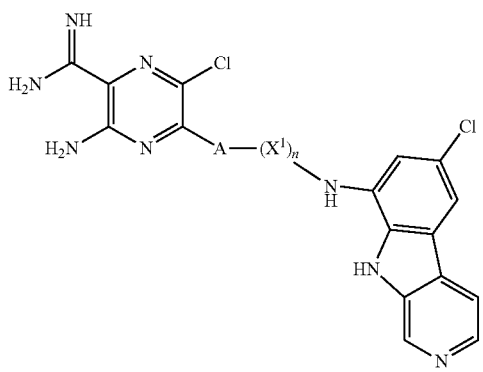

IId

The substituents are as defined above.

In other embodiments, the method includes administering to said subject a compound of the formula:

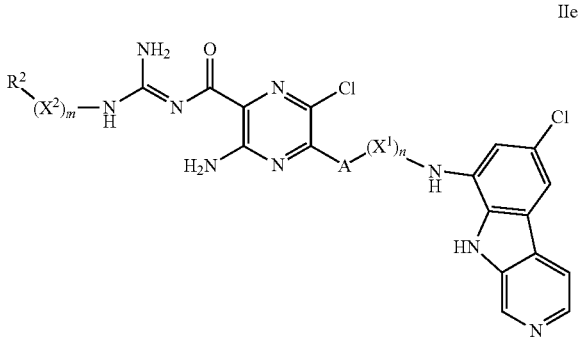

IIe

The substituents are as defined above.

In yet another group of embodiments, the method includes administering to said subject a compound of the formula:

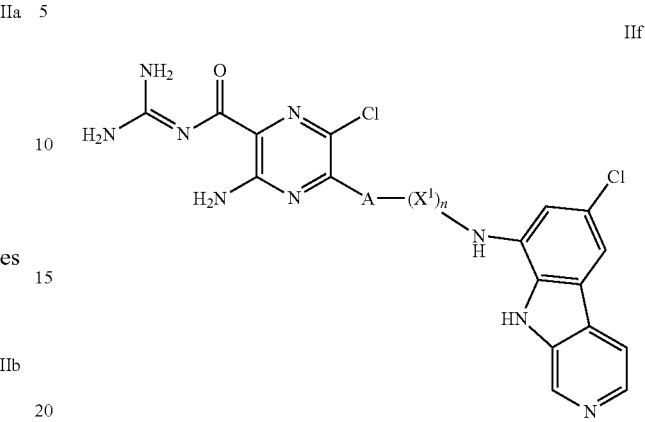

IIf

The substituents are as defined above.

In still other embodiments, the method includes administering to said subject a compound of the formula:

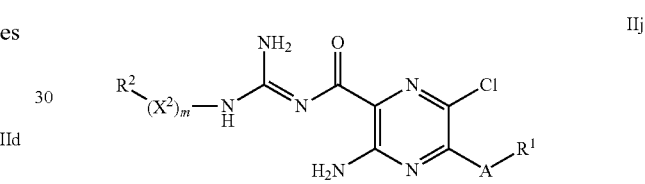

IIj

In further embodiments, the method includes administering to said subject a compound of the formula:

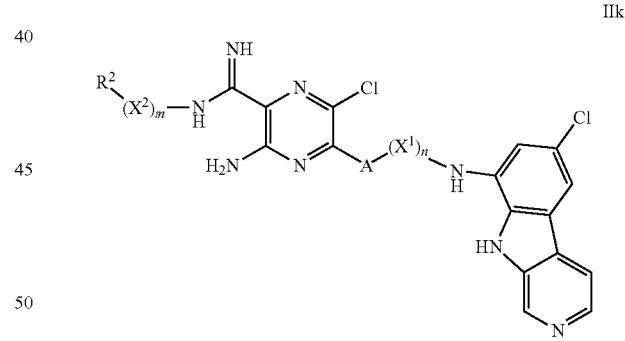

IIk

In another embodiment of the method of administering the conjugates of formula (I), the conjugates are cleaved by intracellular urokinase plasminogen activator (uPA), thereby delivering said inhibitor having the formula:

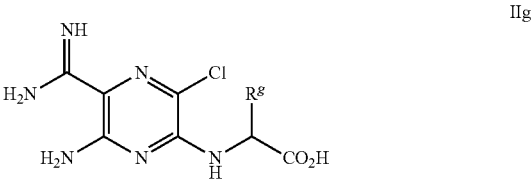

IIg wherein R$^g$ is an amino acid side chain. Exemplary amino acid side chain includes, but are not limited to, a side chain of any of the 20 natural amino acids, such as —H, —CH$_3$, isopropyl, sec-butyl, iso-butyl, benzyl, —CH$_2$OH, —CH(CH$_3$)OH, -Ph-OH, —CH$_2$SH, —CH$_2$CH$_2$SCH$_3$, —CH$_2$(CO)NH$_2$, —CH$_2$CH$_2$(CO)NH$_2$, —CH$_2$-indolyl, —CH$_2$-indole-3-yl, —CH$_2$COOH, —CH$_2$CH$_2$COOH, —CH$_2$CH$_2$CH$_2$CH$_2$NH$_2$, —CH$_2$CH$_2$CH$_2$NH—(C=NH)NH$_2$, —CH$_2$-imidazolyl and —CH$_2$-imidazole-5-yl. In one instance, R$^g$ is —H.

In yet another embodiment of the method of administering the conjugates of formula (I), the conjugate is cleaved by intracellular urokinase (uPA), thereby delivering an inhibitor having the formula:

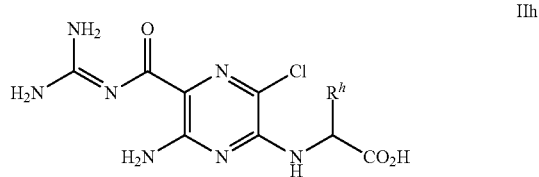

IIh wherein R$^h$ is an amino acid side chain. Exemplary amino acid side chain includes, but are not limited to, a side chain of any of the 20 natural amino acids, such as —H, —CH$_3$, isopropyl, sec-butyl, iso-butyl, benzyl, —CH$_2$OH, —CH(CH$_3$)OH, -Ph-OH, —CH$_2$SH, —CH$_2$CH$_2$SCH$_3$, —CH$_2$(CO)NH$_2$, —CH$_2$CH$_2$(CO)NH$_2$, —CH$_2$-indolyl, —CH$_2$-indole-3-yl, —CH$_2$COOH, —CH$_2$CH$_2$COOH, —CH$_2$CH$_2$CH$_2$CH$_2$NH$_2$, —CH$_2$CH$_2$CH$_2$NH—(C=NH)NH$_2$, —CH$_2$-imidazole-5-yl and —CH$_2$-imidazolyl. In one instance, R$^h$ is —H.

In still another embodiment of the method of administering the conjugates of formula (I), the conjugates further include a therapeutic agent. For example, the therapeutic agent is an inhibitor of IKK (NEMO) complex. In one embodiment, the conjugates are cleaved by intracellular urokinase plasminogen activator (uPA), thereby delivering an inhibitor of IKK (NEMO) complex having the formula:

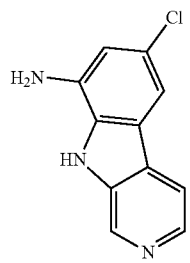

IIi

The present invention provides methods of treatment for various cancers that express urokinase. In one embodiment, the cancer is lung cancer, breast cancer, prostate cancer, bladder cancer, thyroid cancer, liver cancer, pleural cancer, pancreatic cancer, ovarian cancer, cervical cancer, testicular cancer, colon cancer, B-cell lymphoma, non-Hodgkin's lymphoma, Burkitt's lymphoma, fibrosarcoma, neuroblastoma, glioma, melanoma, monocytic leukemia, myelogenous leukemia, and combinations thereof. The cancer also includes those that are invasive, metastatic, and resistant to chemotherapy and radiation therapy. The cancer cells can overexpress urokinase plasminogen activator (uPA) as compared with other cells. Preferably, the cancer is a glioma, breast, prostate or lung cancer. More preferably, the cancer is a glioma. In another embodiment, the cancer is treated by killing cancer cells, inhibiting the proliferation of cancer cells, or a combination thereof.

In a further aspect, the present invention provides a method for delivering a conjugate across the blood brain barrier in a subject in need thereof. The method includes administering to the subject a conjugate having any one of formulae (I), (Ia)-(Ib), (Id)-(If) and (Ij)-(Ik).

In one embodiment, the central nervous system disease or disorder is selected from the group consisting of a glioma, tissue injury, tissue hypoxia-ischemia, and combinations thereof. In another embodiment, the peptidase inhibitor inhibits the degradation of the peptide prior to the conjugate crossing the blood brain barrier.

In another aspect, the present invention provides a method of generating an intracellular urokinase plasminogen activator (uPA) inhibitor. The method includes contacting a conjugate of an intracellular urokinase plasminogen activator (uPA) inhibitor and a substrate of intracellular urokinase plasminogen activator (uPA) with a urokinase plasminogen activator. In one embodiment, the bonds between arginine and glycine of the AmC(5) conjugates are cleaved by uPA to generate proteolytic product AmC(5) amino acid or AmC(5) peptide product. In another embodiment, the bonds between lysine and glycine of the AmC(5)-peptide conjugates is cleaved by uPA. In yet another embodiment, uPA cleaves the bonds between either arginine and guanidine or lysine and guanidine of peptide-C(2)Am conjugates. In still another embodiment, uPA cleaves the bonds between arginine and amidine or lysine and amidine of peptide-amidine-C(2)Am conjugates. In a preferred embodiment, the proteolytic product is C5amGly-Gly-Arg, C5am-(Gly)$_3$-Arg, C5am-Val-Gly-Arg, C5am-Gly-Val-Gly-Arg, C5am-Val-Leu-Lys, C5am-Gly-Val-Leu-Lys, C2-amid-amC5-Gly, C2-amid-amC5-Gly-Gly-Arg, C2-amid-amC5-Val-Gly-Arg, C5am-Val-Gly-Gly-Arg, Gly-carb or Gly-Gly-carb.

In some embodiments, the method of generating a uPA inhibitor includes contacting a compound having any one of formulae (I), (Ia)-(Ib), (Id)-(If) and (Ij)-(Ik) with urokinase plasminogen activator.

In yet another aspect, the present invention provides a method of generating an inhibitor of IKK (NEMO) complex. The method includes contacting a conjugate of an inhibitor of IKK (NEMO) complex and a substrate of intracellular urokinase plasminogen activator (uPA) with urokinase plasminogen activator.

In certain embodiments, the method of generating an inhibitor of IKK (NEMO) complex includes contacting a compound having any of formulae (I), (Ia)-(Ib), (Id)-(If) and (Ij)-(Ik) with urokinase plasminogen activator (uPA).

The present invention provides methods for administering hydrophobic peptide-drug conjugates that can then be converted in vivo to hydrophilic agents upon the action of a peptidase. These methods permit efficient accessibility and penetration of the conjugates into a tissue or other site of action (e.g., across the blood brain barrier) and utilize peptidases, such as uPA, present in the tissue or site of action to selectively cleave the conjugate and liberate a hydrophilic agent that acts at the level of the cell surface, thereby reducing general toxicity. Suitable drugs for use in the peptide-drug conjugates include, without limitation, anti-cancer agents, anti-inflammatory agents, anti-viral agents, antifungal agents, and anti-bacterial agents, wherein the peptide conjugated to the drug is selectively cleaved by a peptidase expressed at the intended site of drug action, e.g., a tumor, an injured tissue, an organ, etc., to generate the hydrophilic agent.

Compositions

The amiloride conjugates of the present invention can be provided in pharmaceutical compositions for administration to a subject in need thereof. Such compositions will contain, in addition to at least one amiloride conjugate as the active agent(s), one or more pharmaceutically acceptable excipients, carriers, diluents, tissue permeation enhancers, solubilizers, and adjuvants. Other therapeutic agents may be included, e.g., anticancer agents, vasoconstrictors, anti-inflammatory agents, antibiotics, and counter-irritants. Suitable anticancer agents include, but are not limited to, cytotoxins and agents such as antimetabolites, alkylating agents, anthracyclines, antibiotics, antimitotic agents, procarbazine, hydroxyurea, asparaginase, corticosteroids, interferons, radiopharmaceuticals, and conjugates of peptides with antitumor activity, e.g., TNF-α. The compositions may be formulated using conventional techniques such as those described in Remington's Pharmaceutical Sciences, Mace Publishing Co., Philadelphia, Pa. $17^{th}$ Ed. (1985) and "Modern Pharmaceutics," Marcel Dekker, Inc. $3^{rd}$ Ed. (G. S. Banker & C. T. Rhodes, Eds.). Pharmaceutically acceptable salts of the amiloride conjugates (e.g., acid addition salts) may be prepared using standard procedures known to those skilled in the art of synthetic organic chemistry and described, e.g., by J. March, Advanced Organic Chemistry: Reactions, Mechanisms and Structure, $4^{th}$ Ed. (New York: Wiley-Interscience, 1992).

For topical administration, the compositions of the present invention comprising amiloride conjugates can be in the form of emulsions, creams, jelly, solutions, and ointments. For parenteral administration, the compositions can be in the form of sterile injectable solutions and sterile packaged powders. Preferably, injectable solutions are formulated at a pH of about 4.5 to about 7.5. For oral administration, the compositions can be in the form of tablets, capsules, emulsions, suspensions, solutions, syrups, sprays, and lozenges. Some examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, and methylcellulose. The compositions can additionally include lubricating agents such as talc, magnesium stearate, and mineral oil; wetting agents, emulsifying and suspending agents; preserving agents such as methyl- and propylhydroxy-benzoates, sweetening agents, and flavoring agents. The compositions may also comprise biodegradable polymer beads and dextran and cyclodextrin inclusion complexes.

In Vitro Evaluation of Novel Amiloride Compounds

In a preferred embodiment, the C5am and C2am peptide conjugates of the present invention are selectively cleaved within the brain by (1) enkephalinase, an endogenous neutral endopeptidase 24.11; or (2) matrix metalloproteinase-2 (MMP-2), synthesized by many highly infiltrative gliomas. Typically, peptides are designed to identify the minimum number of amino acid residues that optimally (1) discriminate between glioma cells and astrocytes; and (2) inhibit NCX and/or NHE1. In addition, enzymatic recognition sequences are designed within the peptides to permit selective cleavage by enzymes (e.g., brain and/or tumor peptidases). For example, C5am-Gly or C2am-Gly conjugates containing peptides that mimic opioid peptides or MMP-2 substrates attached to the glycine are within the scope of the present invention. Such conjugates can be evaluated for any of various structure-activity relationships (SAR) such as enzymatic specificity and biological activity in glioma cells. In a particularly preferred embodiment, the C5am-Gly or C2am-Gly conjugates are coupled to [Leu]$^5$-enkephalin analogs (e.g., Gly-Gly-Gly-Phe-Leu-OH) that closely resemble members of the opioid peptide family that effectively enter the brain following intravenous injection (Cornford et al., Lancet Neurol., 1:306-315 (2002)). Any of the peptide conjugates of the present invention are useful for enhancing the efficacy and selectivity (i.e., specificity) of the antiproliferative and cytotoxic effects of amiloride conjugates in killing and/or inhibiting the proliferation of tumor cells such as glioma cells. Recognition sequences within the conjugates are designed to be cleaved by brain or tumor peptidases to increase the hydrophilicities of the active compounds to impede their intracellular permeation, thereby reducing toxicity.

The C2am-Gly, C5am-Gly, and peptide conjugates thereof are synthesized with high overall yields. Preferably, the conjugates demonstrate cytotoxic and/or antiproliferative effects on U87 glioma cells that correspond with their predicted inhibition of NCX and NHE1. Although solubilization is a common problem with peptides, the peptide conjugates of the present invention are soluble in mixtures of aqueous buffers containing approximately <20% of DMSO. As peptide derivatives frequently need modified amino acid residues in order to be clinically effective and/or to prevent unwanted cleavage by endogenous peptidases, D-amino acids, N-methyl amino acids, N-substituted glycines, cyclic amino acid derivatives, and combinations thereof may be introduced into the peptide conjugates of the present invention. For example, "peptidomimetism" introduces hydrocarbon bonds that retain the confomeric structure of the peptide backbones, while retaining critical amino acid sidechains to overcome problems of peptide instability, poor absorption, and rapid metabolism (Marshall, Biopolymers, 60:246-277 (2001)). Further, combinatorial peptide syntheses can rapidly generate novel sets of amiloride derivative compounds that can be examined to optimize efficacies using high throughput, tetrazolium-based screening assays of viable cell numbers of glioma cells and primary astrocytes.

A particularly appealing feature of the synthesis strategies of the present invention is the flexibility with which the peptide side chains can be incorporated onto the amiloride core. For example, partial or complete peptide sequences may be assembled prior to the reaction with resin-bound amiloride, as opposed to a step-wise amino acid sequence construction. This option provides the opportunity to incorporate radiolabels into the synthetic scheme by using radiolabeled peptide sequences. The incorporation of radiolabels could be particularly useful following preliminary LC-MS analyses to further assess the partitioning of compounds from the vascular compartment into brain tissue, their intracerebral efflux, and stability.

When the compositions of the present invention are administered orally, the peptide sequences in the amiloride-peptide conjugate are preferably designed to be resistant to digestive enzymes such as trypsin, chymotrypsin, elastase, and carboxypeptidases. When the compositions are administered intravenously, the conjugates are preferably resistant to plasma proteases such as those of the thrombolytic pathway (e.g., thrombin).

Peptide derivatives may frequently need modified amino acid residues in order to be clinically effective and/or to prevent unwanted cleavage by endogenous peptidases. Therefore, D-amino acids, N-methyl amino acids, N-substituted glycines, cyclic amino acid derivatives, and combinations thereof may be introduced into the amiloride-peptide conjugates of the present invention, and peptidomimetism can be used to overcome problems of peptide instability, poor absorption, and rapid metabolism (Marshall, id). For example, an MMP-2-cleavable peptide linker can contain modified amino acid residues flanking the MMP-2 cleavage sequence in order to confer resistance to endogenous peptidases other than MMP-2.

Utility of Novel Amiloride Compounds

The C5am-amino acid and peptide conjugates are particularly useful as highly selective and potent inhibitors of sodium-proton exchange (i.e., NHE1) whereas C2am-amino acid and peptide conjugates are particularly useful as selective and potent inhibitors of sodium-calcium exchange (i.e., NCX). Thus, C5am conjugates are particularly useful for reducing tissue swelling (e.g., acute brain swelling from stroke or head trauma) and C2am conjugates are particularly useful for killing tumors that exist in hypoxic-ischemic environments and/or for serving as a neuroprotectant during stroke or cardiac ischemia by preventing sodium and calcium entry into cells via NHE1 and NCX, respectively. Further, conjugates produced by peptide additions to both the C2 and C5 positions of amiloride are particularly useful because they would likely change the ratio of NCX/NHE1 inhibition and affect the selectivity for inhibiting the different transporter subtypes present in different tissues. This could be assessed using high throughput screens for each transporter.

The amiloride conjugates are useful anti-inflammatory agents to prevent invasion, proliferation of sensitized inflammatory cells that synthesize and urokinase plasminogen activator factor, or overexpress osteopontin or gelatinases. The human disorders include, but are not limited to, osteoarthritis, sjogrens syndrome, rheumatoid arthritis, systemic lupus erythrematosis, multiple sclerosis, post-traumatic brain injury, subarachnoid brain hemorrhage, inflammatory and immune-mediated brain disorders (encephalitis, cerebritis, arachnoiditis). The amiloride conjugates are also useful for preventing invasion, metastasis, and proliferation of cancer cells that synthesize urokinase plasminogen activator factor, or overexpress osteopontin or gelatinases. The human disorders include, but are not limited to, prostate, lung, breast, primordial neuroectodermal tumors, brain tumors Mechanisms of Action of Novel Amiloride Compounds Without being bound to any particular theory, it is thought that the amiloride conjugates of the present invention provide cytotoxic and/or antiproliferative effects by at least one of the following mechanisms: (1) reduction in intracellular pH ($pH_i$); (2) impairment of glycolysis; (3) increase in intracellular calcium levels ($[Ca^{2+}]_i$). Such effects are mediated by inhibition of NHE1, NCX, a combination of NHE1 and NCX, or through inhibition of other ionic transporters (e.g., other cell-surface $Na^+$ exchangers); (4) inhibition of uPA, IKKβ or other proteases or tyrosine kinases.

In one embodiment, extracellular uPA bound to UPAR can also cleave inactive amiloride peptide prodrug generating AmC(5)-peptide that inhibits extracellular uPA.

FIG. 1A illustrates a model for tumor cell death induced by the amiloride conjugates of the present invention. Administration of a hydrophobic, substituted peptide conjugate of amiloride, e.g. AmC(5)-(peptide)$_n$R, permeates cells. The inactive peptide conjugate is activated following endopeptidase cleavage by uPA. The hydrophilic peptide conjugate of accumulates within the cell where it inhibits uPA. Extracellular uPA bound to uPAR can also cleave inactive amiloride peptide prodrug generating a compound that inhibits extracellular uPA or IKK.

IV. Methods of Administration

The compositions of the present invention comprising an amiloride conjugate may be administered by any of the accepted modes of administration of agents having similar utilities, for example, by oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route, including parenteral and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The compositions may be administered as a single injection or continuously through an indwelling catheter, or administered topically to the skin, mucus membranes, etc. The composition containing the amiloride conjugate may be administered repeatedly, e.g., at least 2, 3, 4, 5, 6, 7, 8, or more times, or the composition may be administered by continuous infusion.

In one embodiment, the conjugate is administered through pulse administration. In one embodiment the method is to prevent cancer recurrence using pulsed administration of inactive prodrugs that inhibit the proliferation and invasion of cancer cells that resist standard chemotherapy and radiation therapy.

The compositions can be formulated in a unit dosage form. The term "unit dosage form" refers to physically discrete units suitable as unitary dosages for human subjects and other mammals, each unit containing a predetermined quantity of active material calculated to produce the desired onset, tolerability, and therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of the amiloride conjugate.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. In one embodiment of the present invention, the lyophilized composition is provided in a syringe, optionally packaged in combination with the buffer for reconstitution, such that the reconstituted anesthetic composition can be immediately administered to a patient.

The dose administered will vary depending on a number of factors, including, but not limited to, the type of cancer, the location of the tumor, and the physical condition of the patient. Preferably, the smallest dose and concentration required to produce the desired result should be used. Dosage should be appropriately adjusted for children, the elderly, debilitated patients, and patients with cardiac and/or liver disease. However, the reduced toxicity associated with the amiloride conjugates of the present invention permits a wider margin of safety for dosage concentrations and for repeated dosing.

V. Examples

The following examples are offered to illustrate, but not to limit, the claimed invention. The following abbreviations are used in the Examples and throughout the description of the invention:

EtOH: Ethanol; EtONa: Sodium ethoxide; THF: Tetrahydrofuran; TLC: Thin layer chromatography; MeOH: Methanol; EDC: 1-ethyl-3-[3-dimethylaminopropyl]carbodiimide hydrochloride; HOBt: N-hydroxybenzotriazole; TFA: Trifluoroacetic acid; DMA: Dimethyl acetamide; Fmoc: 9-fluorenylmethoxycarbonyl; BOC: t-butoxycarbonyl.

Example 1

Preparation of AmC(5)-Peptides Conjugates Containing -Gly-Gly-Arg-Sequence

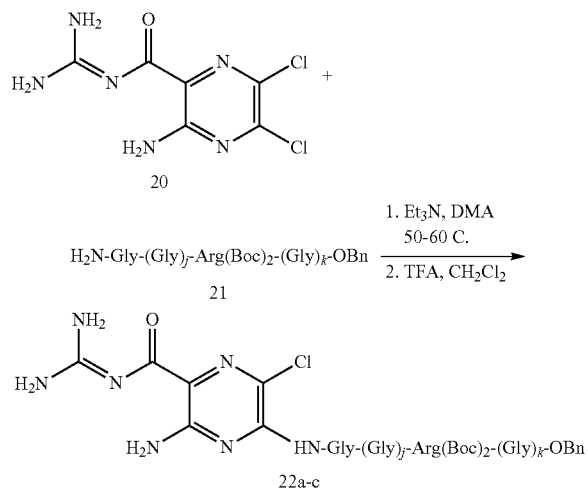

Amiloride (Am)C(5)-peptide conjugates 22a-c are synthesized (see, Scheme 4) using a methodology by Cragoe et al. (Cragoe et al., *J. Med. Chem.*, 10:66-75 (1967)) and Palandoken et al. (Palandoken, H. et al. *J. Pharm. Exptl. Ther.* 2005, 312, 961-67) by coupling pyrazine dichloride 20 to benzylated, Boc-protected tetra- and pentapeptides 21. The conjugates were purified by column chromatography ($SiO_2$) and their structural integrity confirmed by spectroscopic analyses ($^1H$ and $^{13}C$ NMR) as well as mass spectral analysis (LCMS).

Synthesis of Peptide (23):

The reaction of C-terminal benzyl-protected amino acids (1a-c) with a guanidine derivative (2) proceeded in the presence of base to regioselectively deliver C(5)-amino acid conjugates. Hydrogenolysis removed the benzyl protection group and afforded conjugates 3a-c in 30-50% overall yield As shown in Scheme 5, short peptide, such as 23 is synthesized from glycine benzyl ester p-toluenesulfonic acid salt using standard dehydrative procedures.

Scheme 5

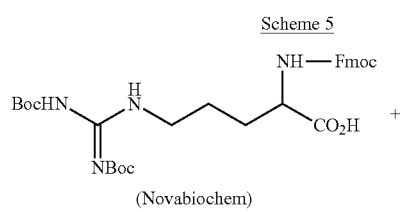

(Novabiochem)

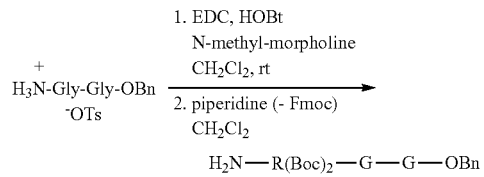

Synthesis of Am-C(5)-G-G-R⊥G-OBn (22a); Am-C(5)-G-G-G-R⊥G-OBn (22b) and Am-C(5)-G-G-R⊥G-G-OBn (22c):

The compounds are synthesized according to Scheme 4.

Example 2

Preparation of AmC(5)-Peptides Conjugates Containing -Val-Gly-Arg-Sequence

AmC(5)-peptides conjugates is synthesized by reacting pyrazine dichloride 20 with benzylated, Boc protected tetra- and pentapeptides using the procedures analogous to those shown in Scheme 4.

Synthesis of AmC(5)-Val-Gly-Arg⊥Gly-OBn (24a):

Compound 24a is synthesized by coupling pyrazine dichloride 20 with $NH_2$-Val-Gly-Arg-Gly-OBn (25).

Synthesis of AmC(5)-Val-Gly-Arg⊥Gly-Gly-OBn (24b):

Compound 24b is synthesized similarly as compound 24a by reacting pyrazine dichloride 20 with $NH_2$-Val-Gly-Arg-Gly-Gly-OBn (26).

Example 3

Preparation of AmC(5)-Peptides Conjugates Containing -Val-Leu-Lys-Sequence

AmC(5)-peptide conjugates are synthesized by reacting pyrazine dichloride with benzylated, Boc protected tetra- and pentapeptides using procedures analogous to those shown in Scheme 4.

Synthesis of Am-C(5)-Val-Leu-Lys⊥Gly-OBn (27a):

Compound 27a is synthesized by reacting pyrazine dichloride 20 with $NH_2$-Val-Leu-Lys⊥Gly-OBn (28).

Synthesis of Am-C(5)-Val-Leu-Lys⊥Gly-Gly-OBn (27b):

Compound 27b is synthesized by reacting pyrazine dichloride 20 with $NH_2$-Val-Leu-Lys⊥Gly-Gly-OBn (29).

Synthesis of Am-C(5)-Gly-Vat-Leu-Lys⊥Gly-OBn (27c):

Compound 27c is synthesized by reacting pyrazine dichloride 20 with $NH_2$-Gly-Val-Leu-Lys⊥Gly-OBn (30).

Example 4

Preparation of Peptides-C(2)-AmC(5)-Gly Conjugates

Scheme 6

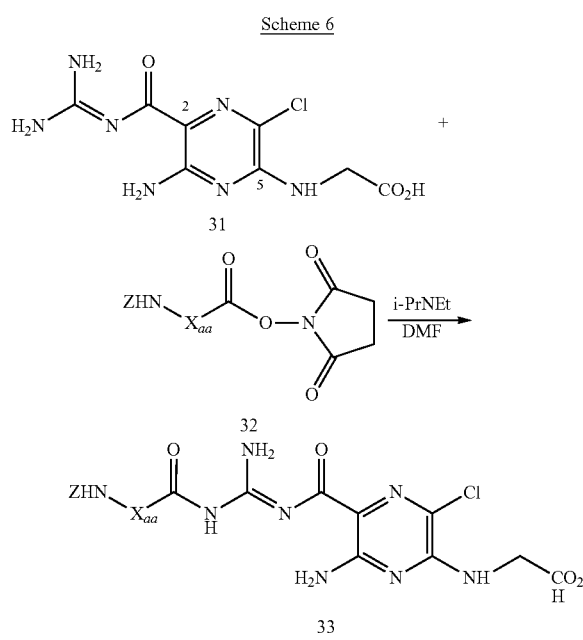

$X_{aa}$ = amino acid sequence
Z is CbZ protecting group

Peptide-C(2)-AmC(5)-Gly conjugates of formula 33 are synthesized by reacting compound 31 with the N-hydroxysuccinimide (NHS) esters of Cbz-protected peptides 32 in greater than 79% yield.

Synthesis of Z-Gly-Gly-Arg⊥C(2)-Am-C(5)-Gly (33a):

Compound 33a is synthesized by reacting compound 31 with Z-Gly-Gly-Arg-NHS (34).

Synthesis of Z-Val-Gly-Arg⊥C(2)-Am-C(5)-Gly (33b):

Compound 33b is synthesized by reacting compound 31 with Z-Val-Gly-Arg-NHS (35).

Synthesis of Z-Val-Leu-Lys⊥C(2)-Am-C(5)-Gly (33c):

Compound 33c is synthesized by reacting compound 31 with Z-Val-Leu-Lys-NHS (36).

Example 5

Preparation of C(2)-Amidine-AmC(5)-Peptides Conjugates

Scheme 7

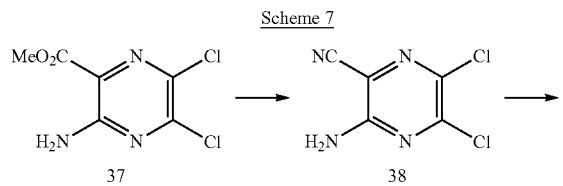

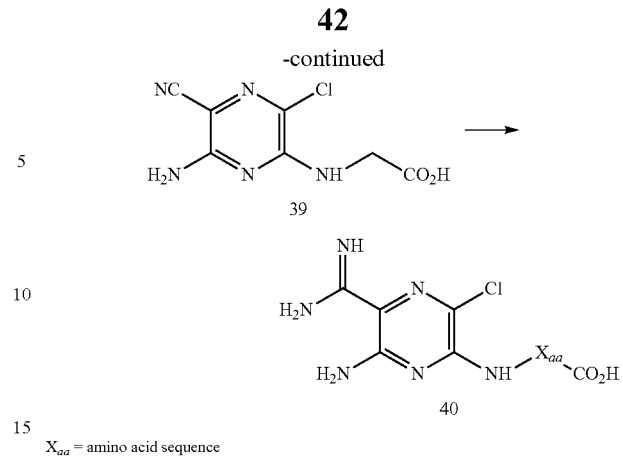

$X_{aa}$ = amino acid sequence

Intermediate 39 is synthesized by regioselective reaction of compound 38 with glycine. The nitrile moiety is converted to amidine by reaction with ammonia.

Synthesis of C(2)amid-Am-C(5)-Gly (40a):

Compound 40a is synthesized by reacting 39 with ammonia.

Synthesis of C(2)amid-Am-C(5)-Gly-Gly-Arg⊥OBn (40b):

As shown in Scheme 8, Compound 40b is synthesized by Boc protection of 40a followed by conjugation to uPA-specific sequences under EDC, HOBt coupling conditions and Boc deprotection with TFA.

Scheme 8

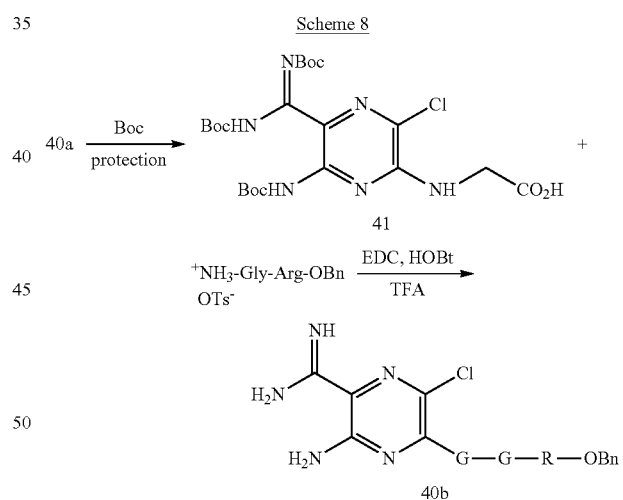

Synthesis of C(2)amid-Am-C(5)-Gly-Gly-Arg⊥Gly-OBn (40c):

Compound 40c is synthesized by reacting compound 41 with tosylate salt of NH$_3^+$Gly-Gly-Arg-Gly-OBn.

Synthesis of C(2)amid-Am-C(5)-Val-Gly-Arg⊥OBn (40d):

Compound 40d is synthesized by reacting compound 41a with a tosylate salt of NH$_3^+$Gly-Gly-Arg-OBn in the presence of EDC, HOBt coupling agents followed by deprotection with TFA. Compound 41a is synthesized by nucleophilic addition-elimination reaction of 38 with NH$_2$Val-OH, followed by protection with Boc group as shown in Scheme 9.

43

Scheme 9

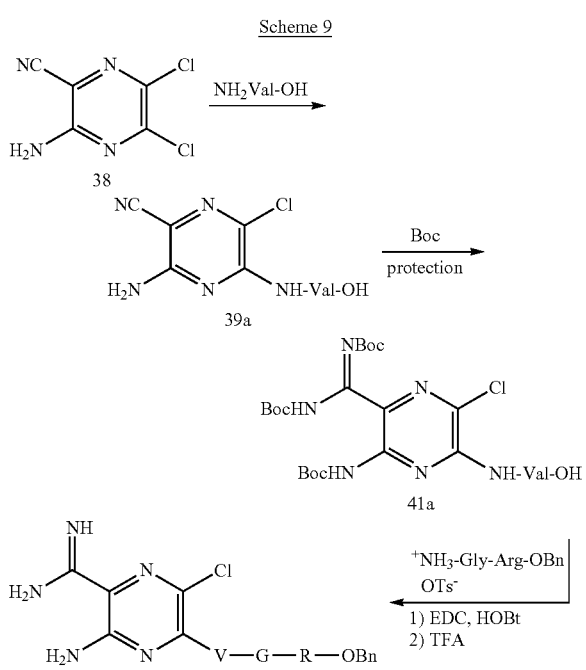

Synthesis of C(2)amid-Am-C(5)-Val-Gly-Arg⊥Gly-OBn (40e):

Compound 40e is synthesized by reacting 41a with a tosylate salt of NH₃⁺Gly-Gly-Arg-Gly-OBn in the presence of EDC, HOBt coupling agents followed by deprotection with TFA.

Example 6

Preparation of Peptide-Amidine-C(2)-AmC(5)-Amino Acid Conjugates

Scheme 10

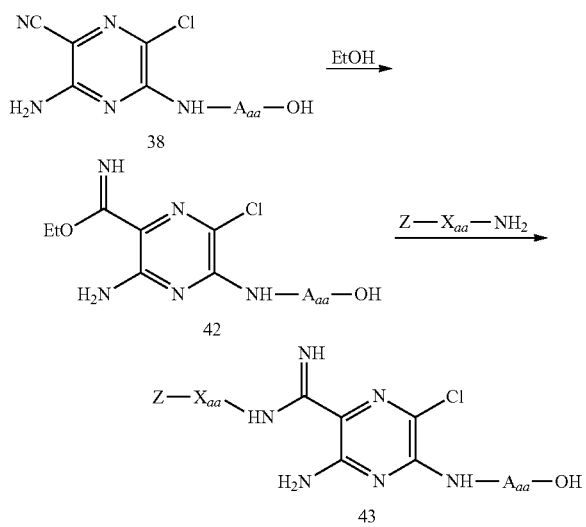

$A_{aa}$ = amino acid
$X_{aa}$ = amino acid sequence

44

Compound 43 is prepared according to the sequence shown in Scheme 10 by coupling compound 42 with a C-terminal protected peptide Z—$X_{aa}$—NH₂. Compound 42 is prepared by reacting compound 38 with anhydrous EtOH in the presence of HCl.

Synthesis of Z-Gly-Gly-Arg⊥C(2)amid-Am-C(5)-Gly (43a):

Compound 43a is synthesized by reacting compound 42 with Z-Gly-Gly-Arg-NH₂, where —NH-$A_{aa}$-OH is Gly.

Synthesis of Z-Val-Gly-Arg⊥C(2)amid-Am-C(5)-Gly (43b):

Compound 43b is synthesized by reacting compound 42 with Z-Val-Gly-Arg-NH₂, where —NH-$A_{aa}$-OH is Gly.

Example 7

Preparation of Peptide-Carboline Conjugates

Scheme 11

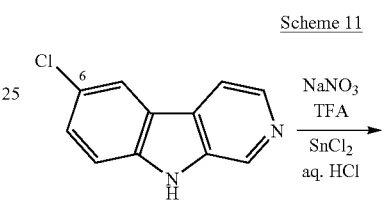

44

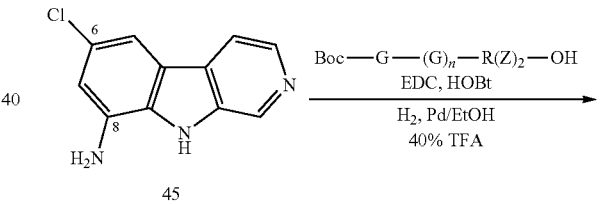

45

46: R = Boc-Gly-(Gly)$_n$-Arg(Z)$_2$-
47: R = Boc-Gly-(Gly)$_n$-Arg-
48: R = NH$_2$-Gly-(Gly)$_n$-Arg-

Peptide-carboline conjugates are prepared according to Scheme 11. Key amino-intermediate 45 is prepared by nitration of 6-chloro-b-carboline (44), followed by reduction. Compound 44 is readily prepared from norharman (Acros Organics) by electrophilic chlorination (NCS, THF, 48 h). Compound 46 (n=0, 1) is obtained by coupling 45 to short bis(Cbz-protected) Gly-Arg peptides featuring the uPA cleavage sequence. Compound 47 is generated by subsequent Cbz hydrogenolysis. Deprotection of Boc of compound 47 furnishes substrate 48.

Example 8

Preparation of AmC(5)-Peptide-Carboline Conjugates

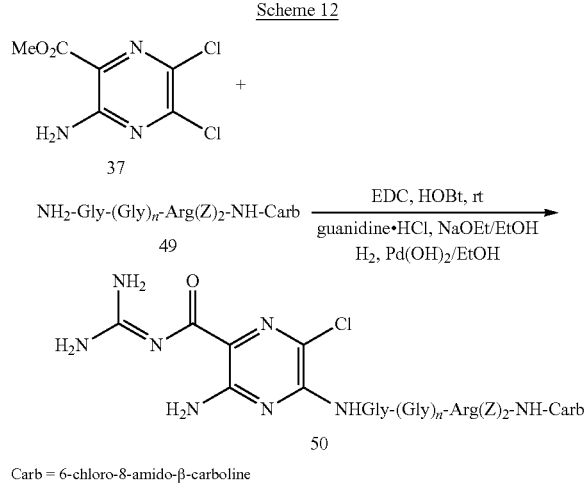

Carb = 6-chloro-8-amido-β-carboline

Peptide reagent 49 (see Scheme 15), prepared by selective Boc-deprotection (TFA) of carb-conjugate 46 is coupled to amiloride ester 37. Subsequent installation of the guanidine moiety using guanidine·HCl, followed by Cbz hydrogenolysis produced Am-C(5)-peptide-Carb conjugate 50 (the NH terminus of Gly is shown for clarity). Alternatively, peptide 49 can be directly and regioselectively coupled to C(5) of amiloride by reacting with pyrazine dichloride 20 using the method for the synthesis of Am-C(5)-peptide conjugates (Scheme 13).

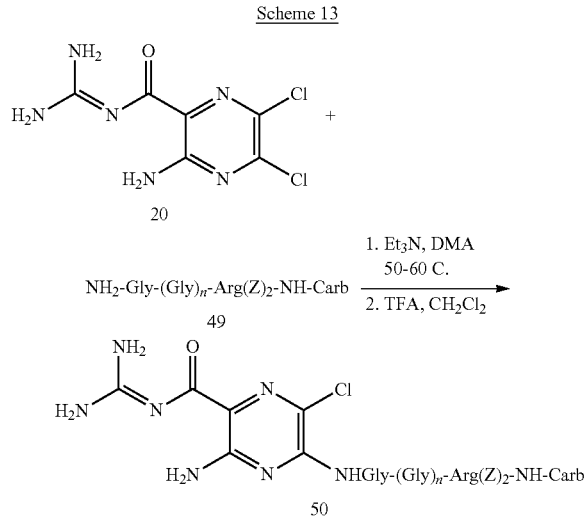

Example 9

Preparation of C(2)-amid-Am-C(5)-Gly-Gly-Arg-Carb Conjugate (52)

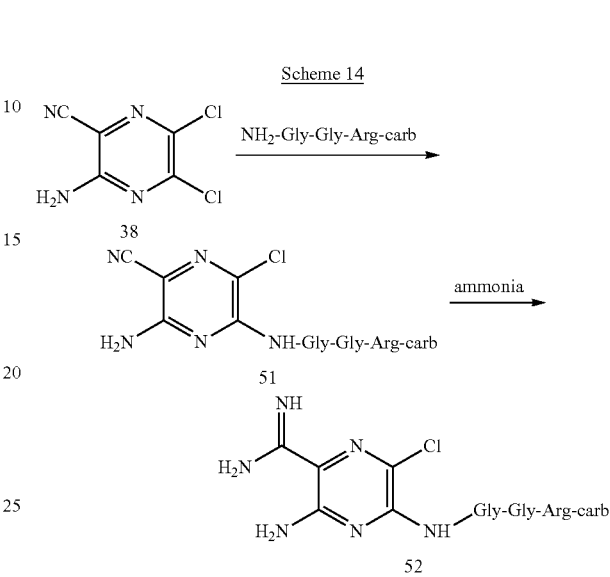

C(2)-amidine analog of compound (52) is readily prepared by coupling pyrazine dichloride 38 with NH$_2$-Gly-Gly-Arg-carb, followed by converting the cyano group to amidinyl group.

Example 10

Preparation of Carbo-X$_{aa}$-C(2)-amid-Am-C(5)-Gly-OH (54)

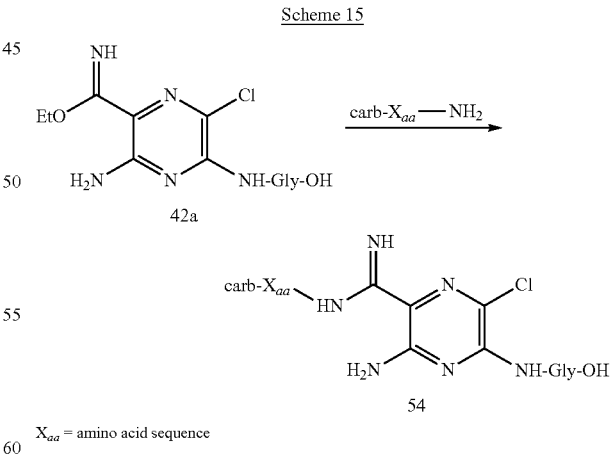

X$_{aa}$ = amino acid sequence

C(2) amidine peptide conjugate 54 is prepared by reacting imidate 42a with carb-X$_{aa}$NH$_2$ (wherein carboline is conjugated to the carboxy terminus of the amino acid sequence and NH$_2$ represents the amino terminus of the amino acid sequence).

Example 11

In Vitro Studies. Cell Permeation Studies of AmC(5)-Gly and AmC(5)Gly-OBn

The following examples show that amilorideC(5)-glycine-OH (AmC(5)-Gly) is a reversible and micromolar inhibitor of uPA and NHE-1. AmC(5)-Gly does not permeate cells, while AmC(5)-Gly-OBn is cell permeant. Amiloride and its derivatives are fluorescent, permitting visualization of the compound intracellularly using a quantitative fluorescent microscope (Palandoken, H., 2005. 312(3): p. 961-7. Epub 2004 Oct. 27). The fluorescent extinction coefficient of each compound is determined using a spectrofluorometer and permits semi-quantitative estimations of intracellular drug accumulation. As shown in FIG. 3C, the AmC(5)-Gly cannot be visualized intracellularly in glioma cells, while amiloride and alkyl and aromatic groups positioned at the C(5) position rapidly permeate cells (FIG. 3A, B, Palandoken, H., et al., 2005, Epub 2004 Oct. 27).

AmC(5)-Gly-OBn inhibits uPA and NHE1 with the same potencies of AmC(5)-Gly. Both AmC(5)-Gly-OBn and AmC(5)-Gly inhibit NHE1 and shrink glioma cell volumes in vitro and in intracerebral glioma xenografts as determined using small animal 7 tesla NMR.

Example 12

Figure 4A:
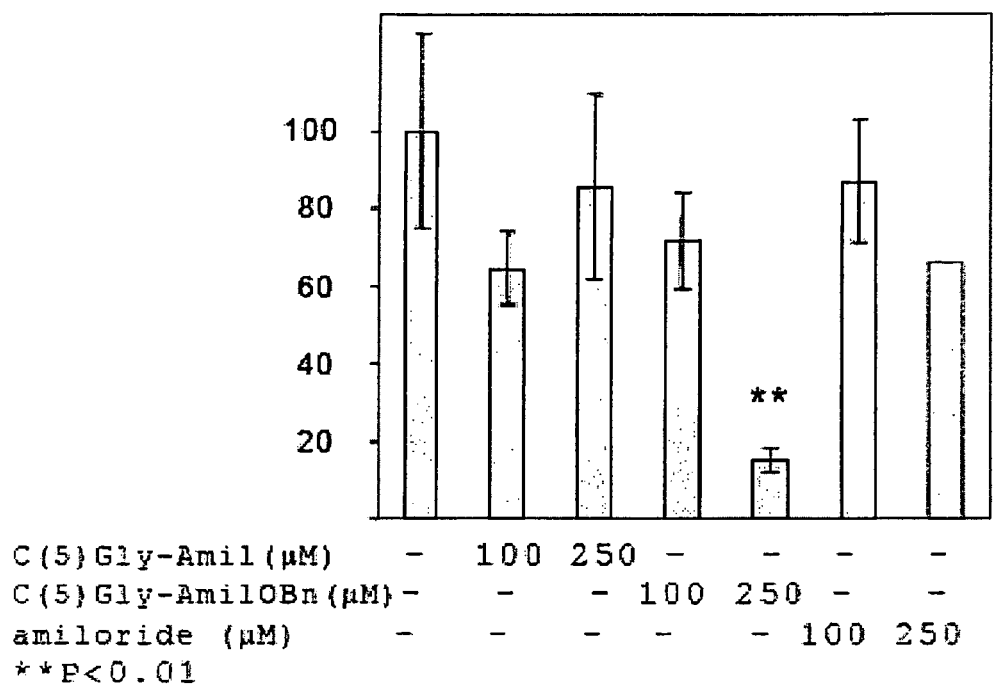
FIG. 4A: Adherence of Glioma to EMC after treated with AmC(5)Gly and AmC(5)Gly.

Inhibition of Glioma Attachment to Extracellular Matrix (ECM) by AmC(5)Gly-OBn As shown in FIGS. 4A and B and, U87 glioma cells in logarithmic growth were trypsinized and washed ×1 with PBS. 4×105 cells were plated on to each ECM-coated well that was treated as indicated. Cells were monitored for adherence to the ECM. The numbers of attached cells in each well were manually counted using interference microscopy after 4 hours when adherence was complete. Experiments were performed in triplicate for each treatment and data expressed as mean+S.D. **statistically signif at P<0.001. Glioma cell morphology 4 h after plating as visualized by phase contrast microscopy. Glioma cells treated with AmC(5)GlyOBn, but not AmC(5)Gly, demonstrated significant inhibition of adherence to ECM.

Structure-Activity Relationship Data.

Enzymatic assays using peptide-specific substrates demonstrate that amino acids conjugated to C(5) position of amiloride inhibit uPA, while peptide conjugates to C(5) amiloride are inactive as inhibitors of uPA, NHE1, and NCX (Palandoken, H., et al., Amiloride peptide conjugates: prodrugs for sodium-proton exchange inhibition. J Pharmacol Exp Ther., 2005. 312(3): p. 961-7. Epub 2004 Oct. 27). Amino acid or peptide conjugation to the C(2) guanidine moiety of amiloride also are inactive as uPA inhibitors.

Example 13

Comparison of the Intracellular Inhibition of uPA and Proliferation of U87 Glioma Cells by AmC(5)-Gly-OBn with its Impermeant Analog, AmC(5)-Gly AmC(5)-Gly-OBn is cell permeant prodrug that delivers AmC(5)-aminoacid intracellularly, where it accumulates because of its polarity following prodrug cleavage by intracellular uPA. AmC(5)-Gly-OBn impeded glioma cell adherence to ECM, inhibited proliferation, and caused subsequent glioma cell death by 48 h, in contrast to hydrophilic AmC(5)-Gly-OH. Removing AmC(5)-Gly-OBn at 24 h permitted glioma cells to resume proliferation. These observations indicate that despite comparable pharmacological profiles, intracellular access of AmC(5)-Gly-OBn is required to produce these biological effects.

Figure 4B:
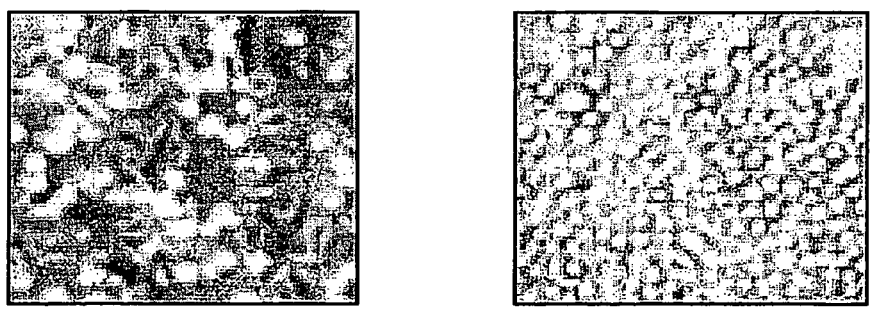
FIG. 4B: Microscopic images of morphology of glioma cells treated with AmC(5)Gly and AmC(5)Gly.
Figure 5:
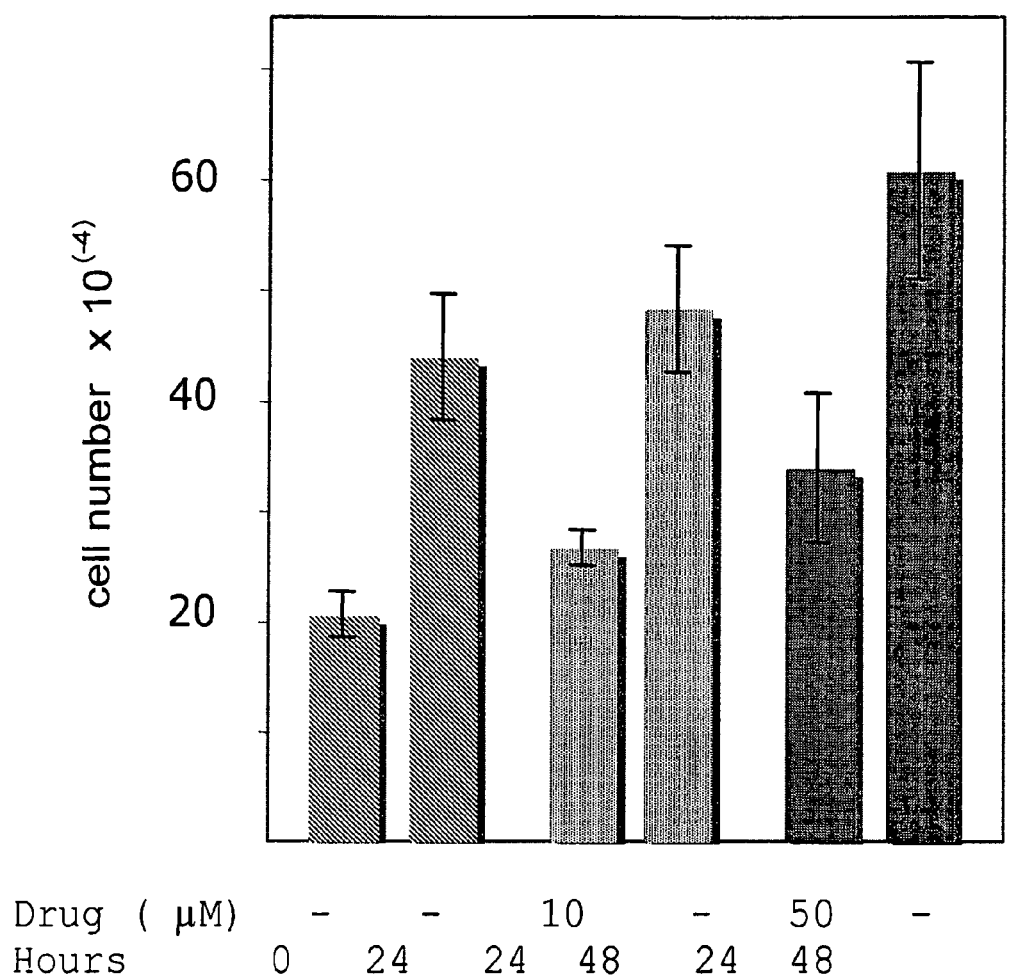
FIG. 5 illustrates the reduction of glioma cell numbers in the presence of BnO-C(5)gly-am conjugate and the increase of the tumor cells numbers in the absence of the compound.

AmC(5)-GlyOBn rapidly permeates cells, unlike AmC(5)-GlyOH. AmC(5)-GlyOBn selectively inhibits intracellular glioma uPA with $IC_{50}$=7.5 microM, does not inhibit tPA nor the gelatinases expressed by U87 glioma cells. AmC(5)-Gly-OBn interferes with glioma adherence to the extracellular matrix unlike the impermeant AmC(5)Gly (FIG. 4). In contrast, hydrophilic AmC(5)-Gly does not affect ECM adherence, proliferation, or viabilities of U87 glioma cells (FIG. 5, table 1).

Proliferation of U87 glioma cells was inhibited by AmC(5)-GlyOBn at 24 h. Following drug removal at 24 h, inhibition of proliferation was reversed by 48 h (FIG. 4). Manual cell counts, coupled with the trypan blue exclusion assay, determined the number of viable cells at 24 h and 48 h. Three separate experiments (n=6/exp) with S.D. as shown, *significance at P<0.01. Removal of AmC(5)-GlyOBn at 24 h caused cell numbers to increase by 48 h, as compared with U87 glioma cell numbers that continued to be treated with the drug for 48 h (Table 1).

TABLE 1

U87 proliferation and survival 48 h after treatment. Cells treated with drugs for 48 h with 10 determinations per treatment. Statistically significance at **P < 0.001 *P < 0.01

| Compound | % of control attachment at 4 h | cell numbers as % of controlat 48 h (WST assay) (% cell death, trypan blue) |
|---|---|---|
| Vehicle | 100 ± 18 | 100 (3) |
| Amiloride 250 micoM | 58 ± 12* | 31* (57) |
| AmC(5)GlyOBn 250 microM | 15 ± 5** | 6** (84) |
| AmC(5)Gly 250 microM | 85 ± 15 | 93 (5) |

Statistically significance at **P < 0.001 *P < 0.01

Cells treated with drugs for 48 h with 10 determinations per treatment. Following drug removal at 24 h, inhibition of proliferation was reversed by 48 h. Manual cell counts, coupled with the trypan blue exclusion assay, determined the number of viable cells at 24 h and 48 h. Three separate experiments were performed with n=6 with S.D. shown, *significance at P<0.01. Removal of AmC(5)-GlyOBn at 24 h caused cell numbers to increase by 48 h, as compared with U87 glioma cells that were treated with the agent for 48 h (6% of controls, FIG. 5 and Table 1).

Example 14

Death of U87 Glioma Cell in the Presence of AmC(5)Gly-OBn

AmC(5)-GlyOBn, but not AmC(5)Gly, caused U87 glioma cell demise at 48 h (table 1). Total live cell numbers per well were determined using a tetrazolium assay (WST). The WST live cell assay demonstrated an 84% reduction in viable cell numbers following treatment with AmC(5)GlyOBn after 48 h. Cell death was quantified in same wells using manual cell counts coupled with trypan blue exclusion assay (Hegde, M., et al., *Amiloride Kills Malignant Glioma Cells Independent of Its Inhibition of the Sodium-Hydrogen Exchanger*. J Pharmacol Exp Ther, 2004. 9: p. 9). Reduced numbers of live glioma cells, Measured with WST, closely corresponded with the number of dead cells after 48 h of treatment with either AmC(5)Gly-OBn and with amiloride (table 1). Control studies (not shown) demonstrated that formazon formation from WST corresponded with cell number for each glioma cell line and that the drugs did not affect formazon production, as compared with stage-matched controls (Table 1). Following treatment with either cell-permeant amiloride or AmC(5)Gly-OBn, there was a close correspondence observed between reduced adherence to ECM, reduced proliferation, and subsequent cell death at 48 h.

AmC(5)Gly-OH and AmC(5)Gly-OBn were designed and synthesized using SAR information about uPA inhibitors. Both amino acid conjugates of amiloride are comparable in their selective and reversible inhibition of intracellular uPA and NHE-1 in U87gliomas. AmC(5)Gly-OBn and amiloride, are cell permeant, and both compounds interfere with glioma cell adherence, inhibit proliferation, and induce subsequent glioma demise in cell culture and in intracerebral glioma xenografts. Neither compound produces neuropathological changes in normal brain cell elements in S-D and athymic rats when administered intracranially on a daily basis for up to 10 days. Behavioral side effects and seizures are observed with efficacious administration of amiloride, but not with AmC(5)Gly-OBn. AmC(5)Gly-OH does not permeate cells, but is comparable to AmC(5)Gly-OBn as a reversible inhibitor of uPA and NHE1 in the micromolar range. AmC(5)Gly-OH does not affect glioma cell attachment, proliferation, or demise but does reduce glioma cell volume because of its inhibition of NHE1 as described previously (McLean, L. A., et al., *Malignant gliomas display altered pH regulation by NHE1 compared with nontransformed astrocytes.* Am J Physiol Cell Physiol, 2000. 278(4): p. C676-88).

These in vitro results support the hypothesis that intracellular trapping of a hydrophilic AmC(5)amino acid permit the compound to achieve milimolar levels. Delivery of such a bioactive intracellular inhibitor could be achieved using a cell-permeant, inactive prodrug that is activated selectively by uPA.

Example 15

Peptides Conjugated to C(5) Position of Amiloride

Peptides conjugated to C(5) position of amiloride are inactive inhibitors of uPA, tPA, MMP-2, MMP-9, and sodium-ion transport exchangers, but have been demonstrated to be enzymatically cleaved in a selective fashion to generate bioactive amino acid conjugates to amiloride. A "[Leu]$^5$-enkephalin-like" amiloride prodrug was synthesized and evaluated its bioactivation using HPLC-MS (see Palandoken, H., et al., 2005 ibid.). This prodrug was selected because the peptide substrate requirements for enkephalinase (endopeptidase 24.11) are well characterized, the purified enzyme is commercially available and inexpensive, and peptide syntheses of the enkephalinase substrates were relatively straightforward. Amiloride C(5)-Gly-Gly-Gly-Phe-Leu Prodrug, These peptide conjugates to the C(5) amino group act as inactive prodrugs that do not inhibit uPA, MMP-2, MMP-9, tPA, NHE1, or NCX. When cleaved by endopeptidase 24.11 this peptide conjugate generates AmC(5)-Gly (see Palandoken, H., et al., 2005 ibid.). The addition of an extra glycine was required for steric reasons to permit selective enzymatic cleavage by enkephalinase and intracellular endopeptidases in U87 glioma cell homogenates completed the peptidase hydrolysis to the non-cleavable AmC(5)-Gly. The introduction of D-aminoacids served prevented endopeptidase cleavage and served as a negative controls (see Palandoken, H., et al., 2005 ibid.). Amiloride-aa1-aa2-aa3-R, permeates cells and can be engineered to be selectively cleaved by intracellular endopeptidasesto generate an impermeant amiloride-aa1 that accumulates intracellularly and selectively inhibits uPA in the microM range.

Amiloride has been coupled to glycine via the C2 guanidine moiety (C(2)Gly-Am), and at both the C5 and C2 positions (Gly-C(2)-Am-C(5)Gly). C(2)Gly-Am and Gly-C(2)-Am-C(5)Gly were synthesized with good efficiencies and are inactive as inhibitors of uPA, as is predicted by structure-activity data of benzoylguanidines (data not shown). However, these test compounds can be conjugated asymmetrically with small tri- and tetrapeptides to create R-peptide-C(2)-Am-C(5)aa1. The peptide conjugated to the C2 guanidine moiety can be cleaved by cellular endopeptidases to liberate Am-C(5)aa1 intracellularly.

Example 16

Effect of Amiloride Conjugates on Tumor (Glioma) Cell Proliferation and Cell Death: Intracerebral U87 Glioma Xenograft Studies Continuous intracranial amiloride infusion significantly slowed the growth rate of intracranial glioma xenografts (table 2). Glioma cell death was observed primarily in tumor regions adjacent to pseudopallisading cells bordering avascular perinecrotic regions. The volume of U87 glioma xenografts were measured at different postimplantation times using the small animal 7 tesla NMR facility on UC Davis campus. Growth rates of intracerebral human U87 xenografts followed Gompertzian kinetics (Rygaard, K. and M. Spang-Thomsen, *Breast Cancer Res Treat*, 1997. 46(2-3): p. 303-12) and the rate of tumor doubling decreased 3-fold following 5 days of continuous intracranial administration of amiloride (100 mM reservoir, 276 pmol/24 h, 1.4 nmol total, table 2)

Table 2.

Determining tumor doubling time (hrs) in U87 xenografts were measured using small animal NMR. Amiloride was infused 12-17 days after tumor implantation using an ALZET pump at high doses (100 mM reservoir, 276 pmol/24 h), low doses (10 mM reservoir), as compared with controls.

TABLE 2

Determining tumor doubling time (hrs) in U87 xenografts were measured using small animal NMR.

| | Doubling time | | | | | | |
|---|---|---|---|---|---|---|---|
| Day post implant | 10 | 12* | 15* | 17* | # of animals | # of measurements | R (gompertzian fit) |
| Control | 2.65 | 2.81 | 3.10 | 3.25 | 9 | 15 | 0.98915219 |
| Vehicle pump | 2.46 | 2.80 | 3.40 | 3.81 | 3 | 10 | 0.92141969 |

TABLE 2-continued

Determining tumor doubling time (hrs) in U87 xenografts were measured using small animal NMR.

| Day post implant | Doubling time | | | | # of animals | # of measurements | R (gompertzian fit) |
|---|---|---|---|---|---|---|---|
| | 10 | 12* | 15* | 17* | | | |
| 10 mM amiloride reservoir | 3.07 | 3.4 | 3.99 | 4.44 | 3 | 18 | 0.84935900 |
| 100 mM amiloride reservoir | 1.23 | 1.98 | 4.58+ | 11.65++ | 8 | 32 | 0.90521755 |

Amiloride was infused 12-17 days after tumor implantation using an Alzet pump at high doses (100 mM reservoir, 276 pmol/24 h), low doses (10 mM reservoir), as compared with controls Establishment and local invasion of Intracerebral Glioma xenografts are prevented or retarded by intracranial administration of AmC(5)-GlyOBn (FIG. 6). Small animal NMR demonstrates Gompertzian growth kinetics of intracranial human U87 glioma xenografts stereotaxically implanted in athymic rats (FIGS. 6. A & B). FIG. 6C. Once daily intracranial administration of AmC(5)Gly-OBn (300 pmol/d) was begun 1d postimplantation and continued through day 10.6/14 (43%) of xenografts failed to become established, while 8/14 (57%) tumors demonstrated a marked retardation in the initial rates of tumor growth (–) as compared with stage-matched vehicle-treated (–) and untreated controls (--). FIG. 6D. Pretreatment of athymic rats with intracranial AmC(5) Gly-OBn for 3 days prior to implantation achieved steady-state brain levels as measured by HPLC-fluorometry. Following glioma cell implantation, once daily intracranial administration was continued for 10 days. The mean tumor volume at 10d postimplantation, of 6 treated animals was <30% of the vehicle-treated controls (mean±SD).

Neuropathological changes were not observed in normal brain cell types of 250-280 gm Sprague-Dawley control rats that received 14 days of continuous intracerebral amiloride infusion (276 pmol/24 h) or athymic rats that received a single daily subarachnoid administration of 300 pmol of AmC(5)-GlyOBn for 10 days. For amiloride, parasaggital sections were stained with hematoxylin and eosin in addition to using specialized stains for neuronal damage (FluoroJade) and for myelinated fiber tracts (luxol fast blue). Intrathecal infusion of amiloride in S-D male rats did modestly affect spatial memory, and intermittent seizures were observed in 3 of 8 animals receiving amiloride infusion. There were no premature deaths.

As shown in Table 2, tumor doubling time (hrs) in U87 xenografts were measured using small animal NMR. Amiloride was infused 12-17 days after tumor implantation using an ALZET pump at high doses (100 mM reservoir, 276 pmol/d), low doses (10 mM reservoir), as compared with controls.

The volume of U87 glioma xenografts were measured at different postimplantation times using the small animal 7 tesla NMR facility on UC Davis campus. Growth rates of intracerebral human U87 xenografts follow Gompertzian kinetics (Rygaard, K. et al., *Breast Cancer Res Treat* 1997, 46(2-3): 303-12), and the rates of tumor doubling slowed by more than 3-fold following 5 days of continuous intracranial administration of amiloride (100 mM reservoir, 276 pmol/24 h, 1.4 nmol total, (–), as compared with vehicle- or untreated controls (---) (FIG. 6).

Example 17

Design, Synthesize, and Enzymatically Assess Prodrugs and their Activation by uPA to Generate a Trapped, Intracellar uPA Inhibitor Rationale: Establish, efficient syntheses of AmC(5)-peptide and Z-aa1-C(2)AmC(5)-aa2-OBn, where Z=benzyloxycarbonyl, to permit derivatives of these molecules to be used to create an inactive prodrug wherein uPA cleavage traps the polar C(5)-aa2 uPA inhibitor intracellularly. The objective is to retain critical components of amiloride nucleus that maintain specificity for uPA inhibition in microM range.

Strategy for Analyzing Prodrug Cleavage and Intracellular Trapping of Amiloride Conjugates:

Analyze the selectivity of prodrug cleavage by intracellular uPA (see Palandoken, H., et al., 2005 ibid.). Incubate compound with recombinant uPA and analyze cleavage products using HPLC-mass spectrometry as previously described incubating AmC(5)Gly⊥Gly-Gly-Phe-Leu with enkephalinase (see Palandoken, H., et al., 2005 ibid; and Palandoken, H. P. D., *Dissertation, I. Amiloride-peptide conjugates: Stealth inhibitors of cell surface ion exchangers. II. A facile synthesis of (tert-alkoxy)amines.*, in *Chemistry*. 2006, University of California, Davis. p. 41-49). Incubate compound with cellular homogenates from U87 glioma cells and analyze cleavage products using HPLC-MS. Incubate compound with conditioned media from U87 glioma cells and analyze cleavage products using HPLC-MS. Incubate compound with homogenate from intracranial glioma xenograft and perform HPLC-MS. As a negative control, incubate compound with homogenate from contralateral normal brain cortex. Examine extracellular bioactivation and degration of the prodrug by Infusing the compound into glioma xenograft using microdialysis threaded through stereotaxic needle track into intracerebral glioma xenograft. Determine the dialysis catheter placement within the xenograft using small animal NMR. Recover extracellular fluid and analyze dialysate using the fluorimeter and HPLC-MS to measure the ratio of extracellular cleavage of prodrug to intact prodrug generated by secreted uPA. These methodologies have be utilized with a commercial fluorogenic substrate for uPA, Bz-β-Ala-Gly-Arg-AMC. There is a ratio of <1:10$^4$.

Intracellular Trapping of Amino Acid Amiloride Conjugate

Figure 3:
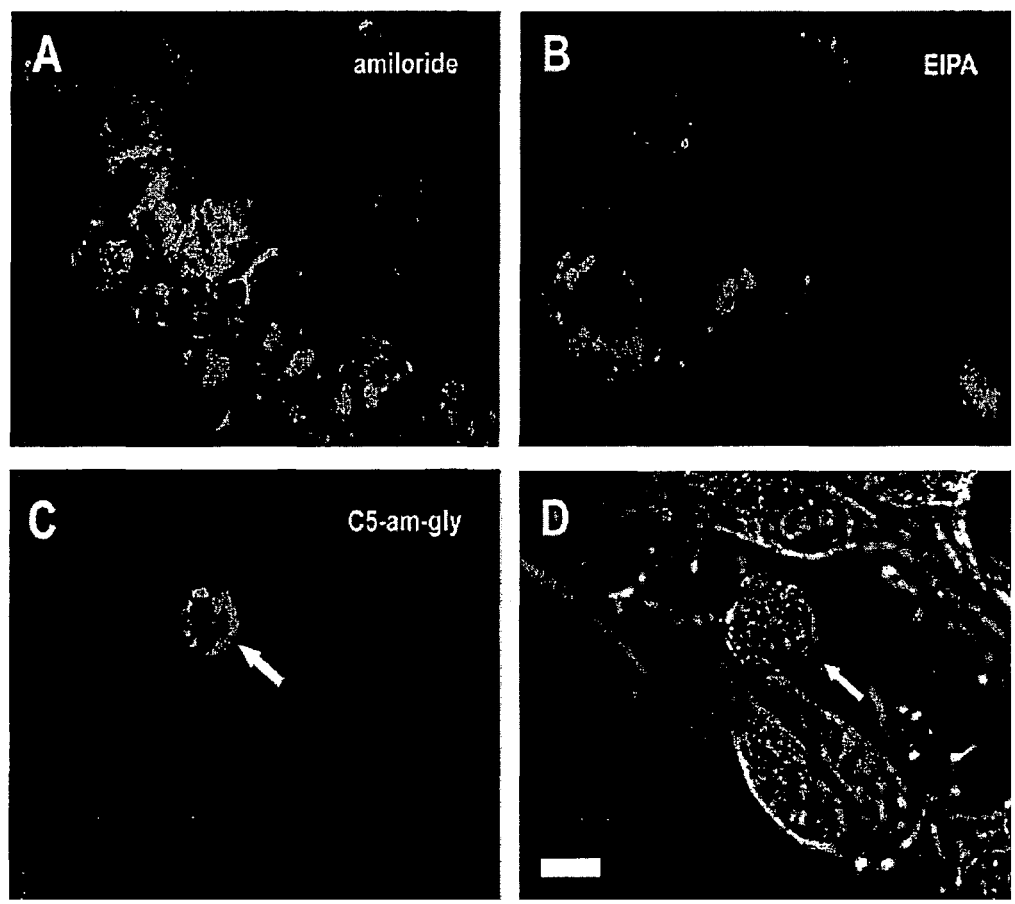
FIG. 3 shows fluorescent microscopy of U87 glioma cells following 90 min incubation with (A) 50 μM amiloride or (B) 50 μM ethylisopropylamiloride (EIPA); (C) fluorescent microscopy of U87 glioma cells following 180 min incubation with 50 μM of the hydrophilic AmC(5)-Gly. AmC(5)-Gly does not permeate glioma cells except for a single trypan-positive, dying or dead U87 cell (arrow); (D) Bright field microscopy image of the same cells as in (C) with the corresponding trypan-positive cell shown by an arrow (bar=10 μM).

Chemical nucleus of benzoylguanidine is highly fluorescent so that intracellular drug accumulation and retention in glioma cells can be visualized using semiquantitative fluorescent microscopy (FIG. 3). Quantitation of permeation and trapping of successful drug candidates subsequently utilizes commercially radiolabeled compounds. As a negative control utilize a homologous peptide analog conjugated to amiloride that contains a D-amino acid and which cannot be enzymatically cleaved. Extract cellular homogenates from 1a, 1b, 1d with dimethylacetamide, dry, perform HPLC-MS, and identify fragmentation products as previously described (see Palandoken, H., et al., 2005 ibid.).

Enzymatic Inhibition of Prodrugs and Cleavage Products.

Inhibitory potencies of the prodrug, its synthesized cleavage product, and of the activated prodrug following incubation with homogenates 1a-d are determined for the following enzymes; uPA and tPA. Inhibitory potencies of the above are determined against the following ion transporters; sodium-proton exchanger (NHE-1) and the sodium-calcium exchanger (NCX 1.1). Indirect effects on plasminogen activation, gelatinases (MMP-2, MMP-9), osteopontin and uPA expression, are determined for the prodrug, its synthesized cleavage product, and of bioactivated prodrug.

Biological Screening of Bioactivated Prodrugs and their Bioactive Derivatives (Steps 1-3)

Figure 7:
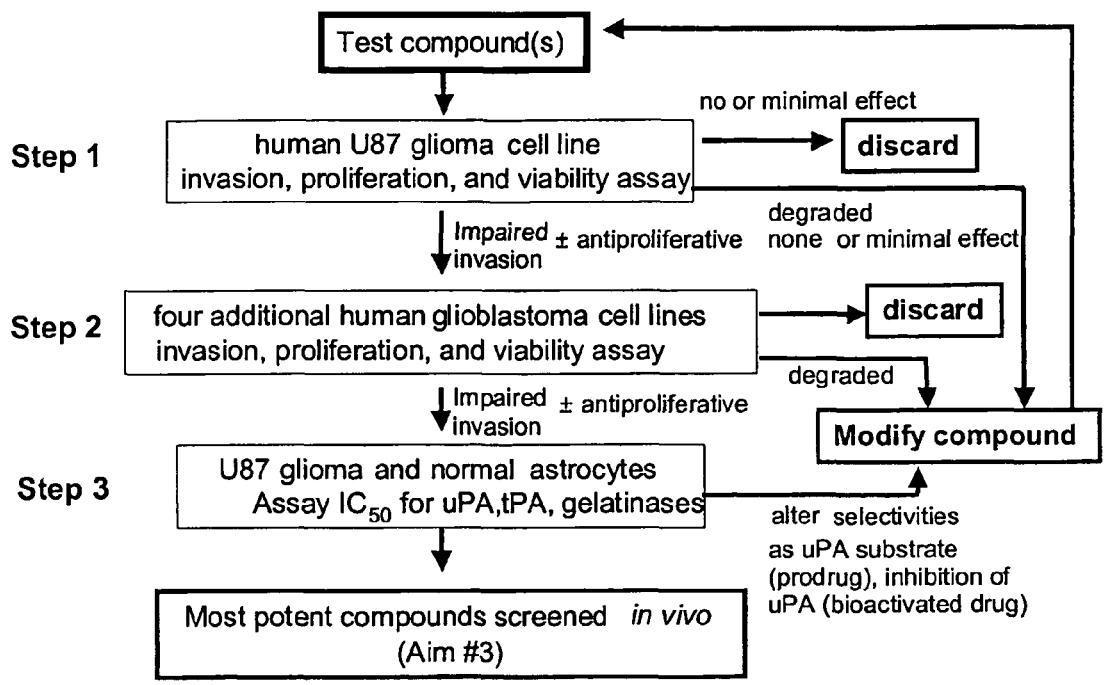
FIG. 7 illustrates the screening strategy in 5 glioma cell lines of compounds that are cleaved by uPA, selectively inhibit uPA, and accumulate intracellularly.

Agents are determined using a panel of human glioma cell lines (see methods below) and in normal astrocytes for stability, toxicity and ability to inhibit {1} ECM adherence, {2} proliferation {3} invasion and {4} initiate cell death (see methods and (Hegde, M., et al., *Amiloride kills malignant glioma cells independent of its inhibition of the sodium-hydrogen exchanger*. J Pharmacol Exp Ther, 2004. 310(1): p. 67-74)). Furthermore, compounds are incubated for up to 72 h in cell extracts and with conditioned cell culture media and assessed for overall stability using LC-fluorometry as part of step 1. The most efficacious compounds obtained from screening the glioma cell line panel are then be evaluated using intracerebral glioma xenografts using intracranial administration (FIG. 7). Prodrugs and derivatives are initially screened with HPLC-MS using glioma cell and astrocyte cell extracts and by incubating compounds in glioma-conditioned cell culture medium to determine stability (steps 1,2). Prodrugs and activated derivatives are screened in a dose-dependent fashion on U87 glioma cells to assess their inhibition of ECM adherence, proliferation, and cytotoxic effects (step 1). The most bioactive compounds are screened using four additional genotypically diverse, human malignant glioma cell lines and in primary astrocytes (step 2). Biological efficacies of compounds (steps 1 & 2) are determined by measuring their inhibitory potencies, relative to amiloride, of uPA, tPA, plasmin activation, MMP-2, MMP-9, NHE, NCX, in U87 glioma cells and in primary astrocytes (step 3).

Human Glioma Cell Lines to Assay Attachment, Invasion, Proliferation, and Cell Death.

The human glioma cell lines, isolated from patients with glioblastoma multiformans, were obtained from ATCC. PTEN mutants (U87MG, U118, U373MG, U251MG) and PTEN wildtype (LN229) have been reported as intracerebral xenografts in athymic rats and mice. MMP-2 and uPA expression is increased in U87MG, U118, U373MG, and U251MG and their cell growth is characterized by a lack of contact inhibition in vitro. Sugisaki's group employs U87MG, U373MG, and U251MG for invasion studies (Yoshida, D., et al., *Tracking cell invasion of human glioma cells and suppression by anti-matrix metalloproteinase agent in rodent brain-slice model*. Brain Tumor Pathol, 2002. 19(2): p. 69-76) and U87 MG is routinely employed (Valster, A., et al., *Cell migration and invasion assays*. Methods, 2005. 37(2): p. 208-15). A subclone of U87MG glioma cells is stably transfected to express green fluorescent protein (GFP), while maintaining normal growth kinetics as an intracerebral xenograft. U251MG and U373MG cells can be transfected in a similar fashion with GFP. These GFP-expressing glioma subclones are employed for in vivo migration studies and facilitate stereological measures of glioma cell migration in brain slices using laser confocal microscopy as has been described (Yoshida, D., et al., *Tracking cell invasion of human glioma cells and suppression by anti-matrix metalloproteinase agent in rodent brain-slice model*. Brain Tumor Pathol, 2002. 19(2): p. 69-76; Akella, N. S., et al., *A novel technique to quantify glioma tumor invasion using serial microscopy sections*. J Neurosci Methods, 2006. 153(2): p. 183-9). Extracts from rat brain and normal cultured primary cortical astrocytes are as negative controls.

Amino acids conjugated to the C(2) and C(5) positions of amiloride and peptide conjugates to the C(5) position were synthesized with high overall yields. Glycine was conjugated to the C(2) and C(5) positions of amiloride with yields exceeding 50% utilizing standard peptide coupling regimens (Palandoken, H. P. D., *Dissertation, I Amiloride-peptide conjugates: Stealth inhibitors of cell surface ion exchangers. II. A facile synthesis of (tert-alkoxy)amines.*, in *Chemistry.* 2006, University of California, Davis. p. 41-49).

Enzymatic Inhibition and Biological Activation of Prodrug.

Test compounds, described in data, demonstrate that AmC (5)-Gly-OH and AmC(5)-Gly-OBn selectively inhibit uPA but not tPA or the gelatinases. The permeable AmC(5)-Gly-OBn inhibits glioma cell ECM attachment, invasion, proliferation, and causes tumor cell death by 48 h. AmC(5)-Gly-OBn has no effect on normal primary astrocytes or normal brain cell types when administered intracranially for 13 days. This is consistent with SAR data of amiloride's selective inhibition of uPA with $IC_{50}$=3-10 microM (Vassalli, J. D. and D. Belin, *Amiloride selectively inhibits the urokinase-type plasminogen activator*. FEBS Lett, 1987. 214(1): p. 187-91). The feasibility of prodrug activation was demonstrated with an 'enkephalin-like' amiloride analog that was cleaved selectively by purified neutral endopeptidase 4.2.2, and by glioma cell extracts to generate AmC(5)-Gly (see Palandoken, H., et al., 2005 ibid.; and Palandoken, H. P. D., *Dissertation, I. Amiloride-peptide conjugates: Stealth inhibitors of cell surface ion exchangers. II. A facile synthesis of (tert-alkoxy) amines.*, in *Chemistry.* 2006, University of California, Davis. p. 41-49).

Peptide Derivatives Frequently Need Modification in Order to be Clinically Effective.

The introduction of D-amino acids, N-methyl amino acids, or cyclic amino acid derivatives is commonly employed to prevent cleavage by endogenous peptidases. "Peptidomimetism" introduces hydrocarbon bonds that retain the confomeric structure of the peptide backbones, while retaining critical amino acid sidechains to overcome problems of peptide instability, poor absorption, and rapid metabolism. The drawbacks of peptide pharmaceuticals do not eclipse the fact that combinatorial peptide syntheses can easily generate novel sets of compounds to optimize efficacies using high throughput, tetrazolium-based screening assays of viable cell numbers of glioma cells and primary astrocytes.

Functional Assays.

In vitro assays for attachment, migration, proliferation and cell death have been used (Hegde, M., et al., *Amiloride Kills Malignant Glioma Cells Independent of Its Inhibition of the Sodium-Hydrogen Exchanger*. J Pharmacol Exp Ther, 2004. 9: p. 9). Laser confocal microscopy (Gorin, F., et al., *Perinecrotic glioma proliferation and metabolic profile within an intracerebral tumor xenograft*. Acta Neuropathol (Berl).

2004. 107(3): p. 235-44. Epub 2004 Jan. 8) and stereological methods has been used to measure proliferative and cell death indices in glioma xenografts, and confocal microscopy is used to quantify the numbers and distances of glioma cells from their stereotaxic injection site.

Example 18

Selective Cleavage of C5am-Gly-Peptide Conjugates

This example shows the results of enzyme degradation assays performed on the C5am-Gly conjugates from Example 14 (see, Scheme 1, compounds 3a-c). Compound 3b is a C5am-Gly-peptide conjugate containing two D-amino acids, and compound 3c is a C5 am-Gly-peptide conjugate coupled to a peptide to generate an analog of opioid peptides that cross the blood brain barrier (BBB). The resultant conjugates (compounds 3a-c) were tested for selective cleavage by the brain peptidase enkephalinase (neutral endopeptidase 24.11; Calbiochem) via incubation for 24 h in the presence or absence of the enzyme, and aliquots from the reaction solutions were then analyzed by LCMS to identify the C5am-Gly conjugate (compound 3a), starting material, and enzymatic cleavage products (see, Scheme 3). As negative control experiments, the conjugates were analyzed following treatment with (1) bovine pancreatic trypsin (Calbiochem) or (2) the buffer solutions without enzymes.

Scheme 16

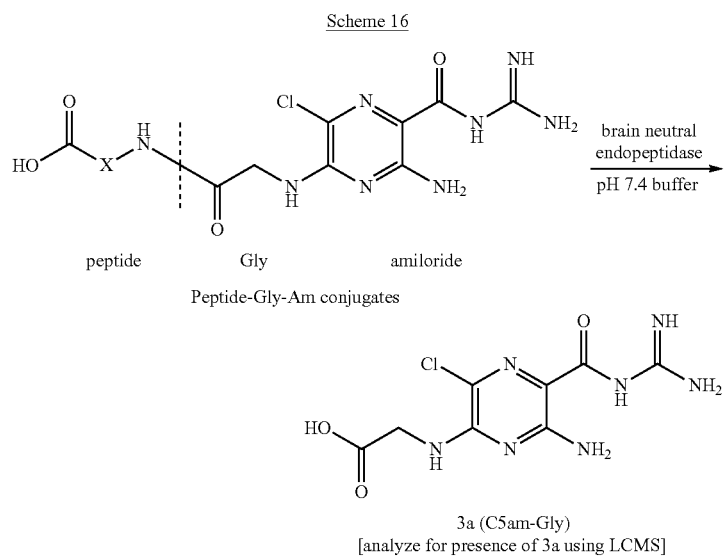

3a (C5am-Gly)
[analyze for presence of 3a using LCMS]

The results from the enkephalinase and trypsin digests of C5am-Gly-peptide conjugates are shown in Table 3. Compound 3a (C5am-Gly) was unaffected by enkephalinase, trypsin, or control (buffer) digestion. Compound 3b (C5am-Gly-D-Ala-Gly-Phe-D-Leu-OH) was not cleaved by either of the enzymes or in the control (buffer) due to the presence of D-amino acids in the peptide. Compound 3c (C5am-Gly-Gly-Gly-Gly-Phe-Leu-OH) was designed to be a peptide analog of the Leu-enkephalin family of peptides and was selectively cleaved by enkephalinase, generating the predicted C5am-Gly cleavage product. However, as a negative control, treatment of compound 3c with trypsin did not generate C5am-Gly.

TABLE 3

C5am-Gly conjugates tested in the LCMS enkephalinase assay.

| Conjugate (am = amiloride core) | Structure | MS data[a] |
|---|---|---|
| 3a (C5am-Gly) | [structure shown] | 288.1 (3a parent)[b] 254.1 (M − Cl)+ |

TABLE 3-continued

C5am-Gly conjugates tested in the LCMS enkephalinase assay.

| Conjugate (am = amiloride core) | Structure | MS data[a] |
|---|---|---|
| 3b (C5am-Gly-D-Ala-Gly-Phe-D-Leu-OH) | 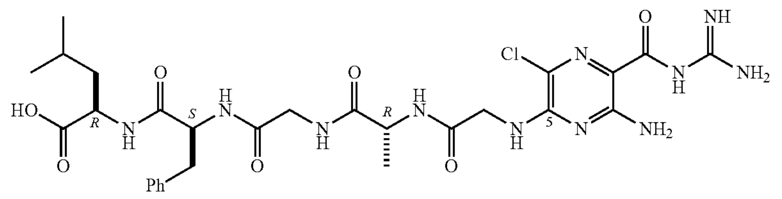 | 676.4 (3b parent)[b]<br>642.4 (M − Cl)[+]<br>288.1 not observed |
| 3c (C5am-Gly-Gly-Gly-Gly-Phe-Leu-OH) | 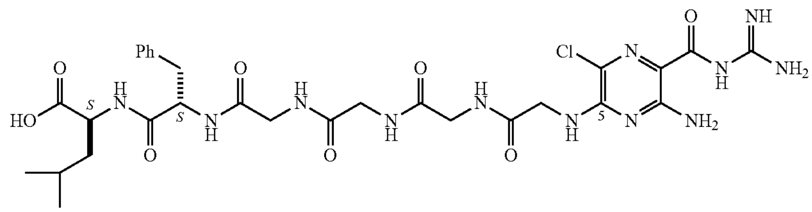 | 719.3 (3c parent)[b]<br>288.1 (C5am-Gly) |

[a]after incubation 6 h;
[b]observable Cl isotope signal

C(5)am-Gly (compound 3a) is considerably more hydrophilic than most amiloride derivatives, a property that restricts its activity to the cell surface (e.g., less toxicity). However, C(5)am-Gly can also be coupled to more hydrophobic peptides, such as a Leu-enkephalin peptide, that are transported across the BBB into the brain (e.g., greater accessibility). The specific enzymatic hydrolysis of compound 3c by enkephalinase demonstrates the feasibility of designing additional C5am-Gly-peptide conjugates that are selectively cleaved by either brain-specific enzymes, tumor-specific enzymes (e.g., matrix metalloproteinases), or enzymes activated during tissue injury (e.g., calpains, caspases) to liberate the more polar C5am-Gly compound.

Experimental Methodologies

In Vitro Enzymatic Studies:

uPA, tPA, and MMP-2 and MMP-9 enzymatic activities secreted by and contained within glioma cell lines, normal astrocyte cultures, primary rat brain, and intracranial glioma xenograft homogenates are measured using commercial peptide analog substrates, that become fluorescent when enzymatically cleaved. Recombinant tPA was obtained from ASSAYPRO, CT1001. Secreted and intracellular single chain uPA (sc-uPA, pro-uPA) and HMW-uPA forms of urokinase-type plasminogen activator are detected using a commercial ELISA with the lower detection limit being 10 pg uPA/mL (America Diagnostica #894).

Sodium-proton type 1 (NHE1) and sodium-calcium transport (NCX) measurements in glioma cells. Inhibition of NHE in glioma cell lines using BCECF and quantitative fluorometry are routinely measured (McLean, L. A., et al., *Malignant gliomas display altered pH regulation by NHE1 compared with nontransformed astrocytes*. Am J Physiol Cell Physiol, 2000. 278(4): p. C676-88). $IC_{50}$ of NCX transport bidirectionally is measured using whole cell patch clamping bidirectional NCX inhibition using a HEK-293 cell line transfected with NCX 1.1 obtained from J. Lytton (Dong, H., J. Dunn, and J. Lytton, *Stoichiometry of the Cardiac Na+/Ca2+ exchanger NCX1.1 measured in transfected HEK cells*. Biophys J, 2002. 82(4): p. 1943-52).

HPLC-MS is performed at the Molecular Structure Facility at UC Davis, on a recharge basis, and performs MS/MS, and MALDI-TOF on a routine basis. Our lab performs reverse phase HPLC-analytic and prep using HPLC (Waters 1525EF) in series with UV and fluorometric detectors.

In Vitro Cell Adhesion and Spreading Assay.

To study adherence, wells in 24-well plates are coated with 200 ul of PBS (CMF Dulbecco's) containing one of the following ECM substrates: {i} MATRIGEL {ii} vitronectin {iii} fibronectin {iv} lamininin-5. Plates are incubated 1 h at 37° C. then wells are washed once with prewarmed serum-free DMEM and the drug added to each well. Each treatment group, consisting of pretreated glioma cells ($3 \times 10^3$ cells/well) is plated into 6 wells, and adhesion is evaluated at 60 min intervals over a 6-18 hour period, depending of the cell line. Unbound cells are gently dislodged with Dulbecco's PBS, while counting adherent cells in 10 random fields per each well under 10× magnification using an inverted microscope with interference phase optics and an ocular grid (21 $mm^2$). During the same time intervals, the percent value of spread cells with respect to adherent cells is evaluated.

In Vitro Cell Proliferation Assays.

Tetrazolium Live Cell Assay.

WST is secreted from glioma cells that can be reduced in attached and detached live cells to formazon that is detected spectrophotometrically. Formazon formation has been determined to be proportional to glioma cell number for U87MG, U251, U373, and primary astrocytes. Absorbances are measured at 570 nm using a microtiter plate reader. Mean background absorbances of cell-free media (630 nm) are subtracted from these values. Manual Cell counts are coupled with trypan dye exclusion assays (Hegde, M., et al., *Amiloride kills malignant glioma cells independent of its inhibition of the sodium-hydrogen exchanger*. J Pharmacol Exp Ther, 2004. 310(1): p. 67-74). Identical concentrations of glioma cells are grown until 50% confluent on 60 mm plates. Following drug treatments, floating cells in media are collected and combined with adherent cells that were harvested following 0.25% v/v trypsin for 5 minutes (37° C.). The combined fractions are centrifuged at 350×g for 5 min. The resultant cell pellet is resuspended in equal volumes of PBS-CMF with 0.4% trypan blue. 10 µL aliquots of the suspension are plated on a hemocytometer, and cells counted 5 minutes after staining (Hegde, M., et al., *Amiloride Kills Malignant Glioma Cells Independent of Its Inhibition of the Sodium-Hydrogen Exchanger*. J Pharmacol Exp Ther, 2004. 9: p. 9).
In Vitro Cell Migration Assay.

Glioma cells are experimentally treated using MATRIGEL Invasion Chambers (BECTON DICKINSON). Chambers are hydrated for >2 h in the tissue culture incubator with 500 microL DMEM in the bottom of the well and in the top of the chamber. After hydration of the MATRIGEL, the DMEM in the bottom of the well is replaced with DMEM containing 10% FBS. 2-4×10$^4$ glioma cells are plated in 500 µl DMEM supplemented with 10% FBS in the top of the chamber. The invasion assay is carried out for 24 h in the tissue culture incubator. The cells are fixed by replacing the culture medium in the bottom and top of the chamber with 4% para-formaldehyde in PBS. Chambers are rinsed in PBS and stained with 0.2% crystal violet for 10 min. Chambers are washed 5 times in beaker of ddH$_2$O. The blue cells at the top of the MATRIGEL membrane are removed with Q-tips. Cells in bottom chamber are counted using an inverted microscope (Valster, A., et al., *Cell migration and invasion assays*. Methods, 2005. 37(2): p. 208-15). When using GFP-expressing glioma cells, migration into the bottom chamber is quantified using an inverted fluorescent microscope. In vitro assays for adherence, spread, invasion, and proliferation, provide approximate estimations of a drug's ability to alter the attachment, invasion, and proliferation of intracerebral human glioma cells stereotaxically injected in toe corpus striatum.

Example 19

Evaluate the Most Biologically Active and Glioma-Specific Compounds Using Intracerebral Glioma Xenografts Compounds that inhibit cellular uPA impede glioma cell adherence, plasmin activation, local invasion, proliferation, and angiogenesis within human glioma intracerebral xenografts.

Rationale:

High grade glioma cells express high levels of OPN, uPA, and uPAR leading to plasminogen activation that corresponds with tumor invasiveness (Saihia, B., et al., *Molecular pathways triggering glioma cell invasion*. Expert Rev Mol Diagn, 2006. 6(4): p. 613-26; Said, H. M., et al., *Response of the plasma hypoxia marker osteopontin to in vitro hypoxia in human tumor cells*. Radiother Oncol, 2005. 76(2): p. 200-5) and recurrence (Zhang, X., et al., *Expression and significance of urokinase type plasminogen activator gene in human brain gliomas*. J Surg Oncol, 2000. 74(2): p. 90-4).

Athymic rats lack a functional T-cell system capable of mounting a host versus graft rejection of the human intracerebral xenograft and permits more accurate assessment of drug efficacies against intracerebral glioma xenografts (Barth, R. F., W. Yang, and J. A. Coderre, *Rat brain tumor models to assess the efficacy of boron neutron capture therapy: a critical evaluation*. J Neurooncol, 2003. 62(1-2): p. 61-74). Athymic rats are pretreated intracranially with either a cell-permeant version of the bioactive drug or the cell-permeant, inactive prodrug until steady-state brain levels are reached (see below, step 2). A human glioma cell line that expresses green fluorescent protein (e.g. U87-GFP) is injected stereotaxically into to the corpus striatum. The animals continue intrathecal treatment and small animal NMR measures intracranial tumor volumes at 6 and 10 days postimplantation for adherence, proliferation, and local invasion. Another set of U87 glioma xenografts are followed out to 14 days postimplantation when these xenografts consistently develop neovascularity. Animals are injected i.p. with BrdU 48 h prior to death, then deeply anesthesized, and killed by intracardiac perfusion of 4% paraformaldehyde. Treated animals are compared with vehicle-treated controls (10 microL DMSO), and the following parameters determined: (1) tumor volume, (2) local tumor invasion from the injection site, (3) proliferative indices, (4) neovascularity, (5) glioma cell death and (5) neuropathological changes in normal brain cell types.

Figure 1B:
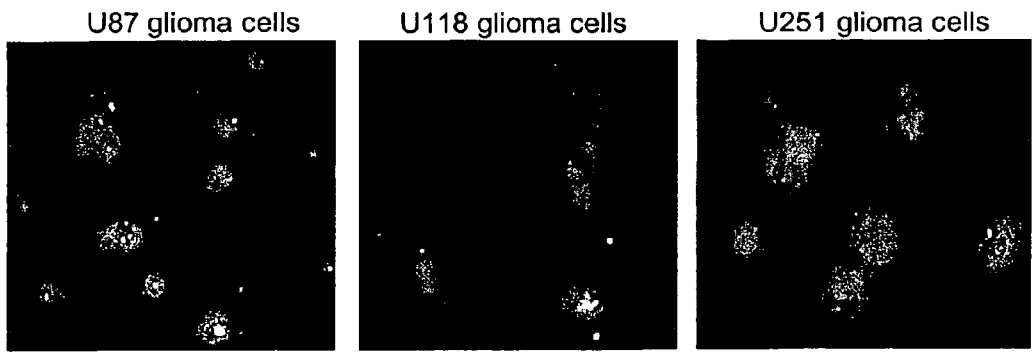
FIG. 1B shows several glioma cell lines internal cleaving of a uPA peptide based substrate or prodrug and generating fluorescent AMC.
Figure 2:
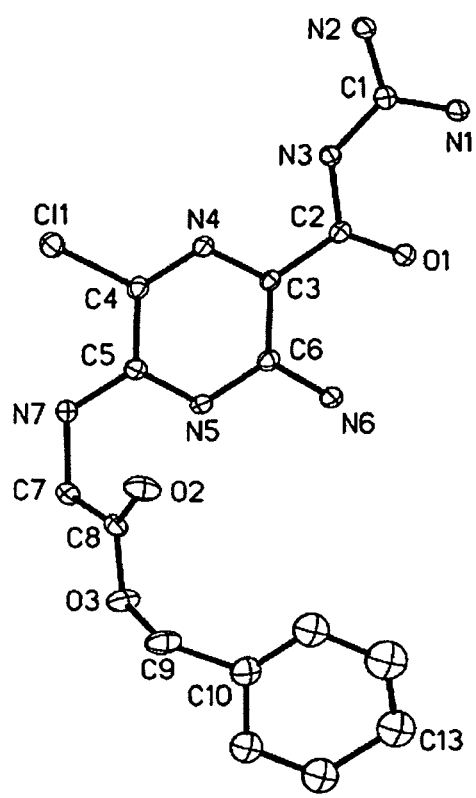
FIG. 2 shows an X-ray crystal structure of C(5)-amino acid conjugate 3a as its benzyl ester.

Prodrugs are evaluated in vivo following evaluation for high efficiency selective cleavage by intracellular uPA using a panel of five glioma cell lines and normal primary astrocytes (FIG. 1). Bioactivated compounds that inhibit (1) glioma cell adherence (2) plasminogen activation (3) migration and (4) proliferation are evaluated in vivo.

Compounds are preliminarily screened for stability using fresh rat brain extracts and analyzed by HPLC-MS. If stable, compounds are intracranially administered (subarachnoid space) and their accumulation in brain, cerebrospinal fluid, and blood of Sprague-Dawley rats are determined over a 14-day period (step 2). Levels of the prodrug, the bioactivated compound, and drug metabolites are measured by HPLC-MS.

Dosing and scheduling of intracranial administration of the compounds using intracerebral U87-GFP glioma xenografts are based upon the pharmacokinetic measurements (step 3).

Glioma Recurrence Model.

When steady-state brain levels of the bioactive compound have been achieved, implantation of GFP-expressing U87 glioma cells (2×10$^4$ cells/rat) are injected into 10 athymic rats. An additional 10 vehicle-treated animals are also implanted identically from this same suspension of U87-GFP cells. The animals continue to receive intracranial drug administration and NMR determines tumor volumes at days 6, 10, and 14 postimplantation.

Stereological methods, determine tumor volumes postmortem and using inverted laser confocal microscopy quantifies the migration of fluorescent U87 glioma cells from the needle injection site. The extent of invasion along white matter tracts of U87-GFP cells, relative to their injection site, is also quantitated stereologically (Valster, A., et al., *Cell migration and invasion assays*. Methods., 2005. 37(2): p. 208-15) (Akella, N. S., et al., *A novel technique to quantify glioma tumor invasion using serial microscopy sections*. J Neurosci Methods., 2006. 153(2): p. 183-9. Epub 2006 Jan. 6).

Glioma cell proliferative indices is measured using BrdU with a fluorescent secondary (Gorin, F., et al., *Perinecrotic glioma proliferation and metabolic profile within an intracerebral tumor xenograft*. Acta Neuropathol (Berl). 2004. 107 (3): p. 235-44. Epub 2004 Jan. 8) and compared with Ki67. The extent of neovascularization, stained by alkaline phosphatase, is compared to normal cerebral vasculature stained by GLUT-1 (Gorin, F., et al., ibid) or infusion with FITC-labeled tomato lectin (Blouw, B., et al., *The hypoxic response of tumors is dependent on their microenvironment*. Cancer Cell, 2003. 4(2): p. 133-46).

Neurotoxicities of biologically efficacious compounds are evaluated in step 4 and are comprised of: (1) General health and behavioral studies. Daily body weights are assessed in drug-treated and vehicle-treated rats during and following 12 day treatment protocols. There are a minimum of 10 animals per group. A daily neurotoxicity behavioral sign checklist is performed (72). A battery of standardized behavior tests include quantitative measures of vestibulomotor function, fine motor coordination, ambulation, and spatial memory. (2) Neuropathological surveys. Cytological studies are performed in the same drug-treated and vehicle-treated rats at the conclusion of behavioral testing. Surveyed brain regions are influenced by symptomotology (e.g. ataxia, spasticity), but routinely include: parasaggital and coronal tissue blocks of the nucleus caudatus, putamen, dentate gyrus, cerebellum, primary somatosensory cortex, cingulate gyrus, and brainstem regions that include the inferior olives, and the vestibular nuclear complex. Assessment of brainstem white matter tracts includes the spinocerebellar, vestibulospinal, corticospinal, spinothalamic. Two individuals, trained in neuropathology, review neuropathology slides independently in a double-blinded fashion.

The most efficacious and non-toxic compounds determined from steps 2-4 are intracranially administered using four additional intracerebral xenograft glioma models, representing PTEN mutant (U87, U373, U251) and PTEN wild-type (LN229) (step 5). Analyses described in step 5 for U87 xenograftsare performed using additional glioma xenograft models, and treated animals are compared with stage-matched, vehicle-treated controls.

A survivability study is performed for the most efficacious compound(s) determined from steps 1-5 by employing intracranial infusion into U87 intracerebral glioma xenografts.

Example 20

Neurobehavioral and Neuropathology with Intracranial Infusion of S-D Rats

Neurotoxicities of biologically efficacious agents are evaluated using the behavioral assessments and neuropathological surveys described in the Preliminary Results during intracranial amiloride and AmC(5)GlyOBn infusions. Each experimental and control group described below consist of a minimum of 10 animals per group. Experimental Design. The in vivo toxicity studies initially employ single, daily intracranial infusions of the candidate compound into a group of Sprague-Dawley rats for 13 days. Treated S-D animals are compared to a group of 10 control animals receiving intracranial drug vehicle injections. The infused drug concentration is based upon the cell line studies and adjusted for the low protein content of the cerebrospinal fluid which is 0.2% that of serum. Animals are behaviorally assessed for toxicity. In terminal experiments brains are removed at days 4, 6, 8, 10, and 12 days and frozen to determine levels of amiloride conjugates and possible degradation products using LC-MS. Behavioral assessments are conducted as described in Preliminary Results. General Health and Behavioral Studies. Body weights and behavioral parameters are assessed daily in drug-treated and vehicle-treated rats during 12 day treatment paradigms. Currently, standardized behavior tests are used, which include quantitative measures of vestibulomotor function, fine motor coordination, ambulation, and spatial memory. A daily neurotoxicity behavioral sign checklist (72) to detect neurological signs of toxicity and seizures is also performed. Acquisition of spatial memory is particularly sensitive for detecting subtle drug toxicities (Preliminary Results). Body weight is used as a measure of general health. Neuropathological Studies: Cytological studies are performed in the same drug-treated and vehicle-treated rats at the conclusion of behavioral testing. Fixation and sectioning techniques are described in the Experimental Methods section. Hematoxylin and eosin are used routinely to survey for neuropathological changes. Luxol fast blue stains myelin tracts to evaluate potential white matter changes. The surveyed brain regions are influenced by symptomotology, but include: parasaggital and coronal tissue blocks of the nucleus caudatus, putamen, dentate gyrus, cerebellum, primary somatosensory cortex, cingulate gyrus, and brainstem regions that include the inferior olives, and the vestibular nuclear complex. Assessment of brainstem white matter tracts with luxol fast blue staining includes the spinocerebellar, vestibulospinal, corticospinal, spinothalamic. Specialized stains for reactive astrocytes, neuronal chromatolysis, etc. are added if brain lesions are detected. These stains include Fluoro-Jade to detect neuronal degeneration (84), and GFAP immunostaining for glial fibrillary acidic protein as a sensitive detection for reactive glial responses. Potential Problems and Alternatives. Behavior studies that compared the motor performance and spatial memory performance of amiloride treated- and vehicle-treated rats that were implanted with intracerebral glioma xenografts have been completed. These studies demonstrated that amiloride infusion did not alter motor performance compared with vehicle- and untreated animals. However, there were problems with spatial memory that persisted throughout the nine day infusion period. These behavioral studies indicate the need to behaviorally assess treatment of the glioma tumor models.

Intracranial Infusion of Test Compound(s) into Intracerebral U118 and U373 Glioma Xenografts (Step 5).

Analyses of tumor doubling times and regional glioma cell death following treatments as described in Section 3 for U87 xenografts.

Survivability of Human U87 Glioma Xenografts.

Figure 9:
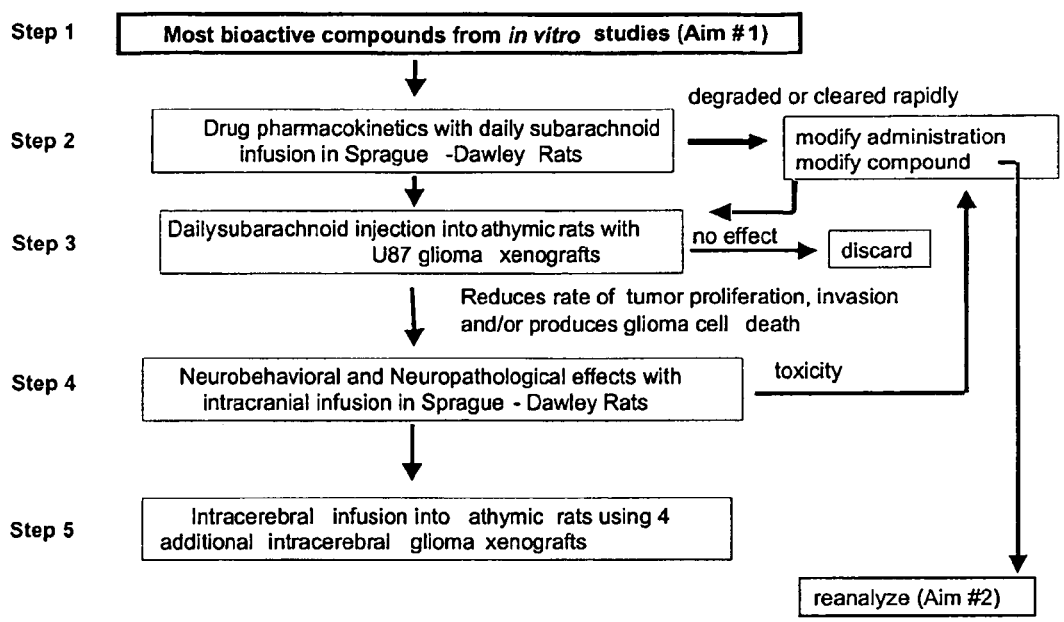
FIG. 9 illustrates a schema for screening bioactive compounds using intracerebral glioma xenografts. Prodrugs are evaluated in vivo (step 1) following evaluation for high efficiency selective cleavage by intracellular uPA using a panel of five glioma cell lines and normal primary astrocytes. Bioactivated compounds that inhibit (1) glioma cell adherence (2) plasminogen activation (3) migration and (4) proliferation are evaluated in vivo.

A survival study is performed using the human U87 glioma for those amiloride conjugates that prove efficacious and non-toxic in steps 3-5 (FIG. 9). The intracranial drug infusion protocol follows that of amiloride suppression of an established U87 xenograft tumor (Preliminary results). The efficacy of drug treatment is assessed by the survival rate of animals at each day postimplantation. Based upon published survival studies of the U87 glioma xenograft model, it is anticipate that 10 athymic rats per treatment group are compared against sham- and vehicle-treated animals (Table 4).

TABLE 4

Survivability studies using established tumors in human U87 glioma xenograft model. The percent of surviving animals in the treatment groups (n = 10 per group) is compared with sham- and, vehicle treatment groups.

| Glioma Model | vehicle-treated suppression of established tumor | Amiloride conjugate #1 | Amiloride conjugate #2 | Amiloride conjugate #3 |
|---|---|---|---|---|
| U87 | 10 | 10 | 10 | 10 |
| TOTALS | — | — | — | 50 |

Statistical Analyses.

Sample sizes for proposed experiments were determined by power analysis using an acceptable level of statistical power (80) to reliably detect treatment effects. Data from our preliminary studies and previous experience in our laboratories indicated approximate treatment effect magnitudes and variability of dependent measures. Alpha level for Type I error was set at 0.05 for rejecting null hypotheses. Suppression of tumor volume by NHE1 inhibitors, stereological counts of cytological markers, and dose-response effects of individual drugs are analyzed with one-way (Treatment Group) ANOVA followed by post hoc Dunnett's test for comparison of individual treatments to control. Differences in survival duration between controls and drug-treated groups for in vivo experiments are compared using the Cox-Mantel analysis.

Overall Experimental Design:

Table 11 summarizes the number of rats estimated to assess in vivo drug efficacies and neurotoxicological studies.

TABLE 11

Estimates of Sprague Dawley and Athymic rats for drug efficacies, neurotoxicity, and survival studies

| Animal models | Initial Drug Pharmacokinetics (step 2) | Intracranial infusion of cmpd into U87 glioma xenografts (step 3) | Neuro-behavioral Neuro-pathological effects (step 4) | Intracranial infusion of the most efficacious compounds into additional glioma xenografts (step 5) | Survival studies with intracranial infusion of most efficacious compounds (step3-5) |
|---|---|---|---|---|---|
| Sprague-Dawley controls | N~14 cmpds 4 animals per compound total 56 | na | N~10 cmpds 6 animals per compound total 60 | | |
| Intracerebral U87 xenografts using athymic rats | na | N~10 compounds 6 animals per cmpd total 60 | na | | N~3 cmpds 10 animals per compound (table 3.1) total 50 |
| Intracerebral U118 xenografts using athymic rats | na | | | N~4 cmpds 10 animals per cmpd total 40 | |
| Intracerebral U373 xenografts using athymic rats | na | | | N~4 compounds 10 animals per cmpd total 40 | |

Total Sprague-Dawley rats over 5 years: 92
Total Athymic (nude) rats over 5 years: 158
cmpds = estimated number of amiloride-based derivatives to be tested based upon screening in Aim #2

Experimental Methodologies

Intracerebral Glioma Xenograft Model:

Rats (250-280 gm) are intubated with 4% isoflurane and air:$O_2$ (2:1), maintained on 2% isoflurane, and placed into a Kopf stereotactic apparatus. Glioma cells at are harvested at 80% confluence, trypsinized, and then washed three times in sterile, isotonic phosphate buffered saline. Cells are counted in a hemocytometer and diluted to a final concentration of $1 \times 10^4$ cells per microL. 5 microL of glioma cells ($5 \times 10^4$) are stereotaxically injected into a 0.5 mm pocket made by a 23 gauge needle in the left anterior corpus striatum (−1 mm bregma, +4 mm left lateral, −5.0 mm depth) under sterile conditions in a laminar flow hood.

Animal Preparation.

Immediately following stereotaxic tumor implantation, rats (250-280 gm) are fitted with a plastic cannula guide that extended 2 mm below the surface of the skull to instill the drug directly into the subdural space via a borosilicate cannula (PLASTICS ONE, Roanoke, Va.). The cannula and guide construction are non-paramagnetic and permits spectroscopic imaging of the animals before and during drug infusion. Utilizing tumor growth kinetics, animals with intracerebral C6 tumor xenografts of 60-80 mm$^3$ volumes were selected for amiloride infusion.

NMR spectroscopy.

Prior to imaging the rats are administered 0.5 cc of OMNISCAN gadodiamide intraperitoneally (NYCOMED). The rats are anesthetized by face mask with a 1.5% isoflurane and 0.5 l/min oxygen, placed prone in a Lucite holder and secured by thin strips of adhesive tapes. A gradient recalled echo sequence is obtained which furnished a single slice in sagittal, coronal, and transverse orientations ('triplot') and which served as a scout image to ensure proper positioning of the animal. Spectroscopic images are obtained with a 7 Tesla (300 MHz) BRUKER BIOSPEC 70/20 system with a 210 mm horizontal bore equipped with B-GA12 shim coils driven by BRUKER Shim Power Supply with a maximum of 2A of current for each shim. S116 birdcage design resonator coil (maximum current: 100 A and maximum voltage: 150V) of 72 mm maximum sample diameter with gradient strength of 200 mT/mm was used for both. T1-weighted images (TR/TE=500/20 msec) are obtained using the standard spin echo sequence in the transverse, sagittal as well as in the coronal direction. The 2 mm slice thickness encompasses a 64 mm by 64 mm field of on a 128×128 matrix, and rendered 25 mm$^2$ per pixel resolution. Multiple contiguous slices separated by 1 mm are collected using 3 sinc pulses each of 2 msec duration, and which cover the entire tumor in one scan. The average scan time is approx 60 sec for the entire T1-weighted protocol.

Cytological Staining.

The cytological markers are well established in several models of brain injury and in glioma xenografts. Whenever possible, confirmatory markers on adjacent brain sections to assess their relative sensitivities are utilized. Errors in detection sensitivities of these cytological markers are systematic, as indices of apoptosis, necrosis, and proliferation between the treatment and control groups are compared. Nissl staining provides a high contrast image of glioma cells for determination of tumor volume. Bromodeoxyuridine labeling. Rats are injected intraperitoneally with BrdU (60 mg/kg) 1 h before intracardiac perfusion with 4% paraformaldehyde to label proliferating cells. The 4 μm sections are immunostained with an FITC-labeled, polyclonal antibody against GFAP (1:10, 000) followed by a cyan-labeled, polyclonal antibody against BrdU (1:1000) as described (87). Hematoxylin and eosin was reviewed and felt to remain as an excellent stain to identify and index necrotic neurons and astrocytes when used at 200× magnification (Fix, A. S., et al., *Integrated evaluation of central nervous system lesions: stains for neurons, astrocytes, and microglia reveal the spatial and temporal features of MK-801-induced neuronal necrosis in the rat cerebral cortex*. Toxicol Pathol, 1996. 24(3): p. 291-304). Fluorescent nuclear stain Hoescht 3222 and DAPI have been successfully used to identify apoptotic and necrotic glioma cells treated respectively with staurosporine or amiloride (1).

Stereological Methods.

Rats are deeply anesthetized with sodium pentobarbitol (75 mg/kg, i.p.) followed by intracardiac perfusion with phosphate buffer saline followed by 4% buffered paraformaldehyde. Brains are removed and postfixed in 2% paraformaldehyde at 4° C. for 24 h and then paraffin embedded or placed into sucrose prior to storage at −80° C. (Appendix C). Postfixed brains are cryoprotected in sucrose, and sectioned at 40 □m on a cryostat. These thicker sections are stained with a Nissl stain and tumor volume of sequential sections calculated by Cavalieri's method (Michel, R. P. and L. M. Cruz-Orive, *Application of the Cavalieri principle and vertical sections method to lung: estimation of volume and pleural surface area*. J Microsc, 1988. 150(Pt 2): p. 117-36).

Tumor Volumes.

Cavalieri's method estimates the volume of a structure (in our case, glial tumor) by measuring the area of the structure in a number of evenly spaced "two-dimensional" sections. In our in vivo tumor model, the procedure involves a systematically random collection of 10 sections evenly spaced through the entire tumor. To perform this, the brain is cut into 40 micron coronal sections and every section is collected to encompass the entire tumor. When the anterior most portion of the tumor becomes visible in the series of sections, a die is thrown to determine if the first, second, third, fourth, or fifth section from that point should be the initial section saved for staining and area analysis. Henceforth, every tenth section is stained and tumor area measured. This ensures that each section through the tumor has an equal probability of being analyzed. Tumor area is estimated with suitable precision by applying to each section a point grid with a known area associated with each point (a/p). Tumor volume (V) is then calculated using the formula: $V=(T)\cdot(a/p)$ delta $P_i$; where T=distance between sections, P=points landing on the tumor on the ith section. The grid generation and volume calculations are performed with STEREOLOGER (Version 1.0) software on a Windows-based system connected to a NIKON E600 microscope with motorized xyz stage controller (ASI MS-2000). Tumor volumes are described as mean volumes ($mm^3$)±S.D. Quantitative Measurements of Cell Counts. Unbiased cell counting is performed using the optical fractionator stereological method (Mayhew, T. M., et al., *Quantitative analysis of factors contributing to expansion of microvillous surface area in the coprodaeum of hens transferred to a low NaCl diet*. J. Anat., 1992. 181(Pt 1): p. 73-7). This method is based on the principle that the number of cells in a whole object (glioma) can be accurately estimated by counting the number of cells in a known fraction of the object. The volume of the area of interest is first calculated by the Cavalieri principle described above. The STEREOLOGER software divides the area of interest on each slide into "dissectors" which are small volumes of tissue (e.g., 25×25×20 μm) from which the cell counts are made. It is only necessary to count approximately 10% of the dissectors to arrive at accurate estimates of the number of cells in the entire object. The software randomly selects the dissectors to be counted. Quantitative Measurements of Glioma Cell Counts migrated from needle track. STEREOLOGER "dissector" software is utilized to quantify glioma number and lateral distance from the needle track marking the tumor injection site as described by Berens et al. (Valster, A., et al., *Cell migration and invasion assays*. Methods., 2005. 37(2): p. 208-15).

Glioma Xenograft Invasion Studies:

U87 glioma cells are again implanted into the corpus striatum of athymic rat brains and typically infiltrate widely throughout the ipsilateral hemisphere of the brain. Following treatment with a uPA inhibitor, one would predict glioma cells to be more confined to the implantation site and remain closer to local vasculature (Salajegheh, M., A. Rudnicki, and T. W. Smith, Appl Immunohistochem Mol Morphol, 2005. 13(2): p. 184-9). Furthermore, the anti-angiogenic and antiproliferative consequences of inhibiting the uPA/plasmin system would be predicted to decrease the rate of tumor growth. Tumor-bearing rats are injected i.v. with FITC-labeled tomato lectin that stain blood vessels in green, and then heart-perfused with 4% paraformaldehyde (PFA). Human U87 glioma cells over express cyclin D1 in all cell cycle stages and the anti-human cyclin D1 monoclonal antibody has successfully stained glioma cells that are proliferating or arrested in G1 phase. Tumor cells are assessed for their distance from blood vessels and neovascularization are quantified in vessels labeled with FITC-labeled tomato lectin using criteria described by Bergers and co-workers (Le, D. M., et al., J Neurosci, 2003. 23(10): p. 4034-43).

Assessment of Behavioral Effects:

These behavioral studies are routinely performed on rats who have sustained experimental traumatic brain injury or stroke.

Beam Walk:

Components of fine motor coordination are assessed using a beam-walking task. 24 h prior to tumor implantation, rats are trained to escape a bright light and loud white noise by traversing an elevated narrow wooden beam (2.5×100.0 cm) to enter a darkened goal box at the opposite end of the beam. Performance for each day is the mean latency of three trials to traverse the beam.

Morris Water Maze:

Acquisition of reference memory spatial learning/memory performance is assessed with a Morris water maze task. The test apparatus consists of a large white circular tank (220 cm diameter by 60 cm high) filled with water to a depth of 21 cm. Water temperature is maintained at 26±2° C. A transparent circular escape platform (12 cm diameter, 19 cm high) is placed in fixed position in the tank 2 cm below the water surface. Consistent visual cues are located in the test room outside of the maze. Placing the rat in the water close to, and facing the wall of the tank in one of the four cardinal start locations begin each trial. Rats are allowed 120 sec to find and mount the escape platform. Rats receive 4 trials/day over 5 consecutive days. Data is recorded using a video tracking system (Poly-Track, San Diego Instruments). Performance for each day is the mean latency of four trials to find the platform.

Neurotoxicity Behavioral Signs:

A standard behavioral checklist (Chang, in *Neurotoxicology* A.-D. M. B., Ed., CRC Press, pp. 223-252 (1993)) is performed daily to determine neurotoxic effects that might be missed with the above quantitative behavioral tests. Animals that exhibit one or more of the principal signs (Table 6) for three consecutive days are terminated from further testing and euthanized.

TABLE 6

Neurotoxicity and Behavioral Signs

| Principal Endpoint | Signs (any one sign for 2 consecutive days constitutes an endpoint) |
|---|---|
| MOTOR | Activity Changes |
| | Uncoordination |
| | Weakness and paralysis |
| | Abnormal movement and posture |
| | Tremor |
| SENSORY | Primary sensory deficits |
| | Pain |
| | Equilibrium disorders |
| AROUSAL OR REACTIVITY | Increased irritability or reactivity; change in CNS excitability |

Drug Measurements in Blood, Cerebrospinal Fluid, and Brain Tissue. Frozen brain homogenates have been spiked with amiloride and caffeine standard. Dimethylacetamide extraction has been determined to reproducibly recover 70% of the amiloride from brain pulverized in liquid nitrogen and that LC-MS could measure the amount of amiloride accumulating in brain tissue during 12 days of intrathecal infusion using an ALZET pump (Prelim Data).

Statistical Analyses.

Body weight, beam walk, and Morris water maze assessments are analyzed with repeated measures ANOVA (Treatment Group×Days) with assessment days as the repeated variable within subjects. When ANOVA is significant, post hoc Dunnett's test for comparison of individual treatments to control is performed.

HPLC-MS:

HPLC-fluorimetry and HPLC-MS is used to measure levels of amiloride and AmC(5)GlyOBn in brain tissue and cerebrospinal fluid with fmol sensitivities. HPLC-MS is used to identify cleavage products of the C(5)-Am-hexapeptide incubated with enkephalinase (see Palandoken, H., et al., 2005 ibid.). Initial stability and pharmacokinetic information assist with dosage ranges and administration schedules for the intracranial infusion of the compounds into U87 intracerebral glioma xenografts (step 3). Where indicated, commercially prepared, radiolabeled amino acids or peptides are incorporated into the most therapeutically promising amiloride conjugates to assess their intracerebral stability and kinetics in year 05.

Histology:

Necrotic glioma death produced by amiloride and AmC(5)GlyOBn in U87 intracerebral xenografts have been identified with eosin and HOECHST 3222, a fluorescent nuclear stain. GLUT-1 immunostaining occurs in U87,U251, U118 and that C6 glioma cells bordering perinecrotic regions that are stained by eosin have been reported (Gorin, F., et al., Acta Neuropathol (Berl). 2004. 107(3): p. 235-44. Epub 2004 Jan. 8). Glioma cells that have undergone DNA duplication have been identified using BrdU administered prior to intracardiac perfusion-fixation (Gorin, F., et al., Acta Neuropathol (Berl). 2004: 107(3): p. 235-44. Epub 2004 Jan. 8). Anti-phospho-H2Ax antibodies have been successfully employed (courtesy of Bradbury UC Davis Dept Biochemistry) to immunostain nicked nuclear dsDNA in dying or dead glioma cells that stained either with trypan blue or Sytox Green (Unal, E., et al., *DNA damage response pathway uses histone modification to assemble a double-strand break-specific cohesin domain*. Mol. Cell., 2004. 16(6): p. 991-1002).

Vertebral Animals:

Anesthetic and analgesic regimens are designed to minimize pain and discomfort. All surgery and acute experiments are done under general anesthesia. These protocols cover all the procedures performed on normal and immunodeficient rats described herein. Power analyses have determined that the number of rats in each proposed experiment is the minimum number required to reliably detect treatment effects.

The rats are housed in a controlled-environment animal room containing only one species in an AAALAC-accredited animal facility at U.C. Davis. Rats have free access to food and water and are on a 12-hour light/dark cycle. Sterile operating procedures (mask, gloves, autoclaved instruments and cannulas) are used in all surgical procedures.

Example 21

1. Activation of Prodrug by Intracellular uPA in Glioblastomas uPA is synthesized as pro-uPA. It has been demonstrated that human U87 glioma cells, used for in vivo xenograft studies, have considerable uPA activity in cell homogenates obtained from cells washed 2× with PBS. However, endogenous uPA inhibitors are disrupted with homogenization so uPA activity in intact human glioblastoma cell lines was examined. A cell permeant, non-fluorescent uPA substrate, Z-G-G-R-AMC, fluoresces when cleaved by active uPA. Intact glioma cells were incubated with Z-G-G-R-AMC for 90 min and then washed ×2 with PBS. Intact U87, U118, U251 human glioma cell lines demonstrate considerable intracellular fluorescence generated by the cleaved AMC group when visualized with a semi-quantitative fluorescent microscope as described previously. These data convincingly demonstrate that intracellular uPA in glioma cells is sufficient to cleave a peptide-based substrate or prodrug, such as Z-G-G-R-AMC or Z-G-G-R-C(5)amiloride.

Example 22

AmC(5)GlyOBn Permeation of Glioma Cells

Figure 10A:
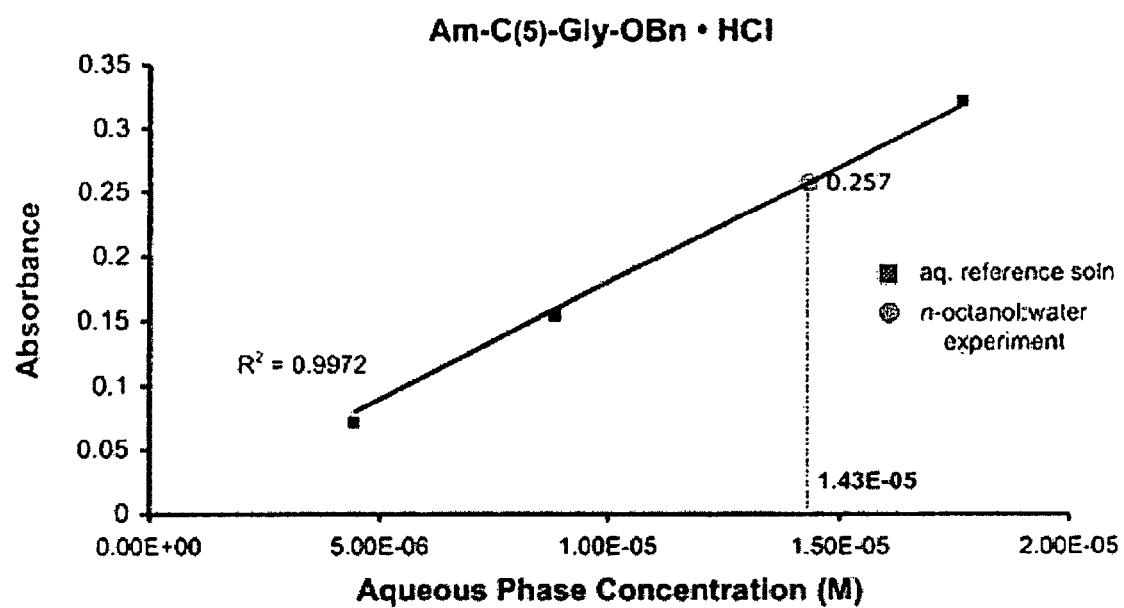
FIG. 10A: AmC(5)GlyOBn.HCl.
Figure 10B:
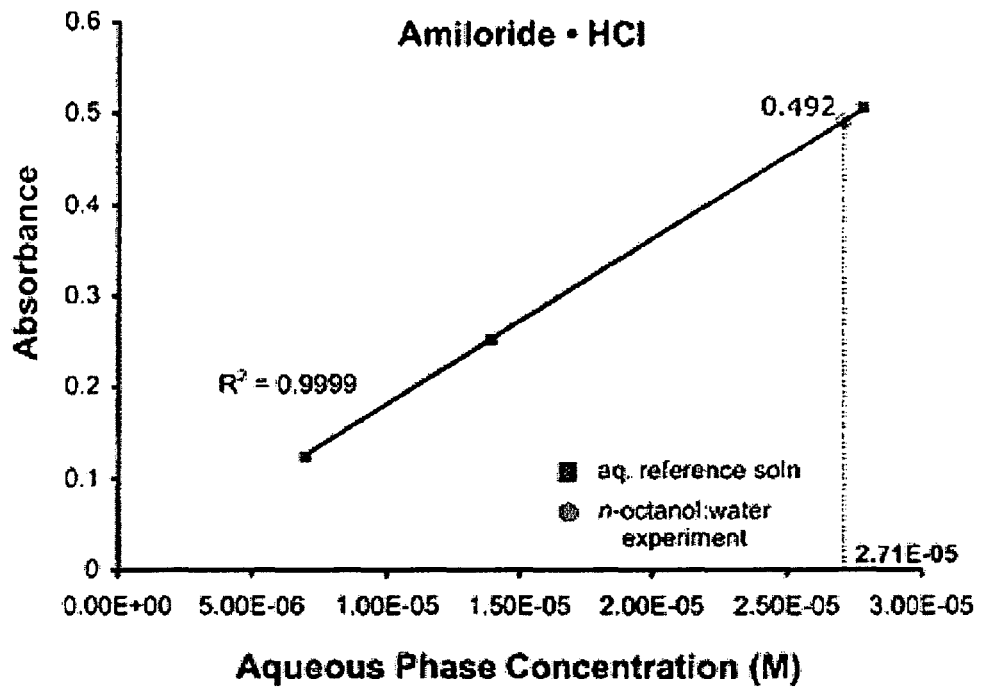
FIG. 10B: Amiloride-HCl.

AmC(5)GlyOH has been shown to be cell-impermeant. Both compounds are fluorescent with comparable fluorescent excitation coefficients. U87 glioma cells were incubated with 50 uM of each compound for 180 min followed by washing the cells ×2 with PBS. AmC(5)GlyOBn permeates glioma cells while AmC(5)GlyOH does not. Both compounds reversibly and comparably inhibit NHE1 and extracellular uPA. n The intracellular permeation by AmC(5)Gly)OBn corresponds with its partitioning between octonol and water (FIG. 10). The log(P) of the hydrochloride salt of AmC(5)Gly)OBn was experimentally determined to be −0.63, as compared with −1.57 for amiloride.HCL. The base form of AmC(5)Gly)OBn that permeates cell membranes is more lipophilic than the HCL salt. The log(P) and molecular weight of AmC(5)Gly)OBn corresponds with the log(P) and MW ranges of more than 80% of the pharmaceutical agents listed in the Comprehensive Medicinal Chemistry (CMC) database as initially described by Lipinsky and more recently, by Ghose et al. J. Comb. Chem. 1999, 1, 55-68.

Figure 11A:
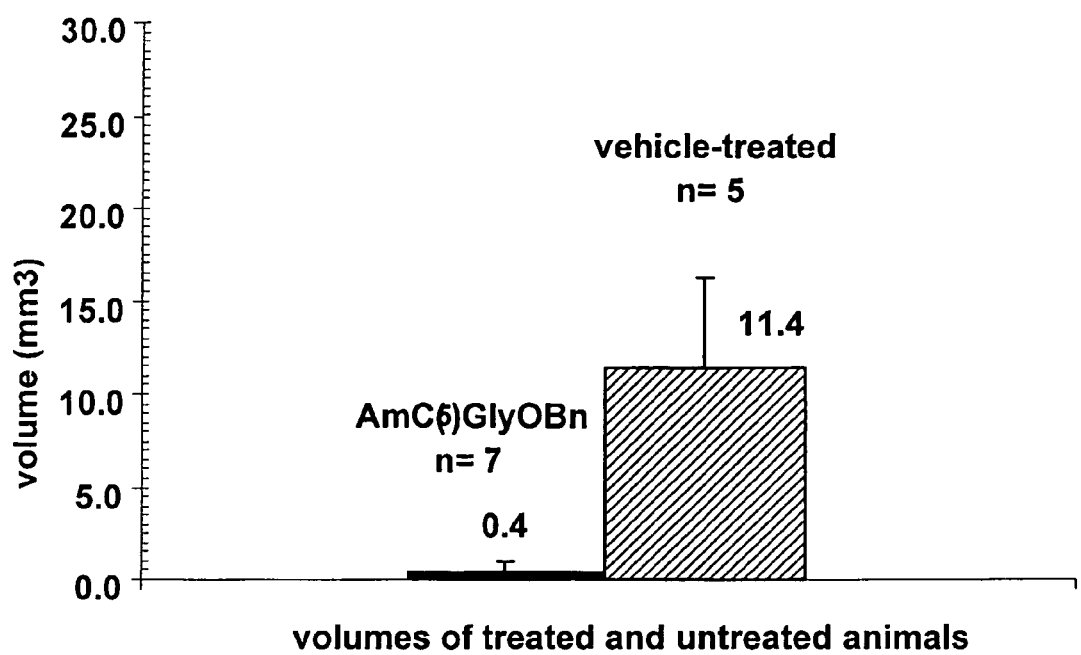
FIG. 11A: Tumor volume determined by stereology.
Figure 11B:
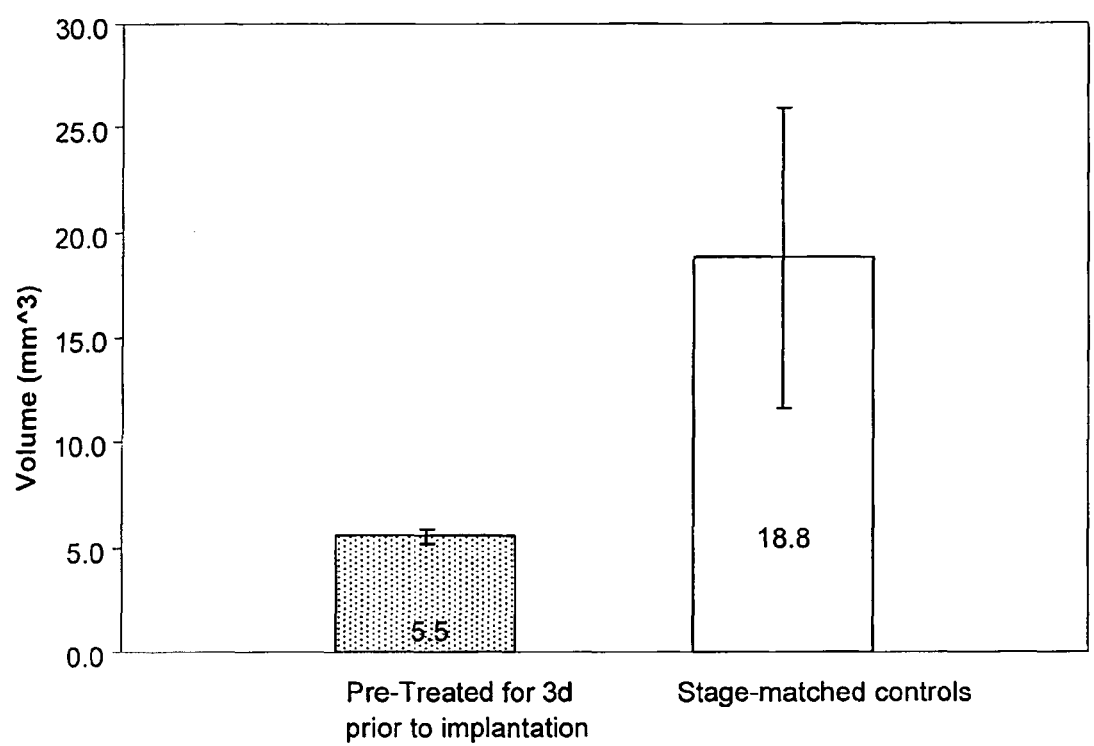
FIG. 11B: Tumor volume determined by NMR.

The preliminary data demonstrating that pre-treatment with AmC(5)-Gly-OBn prevented or retarded tumor recurrence was obtained using small animal NMR. It has been demonstrated that 3d pre-treatment of athymic rats followed by stereotaxic injection of glioma cells with subsequent daily, intrathecal AmC(5)GlyOBn ((300 pmol/d) for 10d prevented or significantly impaired U87 tumor proliferation. The data presented herein measured intracranial tumor volumes using 7T small animal NMR (FIG. 11B). Tumor volumes were precisely measured using stereological methodologies in treated- and vehicle-treated animals (FIG. 11A). Vehicle-treated controls were paired with AmC(5)GlyOBn-treated animals by stereotaxically injecting 5 ul volume (5×10$^4$ cells) from the same suspension of injected U87 glioma cells. NMR over-estimated the tumor volumes of AmC(5)-GlyOBn animals by detecting the tissue changes created by the stereotaxic needle. FIG. 11 compares mean tumor volumes+SD of treated- and vehicle-treated animals determined by stereology (FIG. 11A) with the mean tumor volumes determined from earlier set of experiments using NMR (FIG. 11B). Three of the seven treated animals did not have demonstrable tumors. Morphologically, the Nissl-stained intracerebral tumors treated with AmC(5)-GlyOBn are microscopic and well-circumscribed, while DMSO-treated tumors are macroscopic and contain 3-9 "fingers" invading into the normal cortex The stereological data acquired from a separate group of animals indicates that the drug impaired or prevented subsequent growth of intracranial tumor xenografts in pre-treated animals as a model of glioma recurrence. The histological data support that inhibition of the intracellular uPA with disruption of the OPN-uPA autocrine system, and possibly coupled with simultaneous inhibition of sodium-proton transport (NHE1), identifies a class of bioactivated compounds that impair intracranial tumor recurrence of a class of highly invasive and rapidly growing human glioblastoma cell lines.

Example 23

Figure 8:
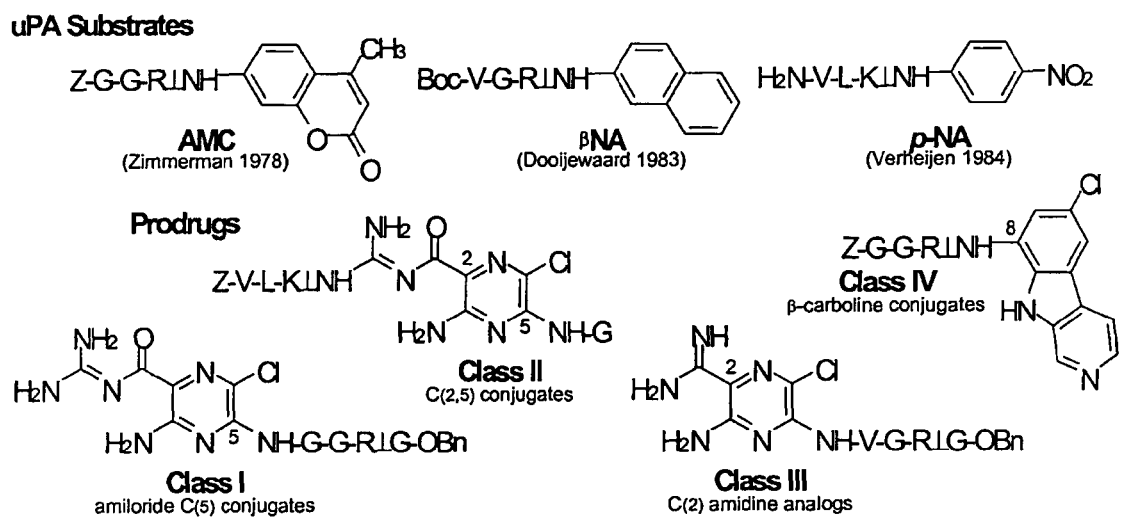
FIG. 8 illustrates representative peptide prodrugs with peptide sequences modeled after selective uPA-peptide substrates (⊥=scissile bond; site of enzymatic cleavage).

Intracellular uPA Active in Glioblastomas to Activate a Prodrug uPA is synthesized as pro-uPA, and there are endogenous intracellular inhibitors of uPA. Human U87 glioma cells, used for in vivo xenograft studies, have considerable uPA activity in cell homogenates obtained from cells washed 2× with PBS. However, endogenous uPA inhibitors could be disrupted with homogenization so uPA activity in intact human glioblastoma cell lines was examined. A cell permeant, non-fluorescent uPA substrate, Z-G-G-R-AMC, fluoresces when cleaved by active uPA. Intact glioma cells were incubated with Z-G-G-R-AMC for 90 min and then washed ×2 with PBS. Intact U87, U118, U251 human glioma cell lines demonstrate considerable intracellular fluorescence generated by the cleaved AMC group when visualized with a semi-quantitative fluorescent microscope as described previously. These data demonstrate that intracellular uPA in glioma cells is sufficient to cleave a peptide-based substrate or prodrug, such as Z-G-G-R-AMC or AmC(5)G-G-R-OBn, see FIG. 8.

Example 24

Representative Data for Compounds of the Invention

FIG. 12 provides a table showing representative data for compounds of the invention.

Example 25

Assay for the Identification of uPA Inhibitors

Significance: Approximately 15-25% of breast cancer patients without lymph node metastases develop systemic relapse. Sensitive immunocytochemical or molecular assays permit detection of single disseminated tumor cells in bone marrow or the peripheral blood. These cells are detected in 10-60% of breast cancer patients without clinical or even histopathologic signs of metastasis and correspond with subsequent development of clinically evident bone metastases, and a worse outcome from breast cancer (Alix-Panabieres C, Muller V and Pantel K (2007) Current status in human breast cancer micrometastasis. *Curr Opin Oncol* 19:558-563).

Increased expression of the urokinase plasminogen activator (uPA) systems is associated with increased invasion and metastasis of cancerous cells. A set of biochemical markers that are associated with breast cancer invasion, metastasis, and increased recurrence comprise components of the urokinase plasminogen activator system (Tetu B, Brisson J, Lapointe H and Bernard P (1998) Prognostic significance of stromelysin 3, gelatinase A, and urokinase expression in breast cancer. *Hum Pathol* 29:979-985; Dublin E, Hanby A., Patel N K, Liebman R and Barnes D (2000) Immunohistochemical expression of uPA, uPAR, and PAI-1 in breast carcinoma. Fibroblastic expression has strong associations with tumor pathology. *Am J Pathol* 157:1219-1227). Increased uPA, uPAR, and/or PM-1 are associated with tumor progression and with shortened disease-free and/or overall survival in patients afflicted with malignant solid tumors. Strong prognostic value to predict disease recurrence and overall survival has been documented for patients with cancer of the breast, ovary, cervix, endometrium, stomach, colon, lung, bladder, kidney, prostate, fibrosarcomas, and high grade brain gliomas (Schmitt M, Harbeck N, Thomssen C, Wilhelm O, Magdolen V, Reuning U, Ulm K, Hofler H, Janicke F and Graeff H (1997) Clinical impact of the plasminogen activation system in tumor invasion and metastasis: prognostic relevance and target for therapy. *Thromb Haemost* 78:285-296; Achbarou A, Kaiser S, Tremblay G, Ste-Marie L G, Brodt P, Goltzman D and Rabbani S A (1994) Urokinase overproduction results in increased skeletal metastasis by prostate cancer cells in vivo. *Cancer Res* 54:2372-2377; Coradini D and Daidone M G (2004) Biomolecular prognostic factors in breast cancer. *Curr Opin Obstet Gynecol* 16:49-55; Fischer K, Lutz V, Wilhelm O, Schmitt M, Graeff H, Heiss P, Nishiguchi T, Harbeck N, Kessler H, Luther T, Magdolen V and Reuning U (1998) Urokinase induces proliferation of human ovarian cancer cells: characterization of structural elements required for growth factor function. *FEBS Lett* 438: 101-105; Madsen M A, Deryugina E I, Niessen S, Cravatt B F and Quigley J P (2006) Activity-based protein profiling implicates urokinase activation as a key step in human fibrosarcoma intravasation. *J Biol Chem* 281:15997-16005).

The urokinase plasminogen activator (uPA) system includes uPA and plasminogen activator inhibitor types 1 and 2. Extracellular uPA binds to uPAR and activates plasmin to facilitate extracellular matrix degradation. Intracellular uPA system is part of a complex autocrine and paracrine pathway system that regulates cancer cell proliferation, survival, and angiogenesis (Duffy M J, McGowan P M and Gallagher W M (2008) Cancer invasion and metastasis: changing views. *J Pathol* 214:283-293). When uPAR-dependent activation of ERK predominates over p38 signaling, tumorigenicity is maintained. With uPA or uPAR downregulation p38 activation predominates resulting in tumor dormancy and maintains the survival of hematogenously disseminated detached cancer cells (Ranganathan A C, Adam A P and Aguirre-Ghiso J A (2006) Opposing roles of mitogenic and stress signaling pathways in the induction of cancer dormancy. *Cell Cycle* 5:1799-1807).

uPA system in Breast Cancer Cells:

Urokinase-type plasminogen activator (uPA) is a serine protease that is expressed as an inactive pro-uPA in normal cells types, is secreted, and binds up to the receptor, uPAR with resultant activation of both the ligand and its receptor. uPA and uPAR are frequently overexpressed in breast cancer and associated with rapidly progressive disease (Bolla et al., 1990; Duffy et al., 1999). uPA-binding to uPAR activates multiple cell signaling proteins including FAK, c-Src and ERK. As uPAR is glycosyl phosphatidylinositol (GPI)-anchored, its function in cell signaling requires plasmalemmal co-receptors that include integrins, EGRF, c-MET. Both EGFR and c-MET are frequently upregulated in single migratory breast cancer and in glioma cells with cMET upregulated under hypoxia. uPAR is required for EGF to induce proliferation of murine embryonic fibroblasts (MEFs) and MDA-MB 231 breast cancer cells with uPAR required for Tyr-845 phosphorylation in EGRF and for activation of STAT5b downstream of c-Src.

High Grade Glioma Cells and Metastatic Breast Cancer Cells Express Active Intracellular uPA.

Approximately 15% of breast cancer is recurrent with metastatic cancer arising from hypoxic-ischemic microenvironments, most notably bone marrow (ref). These highly metastatic forms of breast cancer utilize the same urokinase plasminogen system as high grade gliomas that is also activated by c-MET and EGRF. uPA and uPAR expression corresponds with tumor invasiveness and poor patient prognosis for these disparate cancers. In normal cell types there is no intracellular uPA activity, and pro-uPA is secreted to bind to its receptor (uPAR) to become activated. However, upregulation of hepsin, and cathepsins B and L in highly infiltrative breast and glioma cells, respectively, cause intracellular cleavage of pro-uPA. For this reason, we examined whether breast cancer cell lines, like high grade gliomas, expressed intracellular uPA.

The glioma cells (A-C) and the breast cancer cell lines (D-E) express high levels of intracellular, activated uPA. A cell permeant commercial substrate (Z-GGR-AMC) becomes fluorescent when cleaved by active uPA. The assay incubates either fresh tissue or intact cells for 2 h with the cell permeant substrate, cells are washed, and visualized using a fluorescent microscope. Normal brain cells types, low grade glioma cells and non-metastatic breast cancer cell lines do not express active intracellular uPA. This simple cytological test can predict whether the cancer cell is (1) at high risk to be metastatic and (2) will respond to this class of compounds.

Usage:

Identification of active uPA in cancer cells is invisioned to be employed as (1) a diagnostic tool in fresh surgical biopsy material to identify increased risk for invasion and metastasis (2) as an application to identify cancer cell types with increased susceptibility to therapeutic agents that impair the uPA system.

Impairment of Intracellular uPA Expression Causes Apoptosis and Impaired Proliferation in Glioma and Breast Cancer Cells.

Stably transfecting breast cancer cells with antisense uPA decreased the amount of cell-bound uPA, disrupted actin cytoskeleton formation, cell migration and caused apoptotic cell death. There is evidence of autocrine regulation of uPAR by uPA such that inhibition of intracellular uPA expression reduces total uPA and uPAR expression and cell viability. Anti-sense inhibition of pro-uPA and uPA expression is associated with decreased uPAR expression with decreased uPAR protein corresponding with increased apoptosis. SNB19 glioblastoma cells expressing antisense uPAR constructs are less invasive than parental cells when injected in vivo and undergo increased apoptosis. Glioma cells with reduced uPAR protein expression are more susceptible to TNFa-induced apoptosis than parental cells. Plasminogen cleavage by the catalytic portion of uPA is associated with increased apoptosis, while the non-catalytic ATF region (residues 1-135) of uPA protects cells from apoptosis associated with cell detachment (anoikis). Silencing of Bcl-xL expression prevents uPA protection from anoikis and uPA expression appears to be required for transcription of anti-apoptotic Bcl-xL. In an immortalized retinal pigment epithelial cell line, Bcl-xL expression was reduced following silencing of uPA expression and corresponds with reduced activation of both the AKT and ERK pathways. Silencing of uPA expression in glioma cells facilitates staurosporine-induced apoptosis and reduces AKT pathway activation.

Intracellular Urokinase Plasminogen Activator (uPA) Represents a New Pharmacological Target that Promises to Cause Apoptotic Events in Gliomas.

Invasive cancer cells utilize the uPA pathway to activate a proteolytic cascade leading to breakdown of extracellular matrix. uPA is synthesized as a single chain inactive proenzyme (pro-uPA). In normal cells, pro-uPA is secreted outside the cell, where it binds to its receptor (uPAR). However, in many invasive and proliferating cancer cells, uPA undergoes intracellular enzymatic activation whereas intracellular uPA is not detected in normal brain or its normal vasculature. Levels of uPA and uPAR are significantly increased with tumor progression from grades I to grade IV, and are directly associated with increased tumor invasiveness.

Therapeutic Targeting Extracellular uPA-uPAR.

Pharmaceutical companies have focused upon disrupting the interaction between uPA and uPAR (Rockaway T W (2003) Small molecule inhibitors of urokinase-type plasminogen activator. *Expert Opinion Therapeutic Patents* 13:773-786). Currently, WX-UK1 is 3-aminophenylalanine derivative in phase II human clinical trials and shown to be non-toxic. WX-UK1 suppresses rat breast cancer metastasis and reduction of primary tumour growth (Setyono-Han B, Sturzebecher J, Schmalix W A, Muehlenweg B, Sieuwerts A M, Timmermans M, Magdolen V, Schmitt M, Klijn J G and Foekens J A (2005) Suppression of rat breast cancer metastasis and reduction of primary tumour growth by the small synthetic urokinase inhibitor WX-UK1. *Thromb Haemost* 93:779-786). WX-340 is a peptide derived inhibitor of uPAR that suppresses endotoxin and surgery-accelerated growth of murine metastases of colorectal cells.

Novel Intracellular Targeting of uPA system kills metastatic breast cancer cells. We have developed a new class of small molecules that target both the extracellular and the intracellular uPA system and have compared these novel compounds to inhibitors of extracellular uPA currently in phase II testing. In contrast to the commercial extracellular inhibitors of uPA-uPAR, our lead compounds kill metastatic breast cancer cells in addition to impairing their adherence, proliferation, and migration. These compounds appear to kill cancer cells residing in poorly vascularized tumor microenvironments utilizing mechanisms independent of cell cycle progression. The cell-impermeant homolog to the lead compound inhibited glioma cell adherence to extracellular matrix (hyaluronin, MATRIGEL), impaired proliferation and migration.

Assay:

Intracellular uPA activity in glioma cell lines (U87, U118, U251) is compared with 0.1 U of commercial uPA, and with normal rat astrocytes. This assay uses a cell permeant peptide that releases a fluorescent AMC group when cleaved selectively by uPA.

Procedure:

Cells are treated for the indicated times with 100 uM Z-G-G-R-AMC (Calbiochem #672159-25MG) in PBS for up to 120 min. The cells are washed with PBS twice, and visualize for intracellular fluorescence using a fluorescent microscope.

Figure 13A:
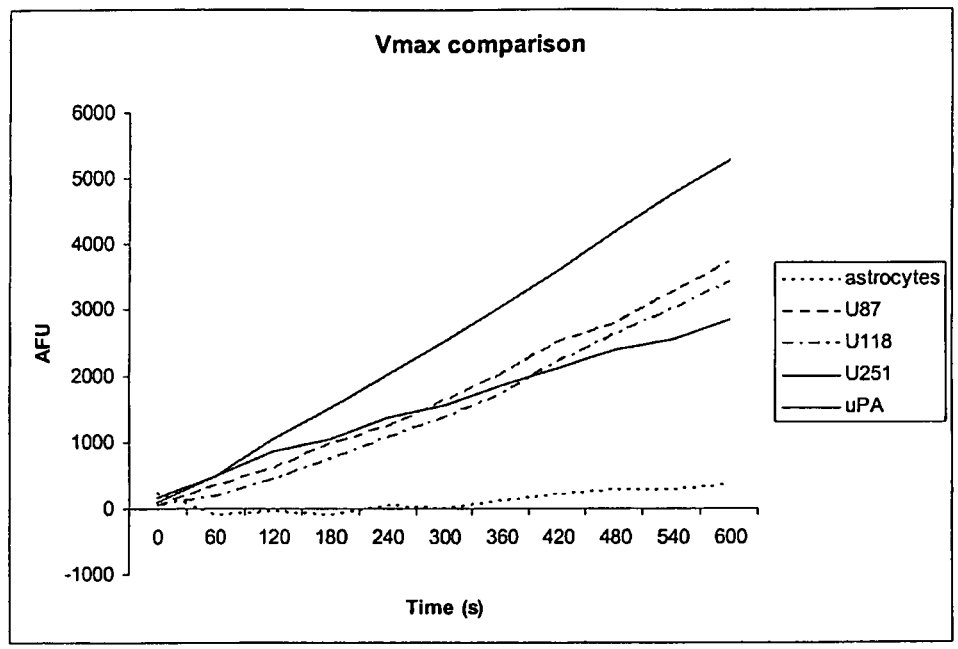
FIG. 13A is a graph illustrating the results of a glioma cell line fluorescence assay to detect uPA activity.
Figure 13B:
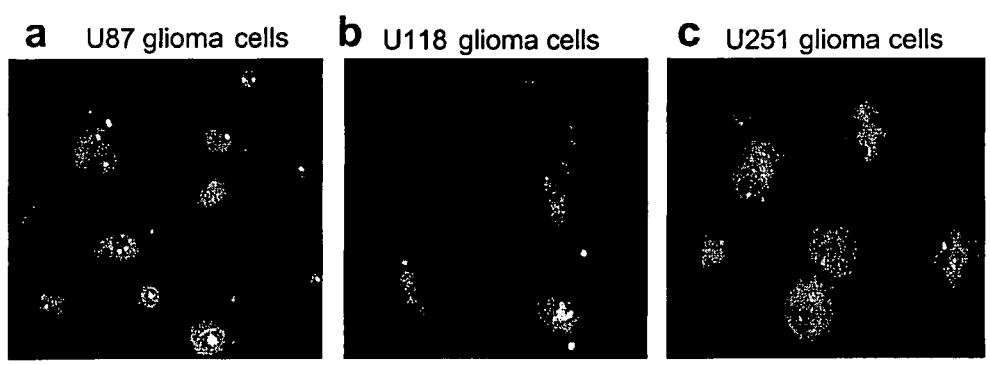
FIGS. 13B and 13C show results from glioma cells and breast cancer cells.
Figure 13C:

As can be seen in FIG. 13, the enzyme assay demonstrates that by 120 sec there is a 1000-fold signal in cancer cells above normal cell background (essentially 0); validating the utility of this intracellular assay.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A compound of formula II:

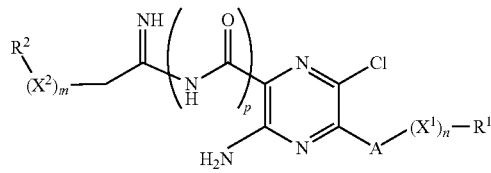

II wherein
$R^2$ is independently selected from the group consisting of H, $C_{1-8}$ alkyl, $C_{0-8}$alkylaryl, carboxy-$C_{1-8}$ alkyl and carboxy$C_{0-8}$alkylaryl;

A is an amino acid moiety, <—NH—CHR$^3$—CO—>, wherein $R^3$ indicates an amino acid side chain, —> and <— indicate the attachment sites to $X^1$ or $R^1$ and the rest of the molecule;

p is 0;

n is an integer of from 0 to 100;

m is an integer of from 0 to 100;

—$(X^1)_n$— is a sequence of n independently selected amino acid units, —NH—$R^4$—CO—, attached to A via an amide linkage to the amino terminus of the sequence and to $R^1$ via the carboxy terminus of the sequence, wherein each $R^4$ is independently an optionally substituted alkylene;

$R^1$ is selected from the group consisting of $C_{1-8}$ alkoxy, aryl-$C_{0-8}$alkoxy, heterocyclyl and amino, each of which is optionally substituted with from 1 to 3 substituents each independently selected from the group consisting of $C_{1-8}$ alkyl, aryl-$C_{0-8}$alkyl and heterocyclyl; or a therapeutic agent; and —$(X^2)_m$— is a sequence of m independently selected amino acid units, —NH—$R^4$—CO—, attached to $R^2$ via the amino terminus of the sequence and the rest of the molecule via an amide linkage to the carboxy terminus of the sequence, wherein each $R^4$ is independently an optionally substituted alkylene or $C_{3-7}$ cycloalkylene.

2. A compound of claim 1, wherein n is 0.

3. A compound of claim 1, having the formula:

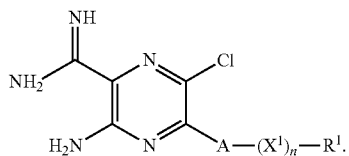

IIa

* * * * *